US006156495A

United States Patent [19]
Pilot-Matias et al.

[11] Patent Number: 6,156,495
[45] Date of Patent: *Dec. 5, 2000

[54] HEPATITIS GB VIRUS RECOMBINANT PROTEINS AND USES THEREOF

[75] Inventors: Tami J. Pilot-Matias, Green Oaks, Ill.; Thomas P. Leary, Kenosha, Wis.; John N. Simons, Grayslake, Ill.; Robert J. Carrick; Teresa K. Surowy, both of Kenosha, Wis.; Suresh M. Desai; George J. Dawson, both of Libertyville, Ill.; Anthony Scott Muerhoff, Kenosha, Wis.; Isa K. Mushahwar, Grayslake, Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/629,463

[22] Filed: Apr. 19, 1996

Related U.S. Application Data

[62] Continuation-in-part of application No. 08/480,995, Jun. 7, 1995, abandoned, which is a continuation-in-part of application No. 08/417,629, Apr. 6, 1995, Pat. No. 5,981,172, and a continuation-in-part of application No. 08/424,550, filed as application No. PCT/US95/02118, Feb. 14, 1995, which is a continuation-in-part of application No. 08/377,557, Jan. 30, 1995, abandoned, which is a continuation-in-part of application No. 08/344,185, Nov. 23, 1994, abandoned, and a continuation-in-part of application No. 08/344,190, Nov. 23, 1994, abandoned, which is a continuation-in-part of application No. 08/283,314, Jul. 29, 1994, abandoned, which is a continuation-in-part of application No. 08/242,654, May 13, 1994, abandoned, which is a continuation-in-part of application No. 08/196,030, Feb. 14, 1994, abandoned.

[51] Int. Cl.$^7$ .............................. C12Q 1/70; C12N 15/00
[52] U.S. Cl. ........................... 435/5; 435/320.1; 530/826; 530/350
[58] Field of Search .............................. 424/185.1, 189.1, 424/204.1, 228.1; 435/5, 7.1, 7.92, 69.1, 69.3, 69.7, 320.1; 436/501; 530/350, 826; 930/223

[56] References Cited

U.S. PATENT DOCUMENTS

| | | |
|---|---|---|
| 4,743,535 | 5/1988 | Carrico . |
| 4,876,187 | 10/1989 | Duck et al. . |
| 5,275,947 | 1/1994 | Arima et al. ........................ 435/252.33 |
| 5,399,346 | 3/1995 | Anderson et al. . |
| 5,527,669 | 6/1996 | Resnick et al. . |
| 5,576,302 | 11/1996 | Cook et al. . |
| 5,766,840 | 6/1998 | Kim et al. ..................................... 435/5 |

FOREIGN PATENT DOCUMENTS

| | | |
|---|---|---|
| 0318216 | 5/1989 | European Pat. Off. . |
| 9000597 | 1/1990 | WIPO . |
| 9408002 | 4/1994 | WIPO . |
| 9418217 | 8/1994 | WIPO . |
| 9532290 | 11/1995 | WIPO . |
| 9532291 | 11/1995 | WIPO . |
| 9532292 | 11/1995 | WIPO . |
| WO 95/32291 | 11/1995 | WIPO . |
| 9506266 | 5/1996 | WIPO . |

OTHER PUBLICATIONS

T. Peters et al., Frequency of Hepatitis C in Acute Post–Transfusion Hepatitis After Open–Heart Surgery: A Prospective Study in 1,476 Patients, *Journal of Medical Virology* vol. 39: 139–145 (1993).

R. Purcell, The Discovery of the Hepatitis Viruses, *Gastroenterology* vol. 104, No. 4: 955–963 (1993).

G. Dawson et al., Solid–phase enzyme–linked immunosobent assay for hepatitis E virus IgG and IgM antibodies utilizing recombinant antigens and synthetic peptides, *Journal of Virological Methods* vol. 38: 175–186 (1992).

P. Yarbough et al., Hepatitis E Virus: Identification of Type–Common Epitopes, *Journal of Virology* vol. 65 No. 11: p. 5790–5797 (1991).

H. Alter et al., Detection of Antibody to Hepatitis C Virus in Prospectively Followed Transfusion Recipients with Acute and Chronic Non–A, Non–B Hepatitis, *The New England Journal of Medicine* vol. 321 No. 22: p. 1494–1500 (1989).

M. Alter et al., Risk Factors for Acute Non–A, Non–B Hepatitis in the United States and Association With Hepatitis C Virus Infection, *JAMA* vol. 264 No. 17: p. 2231–2235 (1990).

J. Dienstag, Hepatitis Non–A, Non–B: C at Last, *Gastroenterology* vol. 99 No. 4: p. 1177–1180 (1990).

G. Reyes et al., Isolation of a cDNA from the Virus Responsible for Enterically Transmitted Non–A, Non–B Hepatitis, *Science* vol. 247 : p. 1335–1339 (1990).

G. Kuo et al., An Assay for Circulating Antibodies to a Major Etiologic Virus of Human Non–A, Non–B Hepatitis, *Science* vol. 244 : p. 362–364 (1989).

A. Weiner et al., Detection of hepatitis C viral sequences in non–A, non–B hepatitis, *The Lancet* vol. 335: p. 1–3 (1990).

G. Schlauder et al., Viraemia in Egyptian children with hepatitis E virus infection, *The Lancet* vol. 341: p. 378 (1993).

N. Lisitsyn et al., Cloning the Differences Between Two Complex Genomes, *Science* vol. 259: p. 946–951 (1993).

V. Thiers et al., Post–transfusional anti–HCV–negative non–A non–B hepatitis (II) serological and polymerase chain reaction analysis for hepatitis C and hepatitis B viruses, *Journal of Hepatology* vol. 18: p. 34–39 (1993).

Hepatitis C virus upstanding, *The Lancet* vol. 335: p. 1431–1432 (1990).

(List continued on next page.)

*Primary Examiner*—Donna C. Wortman
*Assistant Examiner*—Brenda G. Brumback
*Attorney, Agent, or Firm*—Cheryl L. Becker; Diannne Casuto; Priscilla Porembski

[57] ABSTRACT

Recombinantly produced hepatitis GB Virus (HGBV) amino acid sequences useful for a variety of diagnostic and therapeutic applications, kits for using the HGBV amino acid sequences and antibodies which specifically bind to HGBV. Also provided are methods for producing antibodies, polyclonal or monoclonal, from the HGBV recombinantly produced amino acid sequences.

27 Claims, 7 Drawing Sheets

OTHER PUBLICATIONS

W. Parks et al., Attempted Isolation of Hepatitis Viruses in Marmosets, *The Journal of Infectious Diseases* vol. 120 No. 5: 539–547 (1969).

A. Holmes et al., Specific Neutralization of Human Hepatitis Type A in Marmoset Monkeys, *Nature* vol. 243: p. 419–420 (1973).

P. Provost et al., Physical, Chemical and Morphologic Dimensions of Human Hepatitis A Virus Strain CR326 (38578), *Proceeding of the Society for Experimental Biology and Medicine* vol. 148: p. 532–539 (1975).

Q. Choo et al., Isolation of a cDNA Clone Derived from a Blood–Borne Non–A, Non–B Viral Hepatitis Genome, *Science* vol. 244: p. 359–361 (1989).

J. Almeida et al., Morphology of the GB hepatitis agent, *Nature* vol. 261: p. 608–609 (1976).

F. Deinhardt et al., Studies on the Transmission of Human Viral Hepatitis to Marmoset Monkeys, *Journal of Experimental Medicine* vol. 125: p. 673–688, Plate 81–86 (1966).

J. Dienstag, Non–A, Non–B Hepatitis. II. Experimental Transmission, Putative Virus Agents and Markers, and Prevention, *Gastroenterology* vol. 85 No. 3: p. 743–768 (1983).

F. Hollinger et al., Transfusion–Transmitted Viruses Study: Experimental Evidence for Two Non–A, Non–B Hepatitis Agents, *Journal of Infectious Diseases* vol. 142 No. 3: p. 400–407 (1980).

D. Bradley, Transmission, Etiology, and Pathogenesis of Viral Hepatitis Non–A, Non–B in Non–Human Primates, *Advances in Hepatitis Research:* p. 268–280 (1984).

F. Deinhardt et al., Hepatitis in marmosets, *The American Journal of the Medical Sciences* vol. 270: p. 73–80 (1975).

S. Kalter, Comparison of Infectivity of Human Non–A/Non–B Hepatitis and the GB Hepatitis Agent in Marmosets, *Viral and Immunological Diseases in Nonhuman Primates;:* p. 221–224 (1983).

E. Tabor et al., Transmission of Human Non–A, Non–B Hepatitis to Chimpanzees Following Failure to Transmit GB Agent Hepatitis, *Journal of Medical Virology:* p. 103–108 (1980).

D. Bradley et al., Posttransfusion Non–A, Non–B Hepatitis: Physicochemical Properties of Two Distinct Agents, *The Journal of Infectious Diseases* vol. 148 No. 2: p. 254–265 (1983).

J. Dienstag, Virus–like particles and GB agent hepatitis, *Nature* vol. 264: p. 260–261 (1976).

P. Karayiannis et al., Studies of GB Hepatitis Agent in Tamarins, *Hepatology* vol. 9 No. 2: p. 186–192 (1989).

J. Melnick, Classification of Hepatitis A Virus as Enterovirus Type 72 and of Hepatitis B Virus as Hepadnavirus Type 1, *Intervirology* vol. 18: p. 105–106 (1982).

W. Parks et al., Characterization of Marmoset Hepatitis Virus, *The Journal of Infectious Diseases* vol. 120 No. 5: p. 548–559 (1969).

S. Feinstone et al., Hepatitis A: Detection by Immune Electron Microscopy of a Viruslike Antigen Associated with Acute Illness, *Science* vol. 182: p. 1026–1028 (1973).

E. Tabor et al., Lack of Susceptibility of Marmosets to Human Non–A, Non–B Hepatitis, *The Journal of Infectious Diseases* vol. 140 No 5: p. 794–797 (1979).

E. Fagan et al., Toga Virus–Like Particles in Acute Liver Failure Attributed to Sporadic Non–A, Non–B Hepatitis and Recurrence After Liver Transplantation, *Journal of Medical Virology* vol. 38: p. 71–77 (1992).

J. Dienstag, Virus particles in marmoset hepatitis, *Nature* vol. 267: p. 729–730 (1977).

F. Deinhardt et al., Hepatitis in Marmosets, *The Journal of Infectious Diseases* vol. 121 No. 3: p. 351–354 (1970).

F. Deinhardt et al., The Mythology of Various Hepatitis A Virus Isolates, *International Symposium on Viral Hepatitis:* p. 390–404 (1975).

M. Alter et al., The Natural History of Community–Acquired Hepatitis C in the United States, *The New England Journal of Medicine* vol. 327 No. 27: p. 1899–1905 (1992).

R. Gibbs, Polymerase chain reaction techniques, *Analytical Biotechnology:* p. 69–75 (1991).

S. Friedman et al., The core element of the EcoRII methylase as defined by protease digestion and deletion analysis, *Nucleic Acids Research* vol. 19 No. 19: p. 5403–5408 (1991).

A. Rosenthal et al., Genomic walking and sequencing by oligo–cassette mediated polymerase chain reaction, *Nucleic Acids Research* vol. 18 No. 10: p. 3095–3096 (1990).

A. Akowitz, Protected endogenous retroviral sequences copurify with infectivity in experimental Creutzfeldt–Jakob disease, *Archives of Virology* vol. 130: p. 301–316 (1993).

Non–A, Non–B?, *The Lancet* vol. 2: p. 64–65 (1975).

F. Hollinger, Non–A, Non–B Hepatitis Viruses, *Virology :* p. 2239–2273 (1990).

J. Dienstag, Non–A, Non–B Hepatitis I. Recognition, Epidemiology, and Clinical Features, *Gastroenterology* vol. 85 No. 2: p. 439–462 (1983).

J. Strauss et al., Structure and Function of the Flavivirus and Pestivirus Genomes, *Viral Hepatitis and Liver Disease:* p. 333–344 (1990).

H. Alter et al., Posttransfusion Hepatitis After Exclusion of Commercial and Hepatitis–B Antigen–Positive Donors, *Annals of Internal Medicine* vol. 77 No. 5: p. 691–699 (1972).

H. Alter et al., Clinical and Serological Analysis of Transfusion–Associated Hepatitis, *The Lancet:* p. 838–841 (1975).

S. Feinstone et al., Transfusion–Associated Hepatitis Not Due To Viral Hepatitis Type A or B, *The New England Journal of Medicine* vol. 292 No. 15: p. 767–770 (1975).

J. Simons et al., Identification of two flavivirus–like genomes in the GB Hepatitis agent, *Proc. Natl. Acad. Sci. USA* vol. 92: p. 3401–3405 (1995).

J. Simons et al., Isolation of novel virus–like sequences associated with human hepatitis, *Nature Medicine* vol. 1 No. 6: p. 564–568 (1995).

G. Schlauder et al., Molecular and Serologic Analysis in the Transmission of the GB Hepatitis Agents, *Journal of Medical Virology* vol. 46: p. 81–90 (1995).

M. Yoshiba et al., Detection of the GBV–C hepatitis virus genome in serum from patients with fulminant hepatitis of unknown aetiology, *The Lancet* vol. 346: p. 1131–1132 (1995).

J. Linnen et al., Molecular Cloning and Disease Association of Hepatitis G Virus: A Transfusion–Transmissible Agent, *Science* vol. 271: p. 505–508 (1996).

A. Zuckerman, The new GB hepatitis viruses, *The Lancet* vol. 345: p. 1453–1455 (1995).

L. Altman, Three Newly Discovered Viruses May Cause Unexplained Hepatitis, *The New York Times Medical Science ,* Apr. 11, 1995.

L. Altman, Newly Found Viruses May Cause Hepatitis, *The New York Times Medical Science,* Apr. 10, 1995.

T. Leary et al., Sequence and Genomic Organization of GBV–C: A novel Member of the Flaviviridae Associated With Human Non–A–E Hepatitis, *Journal of Medical Virology* vol. 48: p. 80–87 (1996).

G. Caetano–Anolles et al., DNA Amplification Fingerprinting Using Arbitrary Oligonucleotide Primers, *Applied Biochemistry and Biotechnology* vol. 42: p. 189–200 (1993).

B. Bassam, DNA amplification fingerprinting of bacteria, *Applied Microbiology and Biotechnology* vol. 38: p. 70–76 (1992).

G. Caetano–Anolles et al., DNA Amplification Fingerprinting Using Very Short Arbitrary Oligonucleotide Primers, *Biotechnology* vol. 9: p. 553–557 (1991).

J. Welsh et al., Fingerprinting genomes using PCR with arbitrary primers*, *Nucleic Acids Research* vol. 18 No. 24: p. 7213–7218 (1990).

J. Welsh et al., Arbitrarily primed PCR fingerprinting of RNA, *Nucleic Acids Research* vol. 20 No. 19: p. 4965–4970 (1992).

J. Williams et al., DNA polymorphisms amplified by arbitrary primers are useful as genetic markers, *Nucleic Acids Research* vol. 18 No. 22: p. 6531–6535 (1990).

P. Liang et al., Differential Display of Eukaryotic Messenger RNA by Means of the Polymerase Chain Reaction, *Science* vol. 257: p. 967–971 (1992).

P. Liang et al., Distribution and cloning of eukaryotic mRNAs by means of differential display: refinements and optimization, *Nucleic Acids Research* vol. 21 No. 14: p. 3269–3275 (1993).

S. Chan et al., Journal of General Virology, 73: 1131–1141 (1992).

R. Koshy et al., Trends in Biotechnology, 14(10): 364–369 (1996).

M. J. Slater et al., *Exp. Opin. Ther. Patents,* vol. 6 (8): 739–746 (1996).

A. Muerhoff et al., *Journal of Virology,* 69 (9), 5621–5630 (1995).

Gura, *Science,* vol. 270, pp. 575–577 (1995).

Brown, *Washington Post,* pp. 1 & A22 (Dec. 8, 1995).

S. K. Kuwada et al., *The American Journal of Gastroenterology,* vol. 89, No. 1, pp 57–61 (1994).

A. S. Muerhoff et al., *Journal of Virological Methods,* vol. 61, No. 1, pp. 55–62 (1996).

S. Vijayasarathy, *Nucleic Acids Research,* vol. 18, pp. 2967–2975 (1990).

P. Tijssen, "Practice and Theory of Enzyme Immunoassays", Elsevier, Amsterdam, pp. 333–340 (1985).

A. Takamizawa et al., *Journal of Virology,* vol. 65, No. 3, pp. 1105–1113 (1991).

Farci et al., Science, 258:135–140, Oct. 2, 1992.

Choo et al., "Genetic organization and diversity of the hepatitis C virus", Proc. Natl. Acad. Sci. USA 88, 2451–1455 (1991).

Okamoto et al., "Polyprotein precursor—hepatitis C virus", EMBL Sequence Accession No. S40770, submitted Mar. 1992.

Takamizawa et al., "Structure and Organization of the Hepatitis C Virus Genome Isolated from Human Carriers", J. Virol. 65, 1105–1113 (1991).

Okamoto et al., "Full–Length Sequence of Hepatitis C Virus Genome Having Poor Homology to Reported Isolates: Comparative Study of Four Distinct Genotypes", Virology 188, 331–341 (1992).

HEPATITIS GB VIRUS RECOMBINANT PROTEINS AND USES THEREOF

RELATED APPLICATIONS

This application is a continuation-in-part application of U.S. Ser. No. 08/480,995, filed Jun. 7, 1995, now abandoned which is a continuation-in-part of U.S. Ser. No. 08/417,629, U.S. Pat. No. 5,981,172 filed Apr. 6, 1995, which are incorporated herein by reference. This application also is a continuation-in-part application of U.S. Ser. No. 08/424,550 which is a nationalization of P.C.T. application PCT/US95/02118 filed Feb. 14, 1995, which is a continuation-in-part application of U.S. Ser. No. 08/377,557 filed Jan. 30, 1995, now abandoned, which is a continuation-in-part of U.S. Ser. No. 08/344,185 filed Nov. 23, 1994, now abandoned, and U.S. Ser. No. 08/344,190 filed Nov. 23, 1994, now abandoned, which are each continuation-in-part applications of Ser. No. 08/283,314 filed Jul. 29, 1994, now abandoned, which is a continuation-in-part application of U.S. Ser. No. 08/242,654, now abandoned, filed May 13, 1994, which is a continuation-in-part application of U.S. Ser. No. 08/196,030 filed Feb. 14, 1994, now abandoned, all of which enjoy common ownership and each of which is incorporated herein by reference.

This application is related to U.S. Ser. No. 08/580,038, U.S. Pat. No. 5,807,670, filed Dec. 21, 1995, which is a continuation-in-part application of U.S. Ser. No. 60/002,265, filed Aug. 14, 1995, and also is related to U.S. Ser. No. 08/478,073, U.S. Pat. No. 6,020,122 filed Jun. 7, 1995, which are incorporated herein by reference.

BACKGROUND OF THE INVENTION

This invention relates generally to a group of infectious viral agents now termed the "GB viruses" which cause hepatitis in man, and more particularly, relates to materials such as polynucleotides derived from this group of viruses, polypeptides encoded therein, antibodies which specifically bind to these polypeptides, and diagnostics and vaccines that employ these materials.

Hepatitis is one of the most important diseases transmitted from a donor to a recipient by transfusion of blood products, organ transplantation and hemodialysis; it also can be transmitted via ingestion of contaminated food stuffs and water, and by person to person contact. Viral hepatitis is known to include a group of viral agents with distinctive viral genes and modes of replication, causing hepatitis with differing degrees of severity of hepatic damage through different routes of transmission. In some cases, acute viral hepatitis is clinically diagnosed by well-defined patient symptoms including jaundice, hepatic tenderness and an elevated level of liver transaminases such as aspartate transaminase (AST), alanine transaminase (ALT) and isocitrate dehydrogenase (ISD). In other cases, acute viral hepatitis may be clinically inapparent. The viral agents of hepatitis include hepatitis A virus (HAV), hepatitis B virus (HBV), hepatitis C virus (HCV), hepatitis delta virus (HDV), hepatitis E virus (HEV), Epstein-Barr virus (EBV) and cytomegalovirus (CMV).

Although specific serologic assays available by the late 1960's to screen blood donations for the presence of HBV surface antigen (HBsAg) were successful in reducing the incidence of post-transfusion hepatitis (PTH) in blood recipients, PTH continued to occur at a significant rate. H. J. Alter et al., *Ann. Int. Med.* 77:691–699 (1972); H. J. Alter et al., *Lancet* ii:838–841 (1975). Investigators began to search for a new agent, termed "non-A, non-B hepatitis" (NANBH), that caused viral hepatitis not associated with exposure to viruses previously known to cause hepatitis in man (HAV, HBV, CMV and EBV). See, for example, S. M. Feinstone et al., *New Engl. J. Med.* 292:767–770 (1975); Anonymous editorial, *Lancet* ii:64–65 (1975); F. B. Hollinger in B. N. Fields and D. M. Knipe et al., *Virology*, Raven Press, New York, pp. 2239–2273 (1990).

Several lines of epidemiological and laboratory evidence have suggested the existence of more than one parenterally transmitted NANB agent, including multiple attacks of acute NANBH in intravenous drug users; distinct incubation periods of patients acquiring NANBH post-transfusion; the outcome of cross-challenge chimpanzee experiments; the ultrastructural liver pathology of infected chimpanzees; and the differential resistance of the putative agents to chloroform. J. L. Dienstag, *Gastroenterology* 85:439–462 (1983); J. L. Dienstag, *Gastroenterology* 85:743–768 (1983); F. B. Hollinger et al., *J. Infect. Dis.* 142:400–407 (1980); D. W. Bradley in F. Chisari, ed., *Advances in Hepatitis Research*, Masson, N.Y., pp. 268–280 (1984); and D. W. Bradley et al., *J. Infect. Dis.* 148:254–265 (1983).

A serum sample obtained from a surgeon who had developed acute hepatitis was shown to induce hepatitis when inoculated into tamarins (Saguinus species). Four of four tamarins developed elevated liver enzymes within a few weeks following their inoculation, suggesting that an agent in the surgeon's serum could produce hepatitis in tamarins. Serial passage in various non-human primates demonstrated that this hepatitis was caused by a transmissible agent; filtration studies suggested the agent to be viral in nature. The transmissible agent responsible for these cases of hepatitis in the surgeon and tamarins was termed the "GB agent." F. Deinhardt et al., *J. Exper. Med.* 125:673–688 (1967). F. Deinhardt et al., *J. Exper. Med.*, supra; E. Tabor et al., *J. Med. Virol.* 5:103–108 (1980); R. O. Whittington et al., *Viral and Immunological Diseases in Nonhuman Primates*, Alan R. Liss, Inc., New York, pp. 221–224 (1983).

Although it was suggested that the GB agent may be an agent causing NANBH in humans and that the GB agent was not related to the known NANBH agents studied in various laboratories, no definitive or conclusive studies on the GB agent are known, and no viral agent has been discovered or molecularly characterized. F. Deinhardt et al., *Am. J. Med. Sci.* 270:73–80 (1975); and J. L. Dienstag et al., *Nature* 264:260–261 (1976). See also E. Tabor et al., *J. Med. Virol.*, supra, E. Tabor et al., *J. Infect. Dis.* 140:794–797 (1979); R. O. Whittington et al., supra; and P. Karayiannis et al., *Hepatology* 9:186–192 (1989).

Early studies indicated that the GB agent was unrelated to any known human hepatitis virus. S. M. Feinstone et al., *Science* 182:1026–1028 (1973); P. J. Provost et al., *Proc. Soc. Exp. Biol. Med.* 148:532–539 (1975); J. L. Melnick, *Intervirology* 18:105–106 (1982); A. W. Holmes et al., *Nature* 243:419–420 (1973); and F. Deinhardt et al., *Am. J. Med. Sci.*, supra. However, questions were raised regarding whether the GB agent was a virus which induced hepatitis infection in humans, or a latent tamarin virus activated by the GB serum and once activated, easily passaged to other tamarins, inducing hepatitis in them. Also, a small percentage of marmosets inoculated with GB-positive serum did not develop clinical hepatitis (4 of 52, or 7.6%), suggesting that these animals may have been naturally immune and thus, that the GB agent may be a marmoset virus. W. P. Parks et al., *J. Infect. Dis.* 120:539–547 (1969); W. P. Parks et al., *J. Infect. Dis.* 120:548–559 (1969). Morphological studies have been equivocal, with immune electron microscopy studies in one report indicating that the GB agent formed immune complexes with a size distribution of 20–22 nm and resembling the spherical structure of a parvovirus, while another study reported that immune electron microscopy data obtained from liver homogenates of GB-positive tamarins indicated that aggregates of 34–36 nm with icosahedral symmetry were detected, suggesting that the GB agent was a calici-like virus. See, for example, J. D. Almeida et al., *Nature* 261:608–609 (1976); J. L. Dienstag et al., *Nature*, supra.

Two hepatitis-causing viruses recently have been discovered and reported: HCV, which occurs primarily through parenteral transmission, and HEV, which is transmitted enterically. See, for example, Q. L. Choo et al., *Science* 244:359–362 (1989), G. Kuo et al., *Science* 244:362–364 (1989), E. P. Publication No. 0 318 216 (published May 31, 1989), G. R. Reyes et al., *Science* 247:1335–1339 (1990). HCV is responsible for a majority of PTH ascribed to the NANBH agent(s) and many cases of acute NANBH not acquired by transfusion. Anonymous editorial, *Lancet* 335:1431–1432 (1990); J. L. Dienstag, *Gastroenterology* 99:1177–1180 (1990); and M. J. Alter et al., *JAMA* 264:2231–2235 (1990).

While the detection of HCV antibody in donor samples eliminates 70 to 80% of NANBH infected blood in the blood supply system, the discovery and detection of HCV has not totally prevented the transmission of hepatitis. H. Alter et al., *New Eng. J. Med.* 321:1494–1500 (1989). Recent publications have questioned whether additional hepatitis agents may be responsible for PTH and for community acquired acute and/or chronic hepatitis that is not associated with PTH. For example, of 181 patients monitored in a prospective clinical survey conducted in France from 1988 to 1990, investigators noted a total of 18 cases of PTH. Thirteen of these 18 patients tested negative for anti-HCV antibodies, HBsAg, HBV and HCV nucleic acids. The authors speculated as to the potential importance of a non-A, non-B, non-C agent causing PTH. V. Thiers et al., *J. Hepatology* 18:34–39 (1993). Also, of 1,476 patients monitored in another study conducted in Germany from 1985 to 1988, 22 cases of documented cases of PTH were not related to infection with HBV or HCV. T. Peters et al., *J. Med. Virol.* 39:139–145 (1993).

It would be advantageous to identify and provide materials such as the recombinant antigens disclosed herein derived from and encoding a group of novel and unique viruses causing hepatitis and diagnostics and vaccines that employ these materials. Such materials could greatly enhance the ability of the medical community to more accurately diagnose acute and/or chronic viral hepatitis and could provide a safer blood and organ supply by detecting non-A, non-B and non-C hepatitis in these blood and organ donations.

SUMMARY OF THE INVENTION

The present invention provides a recombinant polypeptide comprising an amino acid sequence or fragment thereof wherein said sequence is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, wherein said recombinant polypeptide is produced from a plasmid selected from the group consisting of pSinRep5/NS5A, pCHO/E2-336, pSFV-ss/E2-336, pSFV-ss/NS3. pCHO/E2-315 and pAcGP67-E2C. Also provided is an antibody directed against at least one hepatitis GB virus (HGBV) epitope, wherein said antibody is produced as a result of the immunization of an individual with a recombinant polypeptide, wherein said recombinant polypeptide is produced from a plasmid selected from the group consisting of pSinRep5/NS5A, pCHO/E2-336, pSFV-ss/E2-336, pSFV-ss/NS3, pCHO/E2-315 and pAcGP67-E2C. The antibody is polyclonal or monoclonal.

The present invention also provides a fusion polypeptide comprising at least one hepatitis GB virus (HGBV) polypeptide or fragment thereof wherein said fusion polypeptide is produced from a plasmid selected from the group consisting of pSinRep5/NS5A, pCHO/E2-336, pSFV-ss/E2-336, pSFV-ss/NS3, pCHO/E2-315 and pAcGP67-E2C.

In addition, an assay kit for determining the presence of hepatitis GB virus (HGBV) antigen or antibody in a test sample comprising a container containing a recombinant polypeptide possessing at least one HGBV epitope present in an HGBV antigen, wherein said polypeptide is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C and is produced from a plasmid selected from the group consisting of pSinRep5/NS5A, pCHO/E2-336, pSFV-ss/E2-336, pSFV-ss/NS3, pCHO/E2-315 and pAcGP67-E2C, is provided. The polypeptide of the assay kit can be attached to a solid phase. Further, the polypeptide can be attached to a signal generating compound which generates a measurable signal. The signal generating compound is selected from the group consisting of an enzyme, a fluorescent compound or a chemiluminescent compound. Another assay kit for determining the presence of hepatitis GB virus (HGBV) antigen or antibody in a test sample is provided, which comprises a container containing an antibody which specifically binds to an HGBV antigen, wherein said antigen comprises an HGBV epitope encoded by a sequence having at least about 60% sequence similarity to a sequence of HGBV and wherein said antibody is produced as a result of the immunization of an individual with a recombinant polypeptide produced from a plasmid selected from the group consisting of pSinRep5/NS5A, pCHO/E2-336, pSFV-ss/E2-336, pSFV-ss/NS3/pCHO/E2-315 and pAcGP67-E2C. The antibody can be attached to a solid phase. Additionally, the antibody can be attached to an indicator reagents comprising a signal generating compound which generates a measurable signal. The signal generating compound is selected from the group consisting of an enzyme, a fluorescent compound or a chemiluminescent compound.

A method for producing a polypeptide containing at least one hepatitis GB virus (HGBV) epitope comprising incubating host cells transformed with an expression vector comprising a sequence encoding a polypeptide characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C wherein said polypeptide is produced from a plasmid selected from the group consisting of pSinRep5/NS5A, pCHO/E2-336, pSFV-ss/E2-336, pSFV-ss/NS3, pCHO/E2-315 and pAcGP67-E2C also is provided by the present invention.

The present invention also provides a method for detecting hepatitis GB virus (HGBV) antigen in a test sample suspected of containing HGBV comprising contacting the test sample with an antibody or fragment thereof which specifically binds to at least one HGBV antigen, for a time and under conditions sufficient to allow the formation of antibody/antigen complexes and detecting said complex containing the antibody wherein said antibody is produced as a result of the immunization of an individual with a recombinant polypeptide produced from a plasmid selected from the group consisting of pSinRep5/NS5A, pCHO/E2-336, pSFV-ss/E2-336, pSFV-ss/NS3, pCHO/E2-315 and pAcGP67-E2C. The antibody, either monoclonal or polyclonal, can be attached to a solid phase. The complex can be attached to an indicator reagent which comprises a signal generating compound which generates a measurable signal. The signal generating compound is selected from the group consisting of an enzyme, a fluorescent compound or a chemiluminescent compound.

A method for detecting hepatitis GB virus (HGBV) antibodies in a test sample suspected of containing said antibodies is also provided, which comprises contacting the test sample with a recombinant polypeptide wherein said polypeptide contains at least one HGBV epitope comprising an amino acid sequence or fragment thereof is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, for a time and under conditions sufficient to allow antigen/antibody complexes to form; and detecting said complexes which contain the probe polypeptide, wherein said polypeptide is produced from a plasmid selected from the group consisting of pSinRep5/NS5A, pCHO/E2-336, pSFV-ss/E2-336, pSFV-ss/NS3, pCHO/E2-315 and pAcGP67-E2C. The probe polypeptide can be attached to a solid phase. The solid phase is selected from the group consisting of beads, microtiter wells, walls of test tube, nitrocellulose strips, magnetic beads and non-magnetic beads. The complexes can be attached to an indicator reagent which comprises a signal generating compound which generates a measurable signal. The signal generating compound is selected from the group consisting of an enzyme, a fluorescent compound or a chemiluminescent compound.

The present invention further provides a vaccine for treatment of hepatitis GB virus (HGBV) infection comprising a pharmacologically effective dose of an immunogenic HGBV recombinant polypeptide or fragment thereof which polypeptide is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, in a pharmaceutically acceptable excipient, wherein said polypeptide is produced from a plasmid selected from the group consisting of pSinRep5/NS5A, pCHO/E2-336, pSFV-ss/E2-336, pSFV-ss/NS3, pCHO/E2-315 and pAcGP67-E2C.

In addition, a method for producing antibodies to hepatitis GB virus (HGBV) comprising administering to an individual an isolated immunogenic recombinant polypeptide or fragment thereof comprising at least one HGBV epitope in an amount sufficient to produce an immune response and wherein said polypeptide is produced from a plasmid selected from the group consisting of pSinRep5/NS5A, pCHO/E2-336, pSFV-ss/E2-336, pSFV-ss/NS3, pCHO/E2-315 and pAcGP67-E2C is provided.

Further, a diagnostic reagent comprising a recombinant polypeptide or fragment thereof derived from hepatitis GB virus (HGBV), wherein said polypeptide or fragment thereof encodes at least one epitope of HGBV and is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, wherein said polypeptide is produced from a plasmid selected from the group consisting of pSinRep5/NS5A, pCHO/E2-336, pSFV-ss/E2-336, pSFV-ss/NS3, pCHO/E2-315 and pAcGP67-E2C is provided.

The present invention moreover provides a method for determining the clearance of hepatitis GB virus (HGBV) from a patient infected HGBV, which comprises contacting a test sample obtained from said patient with a recombinant polypeptide wherein said polypeptide contains at least one HGBV epitope comprising an amino acid sequence or fragment thereof characterized by a positive stranded RNA genome wherein said genome comprises an open reading frame (ORF) encoding a polyprotein wherein said polyprotein comprises an amino acid sequence of HGBV E2 having at least 35% identity to an amino acid sequence selected from the group consisting of HGBV-A, HGBV-B and HGBV-C, for a time and under conditions sufficient to allow antigen/antibody complexes to form, wherein said polypeptide is produced from a plasmid selected from the group consisting of sSinRep5/NS5A, pCHO/E2-336, pSFV-ss/E2-336, sSFV-ss/NS3, pCHOE2-315 and pAcGP67-E2C and detecting said complexes, wherein the presence of said complexes is an indication of the clearance of said HGBV virus from said patient. The recombinant polypeptide can be attached to a solid phase, and the solid phase can be selected from the group consisting of beads, microtiter wells, walls of test tube, nitrocellulose strips, magnetic beads and non-magnetic beads. The complexes can be attached to an indicator reagent comprising a signal generating compound which generates a measurable signal. The signal generating compound is selected from the group consisting of an enzyme, a fluorescent compound or a chemiluminescent compound.

DETAILED DESCRIPTION OF THE INVENTION

Figure 1:
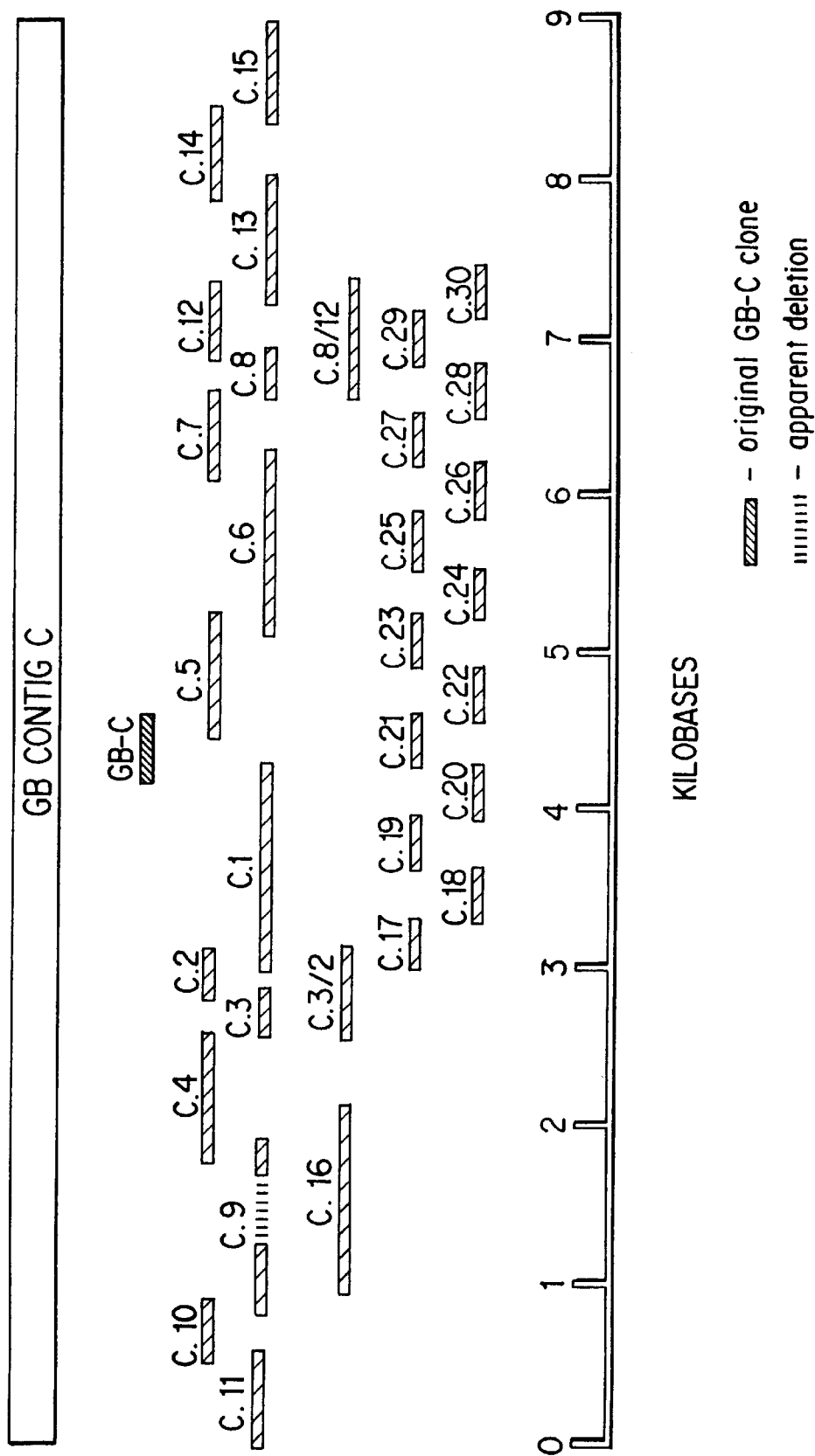
FIG. 1 presents a schematic drawing of the HGBV-C large open reading frame (SEQUENCE I.D. NO. 33) and the expressed PCR products.

The present invention provides characterization of a newly ascertained etiological agents of non-A, non-B, non-C, non-D and non-E hepatitis-causing agents, collectively so-termed "Hepatitis GB Virus," or "HGBV" The present invention provides a method for determining the presence of the HGBV etiological agents, methods for obtaining the nucleic acid of this etiological agents created from infected serum, plasma or liver homogenates from individuals, either humans or tamarins, with HGBV to detect newly synthesized antigens derived from the genome of heretofore unisolated viral agents, and of selecting clones which produced products which are only found in infectious individuals as compared to non-infected individuals.

Polypeptide sequences of HGBV antigens encoded within the HGBV genome(s) permit the production of polypeptides which are useful as standards or reagents in diagnostic tests and/or as components of vaccines. Monoclonal and polyclonal antibodies which have been produced as a result of inoculation of an animal with at least one recombinant antigen disclosed herein directed against at least one epitope contained within these polypeptide sequences, also are useful for diagnostic tests as well as therapeutic agents, for screening of antiviral agents, and for the isolation of the HGBV agent.

According to one aspect of the invention, there will be provided a recombinant polypeptide encoding an epitope of HGBV; a recombinant vector containing any of the above described recombinant polypeptides, and a host cell transformed with these vectors. These recombinant polypeptides may be used alone or in combination, or in conjunction with other substances representing epitopes of HGBV.

In yet another aspect of the invention there will be provided a recombinant expression system comprising an open reading frame (ORF) of DNA derived from an HGBV genome or from HGBV cDNA, wherein the ORF is operably linked to a control sequence compatible with a desired host, a cell transformed with the recombinant expression system, and a polypeptide produced by the transformed cell.

Additional aspects of the present invention include at least one recombinant HGBV polypeptide, at least one recombinant polypeptide comprised of a sequence derived from an HGBV genome or from HGBV cDNA; at least one recombinant polypeptide comprised of an HGBV epitope and at least one fusion polypeptide comprised of an HGBV polypeptide.

The present invention also provides methods for producing a monoclonal antibody which specifically binds to at least one epitope of HGBV; a purified preparation of polyclonal antibodies which specifically bind to at least one HGBV epitope; and methods for using these antibodies, which include diagnostic, prognostic and therapeutic uses.

In still another aspect of the invention there will be provided a particle which immunizes against HGBV infection comprising a non-HGBV polypeptide having an amino acid sequence capable of forming a particle when said sequence is produced in an eukaryotic host, and an HGBV epitope.

A polynucleotide probe for HGBV also will be provided.

The present invention provides kits containing reagents which can be used for the detection of the presence and/or amount of antigen or antibody derived from HGBV, such reagents comprising a recombinant antigen containing an amino acid sequence from HGBV of about 3 to 5 or more amino acids in a suitable container; a reagent for detecting the presence and/or amount of an HGBV antigen comprising an antibody directed against the HGBV antigen to be detected in a suitable container. Other kits for various assay formats also are provided by the present invention as described herein.

Other aspects of the present invention include a polypeptide comprising at least one HGBV epitope attached to a solid phase and an antibody to an HGBV epitope attached to a solid phase. Also included are methods for producing a polypeptide containing an HGBV epitope comprising incubating host cells transformed with an expression vector containing a sequence encoding a polypeptide containing an HGBV epitope under conditions which allow expression of the polypeptide, and a polypeptide containing an HGBV epitope produced by this method.

The present invention also provides assays which utilize the recombinant polypeptides provided by the invention, as well as the antibodies described herein in various formats, any of which may employ a signal generating compound in the assay. Assays which do not utilize signal generating compounds to provide a means of detection also are provided. All of the assays described generally detect either antigen or antibody, or both, and include contacting a test sample with at least one reagent provided herein to form at least one antigen/antibody complex and detecting the presence of the complex. These assays are described in detail herein.

Vaccines for treatment of HGBV infection comprising an immunogenic peptide containing an HGBV epitope, or an inactivated preparation of HGBV, or an attenuated preparation of HGBV, or the use of recombinant vaccines that express HGBV epitope(s) and/or the use of synthetic peptides, also are included in the present invention. An effective vaccine may make use of combinations of these immunogenic peptides (such as, a cocktail of recombinant antigens wherein at least one recombinant antigen is selected from those disclosed herein, synthetic peptides and native viral antigens administered simultaneously or at different times); some of these may be utilized alone and be supplemented with other representations of immunogenic epitopes at later times. Also included in the present invention is a method for producing antibodies to HGBV comprising administering to an individual an isolated immunogenic polypeptide containing an HGBV epitope in an amount sufficient to produce an immune response in the inoculated individual.

The term "Hepatitis GB Virus" or "HGBV", as used herein, collectively denotes a viral species which causes non-A, non-B, non-C, non-D, non-E hepatitis in man, and attenuated strains or defective interfering particles derived therefrom. This may include acute viral hepatitis transmitted by contaminated foodstuffs, drinking water, and the like; hepatitis due to HGBV transmitted via person to person contact (including sexual transmission, respiratory and parenteral routes) or via intraveneous drug use. The methods as described herein will allow the identification of individuals who have acquired HGBV. Individually, the HGBV isolates are specifically referred to as "HGBV-A", "HGBV-B" and "HGBV-C." As described herein, the HGBV genome is comprised of RNA. Analysis of the nucleotide sequence and deduced amino acid sequence of the HGBV reveals that viruses of this group have a genome organization similar to that of the Flaviridae family. Based primarily, but not exclusively, upon similarities in genome organization, the International Committee on the Taxonomy of Viruses has recommended that this family be composed of three genera: Flavivirus, Pestivirus, and the hepatitis C group. Similarity searches at the amino acid level reveal that the hepatitis GB virus subclones have some, albeit low, sequence resemblance to hepatitis C virus. The information provided herein is sufficient to allow classification of other strains of HGBV.

Several lines of evidence demonstrate that HGBV-C is not a genotype of HCV. First, sera containing HGB-C sequences were tested for the presence of HCV antibody. Routine detection of individuals exposed to or infected with HCV relies upon antibody tests which utilize antigens derived from three or more regions from HCV-1. These tests allow detection of antibodies to the known genotypes of HCV (See, for example, Sakamoto et al., *J. Gen. Virol.* 75:1761–1768 (1994) and Stuyver et al., *J. Gen. Virol.* 74:1093–1102 (1993). HCV-specific ELISAs failed to detect sera containing GB-C sequences in six of eight cases. Second, several human sera that were seronegative for HCV antibodies have been shown to be positive for HCV genomic RNA by a highly sensitive RT-PCR assay (Sugitani, *Lancet* 339:1018–1019 (1992). This assay failed to detect HCV RNA in seven of eight sera containing HGB-C sequences (TABLE A). Thus, HGBV-C is not a genotype of HCV based on both serologic and molecular assays.

The alignment of a portion of the predicted translation product of HGB-C within the helicase region with the homologous region of HGBV-A, HGBV-B, HCV-1 and additional members of the Flaviviridae, followed by phylogenetic analysis of the aligned sequences suggests that HGBV-C is more closely related to HGBV-A than to any member of the HCV group. The sequences of HGBV-C and HGBV-A, while exhibiting an evolutionary distance of 0.42, are not as divergent as HGBV-C is from HGBV-B, which shows an evolutionary distance of 0.92. Thus, HGBV-A and HGBV-C may be considered to be members of one subgroup of the GB viruses and GBV-B a member of its own subgroup. The phylogenetic analysis of the helicase sequences from various HCV isolates show that they form a much less diverged group, exhibiting a maximum evolutionary distance of 0.20. A comparison of the HCV group and the HGBV group shows a minimum evolutionary distance between any two sequences from each group of 0.69. The distance values reported hereinabove were used to generate a phylogenic tree. The relatively high degree of divergence among these viruses suggests that the GB viruses are not merely types or subtypes within the hepatitis C group; rather, they constitute their own phylogenetic group (or groups). Phylogenetic analysis using sequence information derived from a small portion of HCV viral genomes has been shown to be an acceptable method for the assignment of new isolates into genotypic groups (Simmonds et al., *Hepatology* 19:1321–1324 (1994). In the current analysis, the use of a 110 amino acid sequence within the helicase gene from representative HCV isolates has properly grouped them into their respective genotypes (Simmonds et al., *J. Gen. Virol.* 75:1053–1061 (1994). Therefore, the evolutionary distances shown, in all likelihood, accurately reflect the high degree of divergence between the GB viruses and the hepatitis C virus.

The techniques for determining amino acid sequence "similarity" and/or "identity" are well-known in the art and include, for example, directly determining the amino acid sequence and comparing it to the sequences provided herein; determining the nucleotide sequence of the genomic material of the putative HGBV (usually via a cDNA intermediate), and determining the amino acid sequence encoded therein, and comparing the corresponding regions. In general, by "identity" is meant the exact match-up of either the nucleotide sequence of HGBV and that of another strain(s) or the amino acid sequence of HGBV and that of another strain(s) at the appropriate place on each genome. Also, in general, by "similarity" is meant the exact match-up of amino acid sequence of HGBV and that of another strain(s) at the appropriate place, where the amino acids are identical or possess similar chemical and/or physical properties such as charge or hydrophobicity. The programs available in the Wisconsin Sequence Analysis Package, Version 8 (available from the Genetics Computer Group, Madison, Wis., 53711), for example, the GAP program, are capable of calculating both the identity and similarity between two polynucleotide or two polypeptide sequences. Other programs for calculating identity and similarity between two sequences are known in the art.

Additionally, the following parameters are applicable, either alone or in combination, in identifying a strain of HGBV-A, HGBV-B or HGBV-C. It is expected that the overall nucleotide sequence identity of the genomes between HGBV-A, HGBV-B or HGBV-C and a strain of one of these hepatitis GB viruses will be about 45% or greater, since it is now believed that the HGBV strains may be genetically related, preferably about 60% or greater, and more preferably, about 80% or greater.

Also, it is expected that the overall sequence identity of the genomes between HGBV-A and a strain of HGBV-A at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-B and a strain of HGBV-B at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-C and a strain of HGBV-C at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence.

The compositions and methods described herein will enable the propagation, identification, detection and isolation of HGBV and its possible strains. Moreover, they also will allow the preparation of diagnostics and vaccines for the possible different strains of HGBV, and will have utility in screening procedures for anti-viral agents. The information will be sufficient to allow a viral taxonomist to identify other strains which fall within the species. We believe that HGBV encodes the sequences that are included herein. Methods for assaying for the presence of these sequences are known in the art and include, for example, amplification methods such as ligase chain reaction (LCR), polymerase chain reaction (PCR) and hybridization. In addition, these sequences contain open reading frames from which an immunogenic viral epitope may be found. This epitope is unique to HGBV when compared to other known hepatitis-causing viruses. The uniqueness of the epitope may be determined by its immunological reactivity with HGBV and lack of immunological reactivity with Hepatitis A, B, C, D and E viruses. Methods for determining immunological reactivity are known in the art and include, for example, radioimmunoassay (RIA), enzyme-linked immunosorbant assay (ELISA), hemagglutination (HA), fluorescence polarization immunoassay (FPIA) and several examples of suitable techniques are described herein.

A polynucleotide "derived from" a designated sequence for example, the HGBV cDNA, or from the HGBV genome, refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., similar to or complementary to, a region of the designated nucleotide sequence. Preferably, the sequence of the region from which the polynucleotide is derived is similar to or complementary to a sequence which is unique to the HGBV genome. Whether or not a sequence is complementary to or similar to a sequence which is unique to an HGBV genome can be determined by techniques known to those skilled in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of HGBV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

A "polypeptide" or "amino acid" sequence derived from a designated nucleic acid sequence or from the HGBV genome refers to a polypeptide having an amino acid sequence identical to that of a polypeptide encoded in the sequence or a portion thereof wherein the portion consists of at least 3 to 5 amino acids, and more preferably at least 8 to 10 amino acids, and even more preferably 15 to 20 amino acids, or which is immunologically identifiable with a polypeptide encoded in the sequence.

A "recombinant polypeptide" as used herein means at least a polypeptide of genomic, semisynthetic or synthetic origin which by virtue of its origin or manipulation is not associated with all or a portion of the polypeptide with which it is associated in nature or in the form of a library and/or is linked to a polynucleotide other than that to which it is linked in nature. A recombinant or derived polypeptide is not necessarily translated from a designated nucleic acid sequence of HGBV or from an HGBV genome. It also may be generated in any manner, including chemical synthesis or expression of a recombinant expression system, or isolation from mutated HGBV.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

"HGBV containing a sequence corresponding to a cDNA" means that the HGBV contains a polynucleotide sequence which is similar to or complementary to a sequence in the designated DNA. The degree of similarity or complementarity to the cDNA will be approximately 50% or greater, will preferably be at least about 70%, and even more preferably will be at least about 90%. The sequence which corresponds will be at least about 70 nucleotides, preferably at least about 80 nucleotides, and even more preferably at least about 90 nucleotides in length. The correspondence between the HGBV and the cDNA can be determined by methods known in the art, and include, for example, a direct comparison of the sequenced material with the cDNAs described, or hybridization and digestion with single strand nucleases, followed by size determination of the digested fragments.

"Purified viral polynucleotide" refers to an HGBV genome or fragment thereof which is essentially free, i.e., contains less than about 50%, preferably less than about 70%, and even more preferably, less than about 90% of polypeptides with which the viral polynucleotide is naturally associated. Techniques for purifying viral polynucleotides are well known in the art and include, for example, disruption of the particle with a chaotropic agent, and separation of the polynucleotide(s) and polypeptides by ion-exchange chromatography, affinity chromatography, and sedimentation according to density. Thus, "purified viral polypeptide" means an HGBV polypeptide or fragment thereof which is essentially free, that is, contains less than about 50%, preferably less than about 70%, and even more preferably, less than about 90% of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term, however, is not intended to refer to post-expression modifications of the polypeptide, for example, glycosylations, acetylations, phosphorylations and the like.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transfer DNA, and include the original progeny of the original cell which has been transfected.

As used herein "replicon" means any genetic element, such as a plasmid, a chromosome or a virus, that behaves as an autonomous unit of polynucleotide replication within a cell. That is, it is capable of replication under its own control.

A "vector" is a replicon in which another polynucleotide segment is attached, such as to bring about the replication and/or expression of the attached segment.

The term "control sequence refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s), usually HGBV proteins. Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an HGBV epitope" means naturally occurring HGBV polypeptides or fragments thereof, as well as polypeptides prepared by other means, for example, chemical synthesis or the expression of the polypeptide in a recombinant organism.

The term "transformation" refers to the insertion of an exogenous polynucleotide into a host cell, irrespective of the method used for the insertion. For example, direct uptake, transduction, or f-mating are included. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to tamarins and humans.

The term "plus strand" (or "+") as used herein denotes a nucleic acid that contains the sequence that encodes the polypeptide. The term "minus strand" (or "−") denotes a nucleic acid that contains a sequence that is complementary to that of the "plus" strand.

"Positive stranded genome" of a virus denotes that the genome, whether RNA or DNA, is single-stranded and which encodes a viral polypeptide(s).

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens.

After preparing the recombinant antigen as described, the recombinant antigen can be used to develop unique assays as described herein to detect either the presence of antigen or antibody to HGBV. These compositions also can be used to develop monoclonal and/or polyclonal antibodies with a specific recombinant antigen which specifically bind to the immunological epitope of HGBV which is desired by the routineer. Also, it is contemplated that at least one recombinant antigen of the invention can be used to develop vaccines by following methods known in the art.

It is contemplated that the reagent employed for the assay can be provided in the form of a test kit with one or more containers such as vials or bottles, with each container containing a separate reagent such as a monoclonal antibody, or a cocktail of monoclonal antibodies, or a recombinant antigen employed in the assay. Other components such as buffers, controls, and the like, known to those of ordinary skill in art, may be included in such test kits.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules. The term "hapten", as used herein, refers to a partial antigen or non-protein binding member which is capable of binding to an antibody, but which is not capable of eliciting antibody formation unless coupled to a carrier protein.

A "capture reagent", as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal generating compound" (label) which is capable of generating and generates a measurable signal detectable by external means conjugated (attached) to a specific binding member for HGBV. "Specific binding member" as used herein means a member of a specific binding pair. That is, two different molecules where one of the molecules through chemical or physical means specifically binds to the second molecule. In addition to being an antibody member of a specific binding pair for HGBV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HGBV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, Duracytes® (derivatized red blood cells, available from Abbott Laboratories, Abbott Park, Ill.), and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracyte® and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. All of these materials may be used in suitable shapes, such as films, sheets, or plates, or they may be coated onto or bonded or laminated to appropriate inert carriers, such as paper, glass, plastic films, or fabrics.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0326100 and U.S. patent application Ser. No. 375,029 (EP publication no. 0406473), can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in pending U.S. patent applications Ser. Nos. 425,651 and 425,643, which correspond to published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries described by pending U.S. patent applications Ser. No. 150,278, filed Jan. 29, 1988, and Ser. No. 375,029, filed Jul. 7, 1989. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Various other assay formats may be used, including "sandwich" immunoassays and probe assays. For example, the monoclonal antibodies of the present invention can be employed in various assay systems to determine the presence, if any, of HGBV proteins in a test sample. Fragments of these monoclonal antibodies provided also may be used. For example, in a first assay format, a polyclonal or monoclonal anti-HGBV antibody or fragment thereof, or a combination of these antibodies, which has been coated on a solid phase, is contacted with a test sample which may contain HGBV proteins, to form a mixture. This mixture is incubated for a time and under conditions sufficient to form antigen/antibody complexes. Then, an indicator reagent comprising a monoclonal or a polyclonal antibody or a fragment thereof, which specifically binds to an HGBV region, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of HGBV antigen present in the test sample and captured on the solid phase, if any, is determined by detecting the measurable signal generated by the signal generating compound. The amount of HGBV antigen present in the test sample is proportional to the signal generated.

Alternatively, a polyclonal or monoclonal anti-HGBV antibody or fragment thereof, or a combination of these antibodies which is bound to a solid support, the test sample and an indicator reagent comprising a monoclonal or polyclonal antibody or fragments thereof, which specifically binds to HGBV antigen, or a combination of these antibodies to which a signal generating compound is attached, are contacted to form a mixture. This mixture is incubated for a time and under conditions sufficient to form antibody/antigen/antibody complexes. The presence, if any, of HGBV proteins present in the test sample and captured on the solid phase is determined by detecting the measurable signal generated by the signal generating compound. The amount of HGBV proteins present in the test sample is proportional to the signal generated.

In another alternate assay format, one or a combination of at least two monoclonal antibodies of the invention can be employed as a competitive probe for the detection of antibodies to HGBV protein. For example, HGBV proteins such as the recombinant antigens disclosed herein, either alone or in combination, can be coated on a solid phase. A test sample suspected of containing antibody to HGBV antigen then is incubated with an indicator reagent comprising a signal generating compound and at least one monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANB, non-C, non-D, non-E hepatitis test sample indicates the presence of anti-HGBV antibody in the test sample.

In yet another detection method, each of the monoclonal or polyclonal antibodies of the present invention can be employed in the detection of HGBV antigens in fixed tissue sections, as well as fixed cells by immunohistochemical analysis. Cytochemical analysis wherein these antibodies are labeled directly (fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific HGBV proteins from cell cultures, or biological tissues such as blood and liver such as to purify recombinant and native viral HGBV antigens and proteins.

The monoclonal antibodies of the invention can also be used for the generation of chimeric antibodies for therapeutic use, or other similar applications.

The monoclonal antibodies or fragments thereof can be provided individually to detect HGBV antigens. Combinations of the monoclonal antibodies (and fragments thereof) provided herein also may be used together as components in a mixture or "cocktail" of at least one anti-HGBV antibody of the invention with antibodies to other HGBV regions, each having different binding specificities. Thus, this cocktail can include the monoclonal antibodies of the invention which are directed to HGBV proteins and other monoclonal antibodies to other antigenic determinants of the HGBV genome.

The polyclonal antibody or fragment thereof which can be used in the assay formats should specifically bind to a specific HGBV region or other HGBV proteins used in the assay. The polyclonal antibody used preferably is of mammalian origin; human, goat, rabbit or sheep anti-HGBV polyclonal antibody can be used. Most preferably, the polyclonal antibody is rabbit polyclonal anti-HGBV antibody. The polyclonal antibodies used in the assays can be used either alone or as a cocktail of polyclonal antibodies. Since the cocktails used in the assay formats are comprised of either monoclonal antibodies or polyclonal antibodies having different HGBV specificity, they would be useful for diagnosis, evaluation and prognosis of HGBV infection, as well as for studying HGBV protein differentiation and specificity.

It is contemplated and within the scope of the present invention that the HGBV group of viruses may be detectable in assays by use of a recombinant antigen as well as by use of a synthetic peptide or native peptide, which contain an amino acid sequence that is common to all HGBV viruses. It also is within the scope of the present invention that different synthetic, recombinant or native peptides identifying different epitopes from HGBV-A, HGBV-B, HGBV-C, or yet other HGBV viruses, can be used in assay formats. In the later case, these can be coated onto one solid phase, or each separate peptide may be coated on separate solid phases, such as microparticles, and then combined to form a mixture of peptides which can be later used in assays. Such variations of assay formats are known to those of ordinary skill in the art and are discussed hereinbelow.

In another assay format, the presence of antibody and/or antigen to HGBV can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from human expression systems may be utilized as well as monoclonal antibodies produced from the proteins derived from the mammalian expression systems as disclosed herein. Such assay systems are described in greater detail in pending U.S. patent application Ser. No. 07/574,821 entitled Simultaneous Assay for Detecting One Or More Analytes, which corresponds to EP Publication No. 0473065.

In yet other assay formats, the recombinant antigens disclosed herein may be utilized to detect the presence of anti-HGBV in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of HGBV antibody. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as $E.\ coli$ is used as a capture antigen on a solid phase, a test sample is added to the so-prepared solid phase, and a recombinant protein derived from a different source (i.e., non-$E.\ coli$) is utilized as a part of an indicator reagent. Likewise, combinations of a recombinant antigen on a solid phase and synthetic peptide in the indicator phase also are possible. Any assay format which utilizes an antigen specific for HGBV from a first source as the capture antigen and an antigen specific for HGBV from a different second source are contemplated. Thus, various combinations of recombinant antigens, as well as the use of synthetic peptides, purified viral proteins, and the like, are within the scope of this invention. Assays such as this and others are described in U.S. Pat. No. 5,254,458, which enjoys common ownership and is incorporated herein by reference.

Other assay systems which utilize an antibody (polyclonal, monoclonal or naturally-occurring) which specifically binds HGBV viral particles or sub-viral particles housing the viral genome (or fragments thereof) by virtue of a contact between the specific antibody and the viral protein (peptide, etc.). This captured particle then can be analyzed by methods such as LCR or PCR to determine whether the viral genome is present in the test sample. Test samples which can be assayed according to this method include blood, liver, sputum, urine, fecal material, saliva, and the like. The advantage of utilizing such an antigen capture amplification method is that it can separate the viral genome from other molecules in the test specimen by use of a specific antibody. Such a method has been described in pending U.S. patent application Ser. No. 08/141,429.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

MATERIALS AND METHODS

General Techniques

Conventional and well-known techniques and methods in the fields of molecular biology, microbiology, recombinant DNA and immunology are employed in the practice of the invention unless otherwise noted. Such techniques are explained and detailed in the literature. See, for example, J. Sambrook et al., *Molecular Cloning: A Laboratory Manual*, 2nd edition, Cold Spring Harbor Press, Cold Spring Harbor, N.Y. (1989); D. N. Glover, ed., *DNA Cloning, Volumes I and II* (1985); M. J. Gait ed., *Oligonucleotide Synthesis*, (1984); B. D. Hames et al., eds., *Nucleic Acid Hybridization*, (1984); B. D. Hames et al., eds., *Transcription and Translation*, (1984); R. L Freshney ed., *Animal Cell Culture*, (1986); *Immobilized Cells and Enzymes*, IRL Press (1986); B. Perbal, *A Practical Guide to Molecular Cloning*, (1984); the series, *Methods in Enzymology*, Academic Press, Inc., Orlando, Fla.; J. H. Miller et al., eds., *Gene Transfer Vectors For Mammalian Cells*, Cold Spring Harbor Laboratory, Cold Spring Harbor, N.Y. (1987); Wu et al., eds., *Methods in Enzymology*, Vol. 154 and 155; Mayer et al., eds., *Immunological Methods In Cell and Molecular Biology*, Academic Press, London (1987); Scopes, *Protein Purification: Principles and Practice,* 2nd ed., Springer-Verlag, N.Y.; and D. Weir et al., eds., *Handbook Of Experimental Immunology*, Volumes I–IV (1986); N. Lisitisyn et al., *Science* 259:946–951 (1993).

The reagents and methods of the present invention are made possible by the provision of a family of closely related nucleotide sequences, isolated by representational difference analysis modified as described herein, present in the plasma, serum or liver homogenate of an HGBV infected individual, either tamarin or human. This family of nucleotide sequences is not of human or tamarin origin, since it hybridizes to neither human nor tamarin genomic DNA from uninfected individuals, since nucleotides of this family of sequences are present only in liver (or liver homogenates), plasma or serum of individuals infected with HGBV, and since the sequence is not present in GenBank®. In addition, the family of sequences shows no significant identity at the nucleic acid level to sequences contained within the HAV, HBV, HCV, HDV and HEV genome, and low level identity, considered not significant, as translation products. Infectious sera, plasma or liver homogenates from HGBV infected humans contain these polynucleotide sequences, whereas sera, plasma or liver homogenates from non-infected humans do not contain these sequences. Northern blot analysis of infected liver with some of these polynucleotide sequences demonstrate that they are derived from a large RNA transcript similar in size to a viral genome. Sera, plasma or liver homogenates from HGBV-infected humans contain antibodies which bind to this polypeptide, whereas sera, plasma or liver homogenates from non-infected humans do not contain antibodies to this polypeptide; these antibodies are induced in individuals following acute non-A, non-B, non-C, non-D and non-E infection. By these criteria, it is believed that the sequence is a viral sequence, wherein the virus causes or is associated with non-A, non-B, non-C, non-D and non-E hepatitis.

The recombinant antigens disclosed herein are useful in diagnosing non-A, non-B, non-C, non-D, non-E hepatitis due to HGBV infections, and in screening blood donors, donated blood, blood products and individuals for infection. The family of polypeptides derived from these sequences, as well as antibodies directed against these polypeptides, also are useful in the isolation and identification of the HGBV etiological agent(s). For example, antibodies directed against HGBV epitopes contained in polypeptides derived from the nucleic acid sequences may be used in methods based upon affinity chromatography to isolate the virus. Alternatively, the antibodies can be used to identify viral particles isolated by other techniques. The viral antigens and the genomic material within the isolated viral particles then may be further characterized.

The information obtained from further sequencing of the HGBV genome(s), as well as from further characterization of the HGBV antigens and characterization of the genome enables the design and synthesis of additional probes and polypeptides and antibodies which may be used for diagnosis, prevention and therapy of HGBV induced non-A, non-B, non-C non-D, non-E hepatitis, and for screening of infected blood and blood-related products.

Deposit of Strains

Strains replicated (clones 2, 4, 10, 16, 18, 23 and 50) from the HGBV nucleic acid sequence library have been deposited at the American Type Culture Collection, 12301 Parklawn Drive, Rockville, Md. 20852, as of Feb. 10, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone 2 was accorded A.T.C.C. Deposit No. 69556; Clone 4 was accorded A.T.C.C. Deposit No. 69557; Clone 10 was accorded A.T.C.C. Deposit No. 69558; Clone 16 was accorded A.T.C.C. Deposit No. 69559; Clone 18 was accorded A.T.C.C. Deposit No. 69560; Clone 23 was accorded A.T.C.C. Deposit No. 69561; and Clone 50 was accorded A.T.C.C. Deposit No. 69562.

Strains replicated (clones 11, 13, 48 and 119) from the HGBV nucleic acid sequence library have been deposited at the American Type Culture Collection, 12301 Parklawn Drive, Rockville, Md. 20852, as of Apr. 29, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone 11 was accorded A.T.C.C. Deposit No. No. 69613; Clone 13 was accorded A.T.C.C. Deposit No. 69611; Clone 48 was accorded A.T.C.C. Deposit No. 69610; and Clone 119 was accorded A.T.C.C. Deposit No. 69612.

Additional strains (clones 4B1.1, 66-3A1.49, 70-3A1.37 and 78-1C1.17) from the HGBV nucleic acid sequence library have been deposited at the American Type Culture Collection, 12301 Parklawn Drive, Rockville, Md. 20852, as of Jul. 28, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone 4-B1.1 was accorded A.T.C.C. Deposit No. No. 69666; Clone 66-3A1.49 was accorded A.T.C.C. Deposit No. 69665; Clone 70-3A1.37 was accorded A.T.C.C. Deposit No. 69664; and Clone 78-1C1.17 was accorded A.T.C.C. Deposit No. 69663.

Clone pHGBV-C clone #1 was deposited at the American Type Culture Collection, 12301 Parklawn Drive, Rockville, Md. 20852 as of Nov. 8, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. pHGBV-C clone #1 was accorded A.T.C.C. Deposit No. 69711. The HGBV cDNA sequences in all of the deposited materials are incorporated herein by reference.

Preparation of Viral Polypeptides and Fragments

The availability of nucleic acid sequences permits the construction of expression vectors encoding antigenically active regions of the polypeptide encoded in either strand. These antigenically active regions may be derived from structural regions of the virus, including, for example, envelope (coat) or core antigens, in addition to nonstructural regions of the virus, including, for example, polynucleotide binding proteins, polynucleotide polymerase(s), and other viral proteins necessary for replication and/or assembly of the viral particle. Fragments encoding the desired polypeptides are derived from the genomic or cDNA clones using conventional restriction digestion or by synthetic methods, and are ligated into vectors which may, for example, contain portions of fusion sequences such as beta-galactosidase (b-gal) or superoxide dismutase (SOD) or CMP-KDO synthetase (CKS). Methods and vectors which are useful for the production of polypeptides which contain fusion sequences of SOD are described in EPO 0196056, published Oct. 1, 1986, and those of CKS are described in EPO Publication No. 0331961, published Sep. 13, 1989. Any desired portion of the nucleic acid sequence containing an open reading frame, in either sense strand, can be obtained as a recombinant protein, such as a mature or fusion protein; alternatively, a polypeptide encoded in the HGBV genome or cDNA can be provided by chemical synthesis.

An additional expression system useful for producing the recombinant antigens disclosed herein utilizes the lambda pL vector system. This expression system has the following features: (1) a strong lambda pL promoter, (2) a strong three-frame translation terminator rrnBt1, and (3) translation starts at an ATG codon, eight base pairs from the ribosome binding site located within an accessible Nco1 restriction site.

The nucleic acid sequence encoding the desired polypeptide, whether in fused or mature form, and whether or not containing a signal sequence to permit secretion, may be ligated into expression vectors suitable for any convenient host. Both eukaryotic and prokaryotic host systems are used in the art to form recombinant proteins, and some of these are listed herein. The polypeptide then is isolated from lysed cells or from the culture medium and purified to the extent needed for its intended use. Purification can be performed by techniques known in the art, and include salt fractionation, chromatography on ion exchange resins, affinity chromatography, centrifugation, among others. Such polypeptides may be used as diagnostic reagents, or for passive immunotherapy. In addition, antibodies to these polypeptides are useful for isolating and identifying HGBV particles. The HGBV antigens also may be isolated from HGBV virions. These virions can be grown in HGBV infected cells in tissue culture, or in an infected individual.

Preparation of Antigenic Polypeptides and Conjugation With Solid Phase

An antigenic region or fragment of a polypeptide generally is relatively small, usually about 8 to 10 amino acids or less in length. Fragments of as few as 5 amino acids may characterize an antigenic region. These segments may correspond to regions of HGBV antigen. By using the HGBV genomic or cDNA sequences as a basis, nucleic acid sequences encoding short segments of HGBV polypeptides can be expressed recombinantly either as fusion proteins or as isolated polypeptides. These short amino acid sequences also can be obtained by chemical synthesis. The small chemically synthesized polypeptides may be linked to a suitable carrier molecule when the synthesized polypeptide provided is correctly configured to provide the correct epitope but too small to be antigenic. Linking methods are known in the art and include but are not limited to using N-succinimidyl-3-(2-pyrdylthio)propionate (SPDP) and succinimidyl 4-(N-maleimidomethyl)cyclohexane-1-carboxylate (SMCC). Polypeptides lacking sulfhydryl groups can be modified by adding a cysteine residue. These reagents create a disulfide linkage between themselves and peptide cysteine residues on one protein and an amide linkage through the epsilon-amino on a lysine, or other free amino group in the other. A variety of such disulfide/amide-forming agents are known. Other bifunctional coupling agents form a thioester rather than a disulfide linkage. Many of these thio-ether-forming agents are commercially available and are known to those of ordinary skill in the art. The carboxyl groups can be activated by combining them with succinimide or 1-hydroxyl-2-nitro-4-sulfonic acid, sodium salt. Any carrier which does not itself induce the production of antibodies harmful to the host can be used. Suitable carriers include proteins, polysaccharides such as latex functionalized sepharose, agarose, cellulose, cellulose beads, polymeric amino acids such as polyglutamic acid, polylysine, amino acid copolymers and inactive virus particles, among others. Examples of protein substrates include serum albumins, keyhole limpet hemocyanin, immunoglobulin molecules, thyroglobulin, ovalbumin, tetanus toxoid, and yet other proteins known to those skilled in the art.

Preparation of Hybrid Particle Immunogens Containing HGBV Epitopes

The immunogenicity of HGBV epitopes also may be enhanced by preparing them in mammalian or yeast systems fused with or assembled with particle-forming proteins such as those associated with HBV surface antigen. Constructs wherein the HGBV epitope is linked directly to the particle-forming protein coding sequences produce hybrids which are immunogenic with respect to the HGBV epitope. In addition, all of the vectors prepared include epitopes specific for HGBV, having varying degrees of immunogenicity. Particles constructed from particle forming protein which include HGBV sequences are immunogenic with respect to HGBV and HBV.

Hepatitis B surface antigen has been determined to be formed and assembled into particles in *S. cerevisiae* and mammalian cells; the formation of these particles has been reported to enhance the immunogenicity of the monomer subunit. P. Valenzuela et al., *Nature* 298:334 (1982); P. Valenzuela et al., in I. Millman et al., eds., *Hepatitis B*, Plenum Press, pp. 225–236 (1984). The constructs may include immunodominant epitopes of HBsAg. Such constructs have been reported expressible in yeast, and hybrids including heterologous viral sequences for yeast expression have been disclosed. See, for example, EPO 174, 444 and EPO 174,261. These constructs also have been reported capable of being expressed in mammalian cells such as Chinese hamster ovary (CHO) cells. Michelle et al., *International Symposium on Viral Hepatitis*, 1984. In HGBV, portions of the particle-forming protein coding sequence may be replaced with codons encoding an HGBV epitope. In this replacement, regions that are not required to mediate the aggregation of the units to form immunogenic particles in yeast or mammals can be deleted, thus eliminating additional HGBV antigenic sites from competition with the HGBV epitope.

Vaccine Preparation

Vaccines may be prepared from one or more immunogenic polypeptides or nucleic acids derived from HGBV nucleic acid sequences or from the HGBV genome to which they correspond. Vaccines may comprise recombinant polypeptides containing epitope(s) of HGBV. These polypeptides may be expressed in bacteria, yeast or mammalian cells, or alternatively may be isolated from viral preparations. It also is anticipated that various structural proteins may contain epitopes of HGBV which give rise to protective anti-HGBV antibodies. Synthetic peptides therefore also can be utilized when preparing these vaccines. Thus, polypeptides containing at least one epitope of HGBV may be used, either singly or in combinations, in HGBV vaccines. It also is contemplated that nonstructural proteins as well as structural proteins may provide protection against viral pathogenicity, even if they do not cause the production of neutralizing antibodies.

Considering the above, multivalent vaccines against HGBV may comprise one or more structural proteins, and/or one or more nonstructural proteins. These vaccines may be comprised of, for example, recombinant HGBV polypeptides and/or polypeptides isolated from the virions and/or synthetic peptides. These immunogenic epitopes can be used in combinations, i.e., as a mixture of recombinant proteins, synthetic peptides and/or polypeptides isolated from the virion; these may be administered at the same or different time. Additionally, it may be possible to use inactivated HGBV in vaccines. Such inactivation may be preparation of viral lysates, or by other means known in the art to cause inactivation of hepatitis-like viruses, for example, treatment with organic solvents or detergents, or treatment with formalin. Attenuated HGBV strain preparation also is disclosed in the present invention. It is contemplated that some of the proteins in HGBV may cross-react with other known viruses, and thus that shared epitopes may exist between HGBV and other viruses which would then give rise to protective antibodies against one or more of the disorders caused by these pathogenic agents. It is contemplated that it may be possible to design multiple purpose vaccines based upon this belief.

The preparation of vaccines which contain at least one immunogenic peptide as an active ingredient is known to one skilled in the art. Typically, such vaccines are prepared as injectables, either as liquid solutions or suspensions; solid forms suitable for solution in or suspension in liquid prior to injection also may be prepared. The preparation may be emulsified or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), and RIBI (MPL+TDM+CWS) in a 2% squalene/Tween-80® emulsion. The effectiveness of an adjuvant may be determined by measuring the amount of antibodies directed against an immunogenic polypeptide containing an HGBV antigenic sequence resulting from administration of this polypeptide in vaccines which also are comprised of the various adjuvants.

The vaccines usually are administered by intraveneous or intramuscular injection. Additional formulations which are suitable for other modes of administration include suppositories and, in some cases, oral formulations. For suppositories, traditional binders and carriers may include but are not limited to polyalkylene glycols or triglycerides. Such suppositories may be formed from mixtures containing the active ingredient in the range of about 0.5% to about 10%, preferably, about 1% to about 2%. Oral formulation include such normally employed excipients as, for example pharmaceutical grades of mannitol, lactose, starch, magnesium stearate, sodium saccharine, cellulose, magnesium carbonate and the like. These compositions may take the form of solutions, suspensions, tablets, pills, capsules, sustained release formulations or powders and contain about 10% to about 95% of active ingredient, preferably about 25% to about 70%.

The proteins used in the vaccine may be formulated into the vaccine as neutral or salt forms. Pharmaceutically acceptable salts such as acid addition salts (formed with free amino groups of the peptide) and which are formed with inorganic acids such as hydrochloric or phosphoric acids, or such organic acids such as acetic, oxalic, tartaric, maleic, and others known to those skilled in the art. Salts formed with the free carboxyl groups also may be derived from inorganic bases such as sodium, potassium, ammonium, calcium or ferric hydroxides and the like, and such organic bases such as isopropylamine, trimethylamine, 2-ethylamino ethanol, histidine procaine, and others known to those skilled in the art.

Vaccines are administered in a way compatible with the dosage formulation, and in such amounts as will be prophylactically and/or therapeutically effective. The quantity to be administered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reinforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic HGBV antigen(s) may be administered in conjunction with other immunoregulatory agents, for example, with immune globulins.

Preparation of Antibodies Against HGBV Epitopes

The immunogenic peptides prepared as described herein are used to produce antibodies, either polyclonal or monoclonal. When preparing polyclonal antibodies, a selected mammal (for example, a mouse, rabbit, goat, horse or the like) is immunized with an immunogenic polypeptide bearing at least one HGBV epitope. Serum from the immunized animal is collected after an appropriate incubation period and treated according to known procedures. If serum containing polyclonal antibodies to an HGBV epitope contains antibodies to other antigens, the polyclonal antibodies can be purified by, for example, immunoaffinity chromatography. Techniques for producing and processing polyclonal antibodies are known in the art and are described in, among others, Mayer and Walker, eds., *Immunochemical Methods In Cell and Molecular Biology*, Academic Press, London (1987). Polyclonal antibodies also may be obtained from a mammal previously infected with HGBV. An example of a method for purifying antibodies to HGBV epitopes from serum of an individual infected with HGBV using affinity chromatography is provided herein.

Monoclonal antibodies directed against HGBV epitopes also can be produced by one skilled in the art. The general methodology for producing such antibodies is well-known and has been described in, for example, Kohler and Milstein, *Nature* 256:494 (1975) and reviewed in J. G. R. Hurrel, ed., *Monoclonal Hybridoma Antibodies: Techniques and Applications*, CRC Press Inc., Boco Raton, Fla. (1982), as well as that taught by L. T. Mimms et al., *Virology* 176:604–619 (1990). Immortal antibody-producing cell lines can be created by cell fusion, and also by other techniques such as direct transformation of B lymphocytes with oncogenic DNA, or transfection with Epstein-Barr virus. See also, M. Schreier et al., Hybridoma Techniques, Scopes (1980) Protein Purification, Principles and Practice, 2nd Edition, Springer-Verlag, New York (1984); Hammerling et al., Monoclonal Antibodies and T-Cell Hybridomas (1981); Kennet et al., Monoclonal Antibodies (1980). Examples of uses and techniques of monoclonal antibodies are disclosed in U.S. patent applications Ser. Nos. 748,292; 748,563; 610,175, 648,473; 648,477; and 648,475.

Monoclonal and polyclonal antibodies thus developed, directed against HGBV epitopes, are useful in diagnostic and prognostic applications, and also, those which are neutralizing are useful in passive immunotherapy. Monoclonal antibodies especially can be used to produce anti-idiotype antibodies. These anti-idiotype antibodies are immunoglobulins which carry an "internal image" of the antigen of the infectious agent against which protection is desired. See, for example, A. Nisonoff et al., *Clin. Immunol. Immunopath.* 21:397–406 (1981), and Dreesman et al., *J. Infect. Dis.* 151:761 (1985). Techniques for raising such idiotype antibodies are known in the art and exemplified, for example, in Grych et al., *Nature* 316:74 (1985); MacNamara et al., *Science* 226:1325 (1984); and Uytdehaag et al., *J. Immunol.* 134:1225 (1985). These anti-idiotypic antibodies also may be useful for treatment of HGBV infection, as well as for elucidation of the immunogenic regions of HGBV antigens.

Immunoassay and Diagnostic Kits

Both the polypeptides which react immunologically with serum containing HGBV antibodies and composites thereof, and the antibodies raised against the HGBV specific epitopes in these polypeptides are useful in immunoassays to detect the presence of HGBV antibodies, or the presence of the virus and/or viral antigens in biological test samples. The design of these immunoassays is subject to variation, and a variety of these are known in the art; a variety of these have been described herein. The immunoassay may utilize one viral antigen, such as a polypeptide derived from any clone-containing HGBV nucleic acid sequence, or from the composite nucleic acid sequences derived from the HGBV nucleic acid sequences in these clones, or from the HGBV genome from which the nucleic acid sequences in these clones is derived. Or, the immunoassay may use a combination of viral antigens derived from these sources. It may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilize solid phases. Examples of assays which utilize labels as the signal generating compound and those labels are described herein. Signals also may be amplified by using biotin and avidin, enzyme labels or biotin anti-biotin systems, such as that described in pending U.S. patent application Ser. Nos. 608,849; 070,647; 418,981; and 687,785 and as known in the art. Recombinant polypeptides which include epitopes from immunodominant regions of HGBV may be useful for the detection of viral antibodies in biological test samples of infected individuals. It also is contemplated that GBV antibodies may be useful in discriminating acute from non-acute infections. Kits suitable for immunodiagnosis and containing the appropriate reagents are constructed by packaging the appropriate materials, including the polypeptides of the invention containing HGBV epitopes or antibodies directed against HGBV epitopes in suitable containers, along with the remaining reagents and materials required for the conduct of the assay, as well as suitable assay instructions.

Assay formats can be designed which utilize the recombinant proteins detailed herein, and although we describe and detail CKS-fused proteins, it also is contemplated and within the scope of the present invention that other expression systems, such as pL, superoxide dismutase (SOD), and others, can be used in the present invention to generate fusion proteins capable of use in a variety of ways, including as antigens in immunoassays, immunogens for antibody production, and the like. In an assay format to detect the presence of antibody against a specific analyte (for example, an infectious agent such as a virus) in a human test sample, the human test sample is contacted and incubated with a solid phase coated with at least one recombinant protein (polypeptide). If antibodies are present in the test sample, they will form a complex with the antigenic polypeptide and become affixed to the solid phase. After the complex has formed, unbound materials and reagents are removed by washing the solid phase. The complex is reacted with an indicator reagent and allowed to incubate for a time and under conditions for second complexes to form. The presence of antibody in the test sample to the CKS recombinant polypeptide(s) is determined by detecting the signal generated. Signal generated above a cut-off value is indicative of antibody to the analyte present in the test sample. With many indicator reagents, such as enzymes, the amount of antibody present is proportional to the signal generated. Depending upon the type of test sample, it may be diluted with a suitable buffer reagent, concentrated, or contacted with the solid phase without any manipulation ("neat"). For example, it usually is preferred to test serum or plasma samples which previously have been diluted, or concentrate specimens such as urine, in order to determine the presence and/or amount of antibody present.

In addition, more than one recombinant protein can be used in the assay format just described to test for the presence of antibody against a specific infectious agent by utilizing CKS fusion proteins against various antigenic epitopes of the viral genome of the infectious agent under study. Thus, it may be preferred to use recombinant polypeptides which contain epitopes within a specific viral antigenic region as well as epitopes from other antigenic regions from the viral genome to provide assays which have increased sensitivity and perhaps greater specificity than using a polypeptide from one epitope. Such an assay can be utilized as a confirmatory assay. In this particular assay format, a known amount of test sample is contacted with (a) known amount(s) of at least one solid support coated with at least one recombinant protein for a time and under conditions sufficient to form recombinant protein/antibody complexes. The complexes are contacted with known amount(s) of appropriate indicator reagent(s)s for a time and under suitable conditions for a reaction to occur, wherein the resultant signal generated is compared to a negative test sample in order to determine the presence of antibody to the analyte in the test sample. It further is contemplated that, when using certain solid phases such as microparticles, each recombinant protein utilized in the assay can be attached to a separate microparticle, and a mixture of these microparticles made by combining the various coated microparticles, which can be optimized for each assay.

Variations to the above-described assay formats include the incorporation of CKS- recombinant proteins of different analytes attached to the same or to different solid phases for the detection of the presence of antibody to either analyte (for example, CKS- recombinant proteins specific for certain antigenic regions of one infective agent coated on the same or different solid phase with CKS- recombinant proteins specific for certain antigenic region(s) of a different infective agent, to detect the presence of either (or both) infective agents.

In yet another assay format, CKS recombinant proteins containing antigenic epitopes are useful in competitive assays such as neutralization assays. To perform a neutralization assay, a recombinant polypeptide representing epitopes of an antigenic region of an infectious agent such as a virus, is solubilized and mixed with a sample diluent to a final concentration of between 0.5 to 50.0 µg/ml. A known amount of test sample (preferably 10 µl), either diluted or non-diluted, is added to a reaction well, followed by 400 µl of the sample diluent containing the recombinant polypeptide. If desired, the mixture may be preincubated for approximately 15 minutes to two hours. A solid phase coated with the CKS recombinant protein described herein then is added to the reaction well, and incubated for one hour at approximately 40° C. After washing, a known amount of an indicator reagent, for example, 200 µl of a peroxidase labeled goat anti-human IgG in a conjugate diluent is added and incubated for one hour at 40° C. After washing and when using an enzyme conjugate such as described, an enzyme substrate, for example, OPD substrate, is added and incubated at room temperature for thirty minutes. The reaction is terminated by adding a stopping reagent such as 1N sulfuric acid to the reaction well. Absorbance is read at 492 nm. Test samples which contain antibody to the specific polypeptide generate a reduced signal caused by the competitive binding of the peptides to these antibodies in solution. The percentage of competitive binding may be calculated by comparing absorbance value of the sample in the presence of recombinant polypeptide to the absorbance value of the sample assayed in the absence of a recombinant polypeptide at the same dilution. Thus, the difference in the signals generated between the sample in the presence of recombinant protein and the sample in the absence of recombinant protein is the measurement used to determine the presence or absence of antibody.

In another assay format, the recombinant proteins can be used in immunodot blot assay systems. The immunodot blot assay system uses a panel of purified recombinant polypeptides placed in an array on a nitrocellulose solid support. The prepared solid support is contacted with a sample and captures specific antibodies (specific binding member) to the recombinant protein (other specific binding member) to form specific binding member pairs. The captured antibodies are detected by reaction with an indicator reagent. Preferably, the conjugate specific reaction is quantified using a reflectance optics assembly within an instrument which has been described in U.S. patent application Ser. No. 07/227,408 filed Aug. 2, 1988. The related U.S. patent application Ser. Nos. 07/227,586 and 07/227,590 (both of which were filed on Aug. 2, 1988) further described specific methods and apparatus useful to perform an immunodot assay, as well as U.S. Pat. No. 5,075,077 (U.S. Ser. No. 07/227,272 filed Aug. 2, 1988), which enjoys common ownership and is incorporated herein by reference. Briefly, a nitrocellulose-base test cartridge is treated with multiple antigenic polypeptides. Each polypeptide is contained within a specific reaction zone on the test cartridge. After all the antigenic polypeptides have been placed on the nitrocellulose, excess binding sites on the nitrocellulose are blocked. The test cartridge then is contacted with a test sample such that each antigenic polypeptide in each reaction zone will react if the test sample contains the appropriate antibody. After reaction, the test cartridge is washed and any antigen-antibody reactions are identified using suitable well-known reagents. As described in the patents and patent applications listed herein, the entire process is amenable to automation. The specifications of these applications related to the method and apparatus for performing an immunodot blot assay are incorporated herein by reference.

CKS fusion proteins (recombinant antigens) can be used in assays which employ a first and second solid support, as follow, for detecting antibody to a specific antigen of an analyte in a test sample. In this assay format, for example, when using CKS recombinant antigens, a first aliquot of a test sample is contacted with a first solid support coated with CKS recombinant protein specific for an analyte for a time and under conditions sufficient to form recombinant protein/ analyte antibody complexes. Then, the complexes are contacted with an indicator reagent specific for the recombinant antigen. The indicator reagent is detected to determine the presence of antibody to the recombinant protein in the test sample. Following this, the presence of a different antigenic determinant of the same analyte is determined by contacting a second aliquot of a test sample with a second solid support coated with CKS recombinant protein specific for the second antibody for a time and under conditions sufficient to form recombinant protein/second antibody complexes. The complexes are contacted with a second indicator reagent specific for the antibody of the complex. The signal is detected in order to determine the presence of antibody in the test sample, wherein the presence of antibody to either analyte recombinant protein, or both, indicates the presence of anti-analyte in the test sample. It also is contemplated that the solid supports can be tested simultaneously.

The use of haptens is known in the art. It is contemplated that haptens also can be used in assays employing CKS fusion proteins in order to enhance performance of the assay.

Screening for Anti-Viral Agents For HGBV

The availability of cell culture and animal model systems for HGBV also renders screening for anti-viral agents which inhibit HGBV replication possible, and particularly for those agents which preferentially allow cell growth and multiplication while inhibiting viral replication. These screening methods are known in the art. Generally, the anti-viral agents are tested at a variety of concentrations, for their effect on preventing viral replication in cell culture systems which support viral replication, and then for an inhibition of infectivity or of viral pathogenicity, and a low level of toxicity, in an animal model system. The methods and composition provided herein for detecting HGBV antigens are useful for screening of anti-viral agents because they provide an alternative, and perhaps a more sensitive means, for detecting the agent's effect on viral replication than the cell plaque assay or $ID_{50}$ assay. Anti-HGBV antibodies may be used to identify and quantitate HGBV antigen(s) in the cell culture utilizing the immunoassays described herein. Also, since it may be desirable to quantitate HGBV antigens in the infected cell culture by a competition assay, the polypeptides encoded within the HGBV nucleic acid sequences described herein are useful for these assays. Generally, a recombinant HGBV polypeptide derived from the HGBV genomic or cDNA would be labeled, and the inhibition of binding of this labeled polypeptide to an HGBV polypeptide due to the antigen produced in the cell culture system would be monitored. These methods are especially useful in cases where the HGBV may be able to replicate in a cell lines without causing cell death.

Hosts and Expression Control Sequences

Although the following are known in the art, included herein are general techniques used in extracting the genome from a virus, preparing and probing a genomic library, sequencing clones, constructing expression vectors, transforming cells, performing immunological assays, and for growing cell in culture.

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotics include promoters, optionally containing operator portions, and ribosome binding sites. Transfer vectors compatible with prokaryotic hosts are commonly derived from the plasmid pBR322 which contains operons conferring ampicillin and tetracycline resistance, and the various pUC vectors, which also contain sequences conferring antibiotic resistance markers. These markers may be used to obtain successful transformants by selection. Commonly used prokaryotic control sequences include the beta-lactamase (penicillinase), lactose promoter system (Chang et al., *Nature* 198:1056 [1977]) the tryptophan promoter system (reported by Goeddel et al., *Nucleic Acid Res* 8:4057 [1980]) and the lambda-derived pL promoter and N gene ribosome binding site (Shimatake et al., *Nature* 292:128 [1981]) and the hybrid Tac promoter (De Boer et al., *Proc. Natl. Acad. Sci. USA* 292:128 [1983]) derived from sequences of the trp and lac UV5 promoters. The foregoing systems are particularly compatible with *E. coli*; however, other prokaryotic hosts such as strains of Bacillus or Pseudomonas may be used if desired, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors carry markers which permit selection of successful transformants by conferring protrophy to auxotrophic mutants or resistance to heavy metals on wild-type strains. Yeast compatible vectors may employ the 2 micron origin of replication (as described by Broach et al., *Meth. Enz.* 101:307 [1983]), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes, including the promoter for 3 phosphophycerate kinase. See, for example, Hess et al., *J. Adv. Enzyme Reg.* 7: 149 (1968), Holland et al., *Biochemistry* 17:4900 (1978) and Hitzeman *J. Biol. Chem.* 255:2073 (1980). Terminators also may be included, such as those derived from the enolase gene as reported by Holland, *J. Biol. Chem.* 256:1385 (1981). It is contemplated that particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and include many immortalized cell lines which are available from the American Type Culture Collection. These include HeLa cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV), cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which insure integration of the appropriate sequences encoding non-A, non-B, non-C, non-D, non-E epitopes into the host genome. An example of a mammalian expression system for HCV is described in U.S. patent application Ser. No. 07/830,024, filed Jan. 31, 1992.

Baculovirus Expression Systems

Commercially available baculovirus expression systems are widely available for the production of recombinant proteins in large quantities. Baculovirus systems offer an advantage over bacterial expression systems in that they allow for high level expression of glycosylated proteins, although these modifications may not be identical to native glycosylation. Expression in these systems is achieved by cloning the gene of interest into a transfer vector in which the gene is placed under the control of a strong viral promoter, usually the polyhedrin promoter of the *Autographa californica* nuclear polyhedrosis virus (AcNPV). The transfer vector is then co-transfected into an appropriate insect cell line with baculovirus genomic DNA. Infectious viruses which result from recombination between the transfer vector and viral genomic DNA are then isolated. Selection of recombinant viruses has been greatly facilitated by commercially available baculovirus genomic DNA for transfection. One such system, BaculoGold™ (PharMingen, San Diego, Calif.), is linearized baculovirus genomic DNA that contains a lethal deletion, thus, genomic DNA cannot make infectious virus particles in transfected cells unless the deletion is complemented by a co-transfected polyhedrin-based Baculovirus transfer vector.

In order to direct secretion of the recombinant protein into cell culture supernatants, commercially available transfer vectors are available which allow fusion proteins to be made between a secreted protein signal sequence and the protein of interest. One such vector, pAcGP67A (PharMingen), utilizes the signal sequence of gp67, the most abundant envelope protein of AcNPV. The gp67 signal sequence directs the recombinant protein into the cellular secretion pathway. In doing so, the signal peptide is removed by cellular proteases present in the endoplasmic reticulum, just as would be the case for gp67. The resulting recombinant protein should be secreted into the cell culture supernatants with 3 gp67 amino acids present on the amino-terminus.

Transformations

Transformation may be by any known method for introducing polynucleotides into a host cell, including packaging the polynucleotide in a virus and transducing a host cell with the virus, and by direct uptake of the polynucleotide. The transformation procedures selected depends upon the host to be transformed. Bacterial transformation by direct uptake generally employs treatment with calcium or rubidium chloride. Cohen, *Proc. Natl. Acad. Sci. USA* 69:2110 (1972). Yeast transformation by direct uptake may be conducted using the calcium phosphate precipitation method of Graham et al., *Virology* 52:526 (1978), or modification thereof.

Vector Construction

Vector construction employs methods known in the art. Generally, site-specific DNA cleavage is performed by treating with suitable restriction enzymes under conditions which generally are specified by the manufacturer of these commercially available enzymes. Usually, about 1 microgram ($\mu$g) of plasmid or DNA sequence is cleaved by 1–10 units of enzyme in about 20 $\mu$l of buffer solution by incubation at 37° C. for 1 to 2 hours. After incubation with the restriction enzyme, protein is removed by phenol/chloroform extraction and the DNA recovered by precipitation with ethanol. The cleaved fragments may be separated using polyacrylamide or agarose gel electrophoresis methods, according to methods known by the routineer.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Sticky end ligations require less ATP and less ligase than blunt end ligations. When vector fragments are used as part of a ligation mixture, the vector fragment often is treated with bacterial alkaline phosphatase (BAP) or calf intestinal alkaline phosphatase to remove the 5'-phosphate and thus prevent religation of the vector. Or, restriction enzyme digestion of unwanted fragments can be used to prevent ligation. Ligation mixtures are transformed into suitable cloning hosts such as *E. coli* and successful transformants selected by methods including antibiotic resistance, and then screened for the correct construction.

Verification of Construction and Sequencing

For standard vector constructions, ligation mixtures are transformed into *E. coli* strain XL-1 Blue or other suitable host, and successful transformants selected by antibiotic resistance or other markers. Plasmids from the transformants then are prepared according to the method of Clewell et al., *Proc. Natl. Acad. Sci. USA* 62:1159 (1969) usually following chloramphenicol amplification as reported by Clewell et al., *J. Bacteriol.* 110:667 (1972). The DNA is isolated and analyzed usually by restriction enzyme analysis and/or sequencing. Sequencing may be by the well-known dideoxy method of Sanger et al., *Proc. Natl. Acad. Sci. USA* 74:5463 (1977) as further described by Messing et al., *Nucleic Acid Res.* 9:309 (1981), or by the method reported by Maxam et al., *Methods in Enzymology* 65:499 (1980). Problems with band compression, which are sometimes observed in GC rich regions, are overcome by use of T-deazoguanosine according to the method reported by Barr et al., *Biotechniques* 4:428 (1986).

Enzyme-Linked Immunosorbent Assay

Enzyme-inked immunosorbent assay (ELISA) can be used to measure either antigen or antibody concentrations. This method depends upon conjugation of an enzyme label to either an antigen or antibody, and uses the bound enzyme activity (signal generated) as a quantitative label (measurable generated signal). Methods which utilize enzymes as labels are described herein, as are examples of such enzyme labels.

The present invention will now be described by way of examples, which are meant to illustrate, but not to limit, the spirit and scope of the invention.

EXAMPLES

The initial studies of the transmissibility of HGBV were performed as described in U.S. Ser. No. 08/283,314, U.S. Ser. No. 08/242,654, and U.S. Ser. No. 08/196,030, all of which have been incorporated previously herein by reference. Additional infectivity studies have been disclosed and described in these three preceding applications and in U.S. Ser. Nos. 08/344,185 and 08/344,190, each filed Nov. 23, 1994 and previously incorporated herein by reference. These previous applications also disclosed examples describing the extension of the HGBV clone sequence (generation of HGBV sequences, evidence for the existence of two HCV-like viruses in HGBV, evidence that HGBV-A and HGBV-B represent two distinct RNA species and distinct viruses, and evidence that HGBV-A and HGBV-B are members of the Flaviviridae); an example detailing the CKS-based expression vector system for expression and detection of immunogenic HGBV polypeptides, serological studies which utilized recombinant protein and its purification protocol and included a polystyrene bead coating procedure, the ELISA protocol for detection of antibodies to HGBV, and the detection of HGBV derived RNA in serum from infected individuals including humans and tamarins; an example which detailed the evidence for exposure to HGBV in human populations, including the experimental protocol used, the cutoff determinations, supplemental testing, serological data obtained with low-risk specimens, specimens tested which were from individuals considered "at risk" for hepatitis over various counties of the world, and the statistical significance of serological results obtained from testing; another example detailed additional studies which provided evidence for exposure to HGBV in human populations, including experimental protocol utilized, cutoff determination, supplemental testing, serological data obtained with low-risk specimens, serological data obtained from individuals "at risk" for hepatitis and the statistical significance of serological results; another example set forth the identification of a GB-related virus in humans, and detailed the scientific reasoning to its identification, the detailed cloning of the NS3-like region of HGBV-C, nucleotide sequences totaling 5163 bp in length, the scientific experiments which led to the conclusion that GB-C is exogenous, experiments that GB-C can be detected in additional human serum samples, experiments which detailed the PCR walking technique used to extend the HGBV-C sequence, all of which was presented as a nucleic acid sequence and a six-frame translation of the 5163 bp. These sequences are set forth in U.S. Ser. No. 08/344,190 filed Nov. 23, 1994, which previously has been incorporated herein by reference. The sequence was obtained from clone pHGB-C clone #1, previously deposited at the A.T.C.C. and accorded A.T.C.C. Deposit No. 69711 on Nov. 8, 1994 as described in U.S. Ser. No. 08/344,190; these sequences were identified in U.S. Ser. No. 08/344,190 as SEQUENCE I.D. No. 76 and its six possible reading frames. U.S. Ser. No. 08/377,557 filed Jan. 30, 1995 (previously incorporated herein by reference) extended the 5163 bp sequence to a length of 8087 bp and also provided a translation of the three forward reading frames of the 8087 bp sequence. U.S. Ser. No. 08/424,550 (previously incorporated herein by reference) extended the 8087 bp of HGBV-C to 9034 bp and also provided additional serological data relating to HGBV-A, HGBV-B and HGBV-C. The P.C.T. application corresponding to these applications, PCT/US95/02118, was published Aug. 18, 1995. Ser. No. 08/417,629 extended the HGBV-C sequence 88 bp, thus extending the sequence to 9122 bp, and also updated serological data of HGBV-A, HGBV-B and HGBV-C by correlating antibody detection and PCR results in Western Africa and summarizing PCR results in volunteer blood donors, I.V. drug users and non-A–E hepatitis individuals.

Example 1

CKS-based Expression and Detection of Immunogenic HGBV-C Polypeptides

The HGBV-C sequences obtained from walking experiments previously described in Example 18 (TABLE 21) of U.S. Ser. No. 08/424,550 were cloned into the CKS expression vectors pJO200, pJO201, and pJO202 using the restriction enzymes listed hereinbelow in TABLE 1 and in TABLE 22 of U.S. Ser. No. 08/424,550 (10 units, NEB), following procedures described in Example 13 of U.S. Ser. No. 08/424,550 and known in the art. Two additional PCR clones, designated C.3/2 and C.8/12, were also expressed (FIG. 1). Briefly, PCR product C.3/2 was generated using primers SEQUENCE I.D. NO. 29 and the complement of SEQUENCE I.D NO. 30 and PCR product C.8/12 was generated using primers SEQUENCE I.D. NO. 31 and the complement of SEQUENCE I.D. No. 32, following procedures previously described in Example 9 of U.S. Ser. No. 08/424,550 and known in the art. The PCR products were cloned into pT7Blue as described previously, then liberated with the restriction enzymes listed in TABLE 1 and also in TABLE 22 of U.S. Ser. No. 08/424,550 and cloned into pJO200, pJO201 and pJO202, following known standard methods and as described in Example 13 of U.S. Ser. No. 08/424,550.

TABLE 1

| HGBV-C Samples | | | |
|---|---|---|---|
| PCR product[a] | Restriction digest[b] | Reactivity with human G8-81 serum | Reactivity with human 240D serum |
| GB-C | KpnI, XbaI | + | − |
| C.1 | EcoRI, XbaI | + | − |
| C.3/2 | EcoRI, XbaI | − | − |
| C.4 | KpnI, XbaI | − | − |
| C.9 | KpnI, PstI | ND | − |
| C.10 | EcoRI, XbaI | ND | − |
| C.5 | KpnI, XbaI | +/− | − |
| C.6 | KpnI, PstI | + | − |
| C.7 | NdeI-fill, BamHI | − | + |
| C.8/12 | KpnI, XbaI | + | − |

[a]PCR product is as indicated in previous TABLES or Examples.
[b]Restriction digests used to liberate the PCR fragment from pT7Blue T-vector.
ND = not done.

Two human sera which had indicated the presence of antibodies to one or more of the CKS/HGBV-A or CKS/HGBV-B fusion proteins by the 1.7, 4.1 or 2.17 ELISAs (see Examples 15 and 16 of U.S. Ser. No. 08/424,550) were chosen for Western blot analysis. One of these sera (240 D) was from an individual with non A–E hepatitis (Egypt) and the other (G8-81) was from a West African individual "at risk" for exposure to HGBV (see Example 15 of U.S. Ser. No. 08/424,550). The CKS/HGBV-C fusion proteins were expressed and transferred to nitrocellulose sheets as previously described in Example 13 of U.S. Ser. No. 08/424,550, and as known in the art. The blots were preblocked as previously described in Example 13 of U.S. Ser. No. 08/424,550 and known in the art, and incubated overnight with one of the human serum sample diluted 1:100 in blocking buffer containing 10% *E. coli* lysate and 6 mg/ml XL1-Blue/CKS lysate. The blots were washed two times in TBS, reacted with HRPO-conjugated goat anti-human IgG and developed as indicated in Example 13 of U.S. Ser. No. 08/424,550. The results are shown in TABLE 1 and in TABLE 22 of U.S. Ser. No. 08/424,550.

Several of the HGBV-C proteins showed reactivity with one or the other of the two sera, and three (C.1, C.6 and C.7) were chosen for use in ELISA assays following methods described hereinabove (see Example 20 of U.S. Ser. No. 08/424,550). Thus, samples previously identified as reactive with HGBV-A and/or HGBV-B proteins additionally showed reactivity with HGBV-C proteins. The reactivity with multiple proteins from the 3 HGBV viruses may have been due to cross-reactivity resulting from shared epitopes between the viruses. Alternatively, this may have been a result of infection with multiple viruses, or to other unidentified factors.

Example 2

Epitope Mapping of Immunoreactive HGBV-C Proteins

The reactive fragments GB-C, C.1, C.5, C.6, C.7 and C.8/12 previously identified in Example 19 of U.S. Ser. No. 08/424,550, previously incorporated herein by reference, span a region of the HGBV-C large open reading frame (SEQUENCE I.D. NO. 33) from residues 876 to 2335 (see FIG. 1). A set of fourteen overlapping PCR fragments covering this area of HGBV-C was generated to further localize the antigenic regions. HGBV-C PCR products were generated from cDNA derived from the West African sample used to originally identify GB-C (see Example 18 of U.S. Ser. No. 08/424,550. Nucleic acid extractions and cDNA reactions were performed as described. All PCRs utilized 1 µM primers for 35–40 cycles (94° C., 20–30 sec; 50–55° C., 30 sec; 72° C., 30–120 sec). Primers for each clone are shown in TABLE 2. Each primer had a restriction site added at the 5' end to facilitate cloning into the pJO201 multiple cloning site, preceded by six nucleotides to ensure complete digestion of the PCR product. The products were cloned into pJO201 as described in Example 13 of U.S. Ser. No. 08/424,550. The restriction sites engineered into the primers and the locations of the encoded proteins within The HGBV-C polyprotein are also shown in TABLE 2.

sequence library have been deposited at the American Type Culture Collection, 12301 Parklawn Drive, Rockville, Md. 20852, as of Oct. 10, 1995, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone 17 (C.17) was accorded A.T.C.C. Deposit No. 69910; Clone 18 (C.18) was accorded A.T.C.C. Deposit No.69911;

TABLE 2

| PCR product[a] | Restriction sites[b] | Primer set | Residues in SEQ I.D. No. 404[c] | Reactivity with human G8-81 serum | Reactivity with human 240E serum | Reactivity with human M47 serum |
|---|---|---|---|---|---|---|
| C.17 | BamHI, HindIII | SEQ ID #1/SEQ ID #2 | 865–974 | − | − | − |
| C.18 | EcoRI, HindIII | SEQ ID #3/SEQ ID #4 | 965–1082 | − | − | − |
| C.19 | BamHI, HindIII | SEQ ID #5/SEQ ID #6 | 1073–1190 | + | − | − |
| C.20 | BamHI, HindIII | SEQ ID #7/SEQ ID #8 | 1181–1298 | − | − | − |
| C.21 | BamHI, HindIII | SEQ ID #9/SEQ ID #10 | 1289–1406 | − | − | − |
| C.22 | BamHI, HindIII | SEQ ID #11/SEQ ID #12 | 1397–1512 | − | − | − |
| C.23 | BamHI, HindIII | SEQ ID #13/SEQ ID #14 | 1503–1622 | − | − | − |
| C.24 | BamHI, HindIII | SEQ ID #15/SEQ ID #16 | 1613–1721 | + | − | − |
| C.25 | BamHI, HindIII | SEQ ID #17/SEQ ID #18 | 1712–1838 | − | − | − |
| C.26 | BamHI, HindIII | SEQ ID #19/SEQ ID #20 | 1829–1948 | − | − | − |
| C.27 | BamHI, HindIII | SEQ ID #21/SEQ ID #22 | 1939–2055 | − | − | − |
| C.28 | BamHI, HindIII | SEQ ID #23/SEQ ID #24 | 2046–2163 | + | + | + |
| C.29 | BamHI, HindIII | SEQ ID #25/SEQ ID #26 | 2154–2270 | + | − | + |
| C.30 | BamHI, HindIII | SEQ ID #27/SEQ ID #28 | 2261–2378 | − | − | + |

[a]PCR product is as indicated in FIG. X.
[b]Restriction sites engineered into PCR primers and used to clone the PCR fragment into pJO201.
[c]From U.S. Ser. No. 08/424,550.

Cultures expressing the new CKS/HGBV-C fusion proteins were grown and proteins were transferred to nitrocellulose as previously described in Example 13 of U.S. Ser. No. 08/424,550 and following standard methods known in the art. The proteins were reacted with the two human sera described in Example 19 of U.S. Ser. No. 08/424,550, except that a different bleed date ten days subsequent to the one used previously was utilized for the Egyptian 240 sera. An additional sera (M47), which was found to be PCR positive for HGBV-C, was reacted with the proteins as well. The reactivities of the proteins with these sera also are indicated in TABLE 2. PCR fragments C.19, C.24, C.28, C.29 and C.30 showed reactivity with at least one of the sera. Fragment C.28 was reactive with all three sera. Fragment C.19 maps the C.1 reactive region to residues 1073–1190 of the HGBV-C large open reading frame (SEQUENCE I.D. NO. 33) and fragment C.24 maps the C.6 reactive region to residues 1613–1721 of SEQUENCE I.D. NO. 33. Fragments C.28, C.29 and C.30, spanning residues 2046–2378 of SEQUENCE I.D. NO. 33, were all reactive indicating the presence of at least two epitopes in this region. Although fragments GB-C and C.5 had shown some reactivity previously with the G8-81 sera, none of the epitope mapping fragments in these regions showed reactivity. It may have been that the new fragments split an epitope such that the epitope is not fully represented in any of the new constructs. Alternatively, the reactivity seen with the larger proteins may have been due to some type of conformational epitope not fully represented in the smaller products.

Strains replicated (clones 17, 18, 19, 20, 21, 22, 23, 24, 25, 26, 27, 28, 29 and 30) from the HGBV nucleic acid Clone 19 (C.19) was accorded A.T.C.C. Deposit No. 69912;
Clone 20 (C.20) was accorded A.T.C.C. Deposit No. 69913;
Clone 21 (C.21) was accorded A.T.C.C. Deposit No.69914;
Clone 22 (C.22) was accorded A.T.C.C. Deposit No. 69915;
Clone 23 (C.23) was accorded A.T.C.C. Deposit No. 69916;
Clone 24 (C.24) was accorded A.T.C.C. Deposit No. 69917;
Clone 25 (C.25) was accorded A.T.C.C. Deposit No. 69918;
Clone 26 (C.26) was accorded A.T.C.C. Deposit No. 69919;
Clone 27 (C.27) was accorded A.T.C.C. Deposit No. 69920;
Clone 28 (C.28) was accorded A.T.C.C. Deposit No. 69921;
Clone 29 (C.29) was accorded A.T.C.C. Deposit No. 69922;
and Clone 30 (C.30) was accorded A.T.C.C. Deposit No. 69923.

Example 3

Expression of GBV-C Polypeptides in a Permanent Cell Line

A. Construction of GBV-C E2 Expression Plasmid

Plasmid 577, described in U.S. patent application Ser. No. 08/478,073, filed Jun. 7, 1995 and previously incorporated herein by reference, has been constructed for the expression of secreted antigens, particularly hepatitis C E2 protein, in a permanent cell line. This plasmid contains the following DNA segments: (a) a 2.3 Kb fragment of pBR322 containing bacterial beta-lactamase and origin of DNA replication; (b) a 1.8 Kb cassette directing expression of a neomycin resistance gene under control of HSV-1 thymidine kinase promoter and poly-A addition signals; (c) a 1.9 Kb cassette directing expression of a dihydrofolate reductase gene under the control of an SV-40 promoter and poly-A addition signals; (d) a 3.5 Kb cassette directing expression of a rabbit immunoglobulin heavy chain signal sequence fused to a modified hepatitis C virus E2 protein under the control of the Simian Virus 40 T-Ag promoter and transcription enhancer, the hepatitis B virus surface antigen enhancer I followed by a fragment of Herpes Simplex Virus-I genome providing poly-A addition signals; and (e) a residual 0.7 Kb fragment of Simian Virus 40 genome late region of no function in this plasmid.

Figure 2:
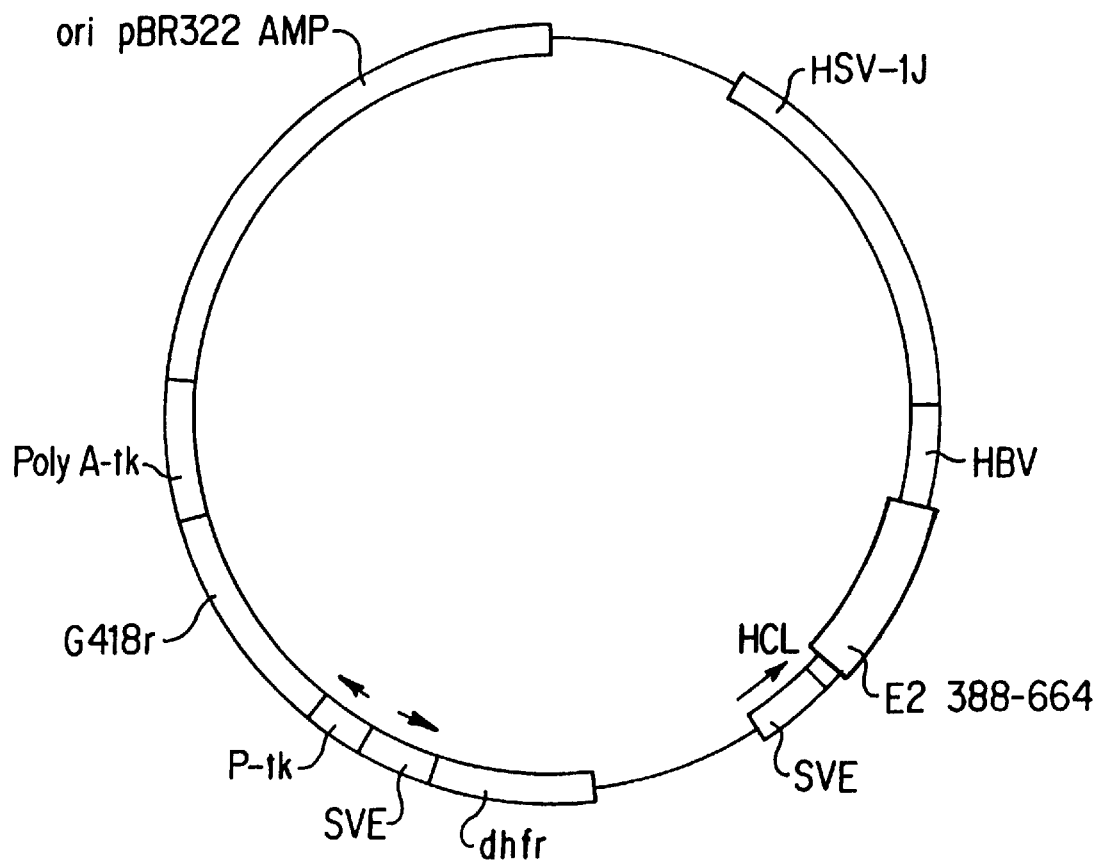
FIG. 2 is a graphic representation of plasmid 577.

Plasmid 577 is graphically depicted in FIG. 2. The plasmid in FIG. 2 is disclosed as a series of assembled fragments with sections numbered 1 to 13, and described in the following TABLE 3. The accession numbers of the sections in TABLE 3 refer to GenBank® accession numbers. Please note that slight sequence variations may occur and may have occurred when constructing the plasmid. All of the segments of the vector were assembled by standard methods known to those skilled in the art of molecular biology.

TABLE 3

Plasmid Figure Legend Construction
Plasmid 577, 10,186 base pairs double stranded DNA

| SECTION | DESCRIPTION |
|---|---|
| 1 | (NT 4361-2067 OF PBR322 ACCESSION J02224) |
| 2 | (NT 2249-1624 HSV-1 ACCESSION J02224 NT) |
| 3 | (NT 2518-1519 Tn5 ACCESSION NOS U00004 L19385) |
| 4 | (NT 460-210 HSV-1 ACCESSION J02224) |
| 5 | (NT 272-1, 5243-5173 SV40) |
| 6 | (NT 1-701 MOUSE DHFR ACCESSION L26316) |
| 7 | (NT 4714-4100 SV40 ACCESSION V08380) |
| 8 | (NT 272-1, 5243-5173 SV40) |
| 9 | (NT 1-77 DNA Sequence Figure SYNTHETIC DNA RABBIT IgG HEAVY CHAIN LEADER (HCL)) |
| 10 | (NT 78-938 DNA Sequence Figure HCV E2 antigen PCR product) |
| 11 | (HBV ENHANCER NT 2373-2811 ACCESSION NO. X02763 WITH G AT NT. 2976 AND T AT NT. 2654) |
| 12 | (NT 3688-5468 HSV1 ACCESSION NO. NT 3687-5468) |
| 13 | (NT 2536-1785 SV40 ACCESSION V08380) |

Plasmids for the expression of secretable GBV-C proteins were constructed by replacing the hepatitis C virus E2 protein coding sequence in plasmid 577 with those from GBV-C, as follows. All GBV-C inserts were from SEQUENCE I.D. NO. 34, a GBV-C genotype 1 sequence previously described in patent application Ser. No. 08/580, 038, previously incorporated herein by reference. Digestion of plasmid 577 with XbaI released the hepatitis C virus E2 gene fragment. The resulting plasmid backbone allowed insertion of GBV-C gene products downstream of the rabbit immunoglobulin heavy chain signal sequence which directs the expressed proteins into the secretory pathway of the cell. All of the GBV-C fragments were generated by PCR using standard procedures. The first PCR fragment encoded a 336 amino acid segment of the GBV-C E2 gene, from aa 221 to 556 of SEQUENCE I.D. NO. 35. Encoded in the sense PCR primer sequence (SEQUENCE I.D. NO. 36) was an Xba 1 site, immediately followed by a 12 nucleotide sequence that encoded the amino acid sequence Ser-Asn-Glu-Leu ("SNEL"), the amino terminal sequence of human pro-urokinase. The amino acid sequence SNEL was intended, as the N-terminus of the protein, to promote signal protease processing, efficient secretion and final product stability in culture fluids. Immediately following this 12 nucleotide sequence the primer contained nucleotides complementary to template sequences encoding amino acids starting at residue 221 of GBV-C. The antisense PCR primer (SEQUENCE I.D. NO. 37) contained sequences homologous to template sequences that encode amino acids ending at residue 556 of GBV-C, followed by two stop codons and an Xba 1 site for cloning purposes. The GBV-C E2 protein was truncated at this position to promote secretion. PCR was performed using GeneAmp® reagents obtained from Perkin-Elmer-Cetus, essentially as directed by the supplier's instructions. PCR primers were used at a final concentration of 0.5 $\mu$M. PCR was performed on plasmid template in a 100 $\mu$l reaction for 35 cycles (94° C., 30 seconds; 55° C., 30 seconds; 72° C., 90 seconds) followed by an extension cycle of 72° C. for 10 min.

Three additional GBV-C E2-encoding plasmids were constructed using the same sense primer as above, but utilizing three different antisense primers (SEQUENCE I.D. NOs. 38, 39, and 40), the same plasmid template and the same PCR conditions. These PCR fragments encoded 315, 289 and 222 amino acid segments of GBV-C E2, each beginning at amino acid residue 221 of SEQUENCE I.D. NO. 35. As with the 336 amino acid GBV-C E2 protein, the truncation sites were chosen to promote secretion. The antisense primers SEQUENCE I.D. NOs. 38 and 39 (utilized to make the 315 and 289 amino acid constructs, respectively) each incorporated a sequence encoding the eight amino acids Asp-Tyr-Lys-Asp-Asp-Asp-Asp-Lys just before the stop codons. Within this sequence is the recognition site for a monoclonal antibody (MAb) designated anti-FLAG M2 (Eastman Kodak, Co.; New Haven, Conn.). It was incorporated to aid in analysis and purification of the GBV-C E2 protein products.

B. Transfection of Dihydrofolate Reductase Deficient Chinese Hamster Ovary Cells The plasmids described supra were transfected into CHO/dhfr- cells (DXB-111) (Uriacio, et al., *Proc. Nat. Acad. Sci.* 77, 4451–4466; 1980); these cells are available from the American Type Culture Collection [A.T.C.C.], 12301 Parklawn Drive, Rockville, Md. 20852, under Accession No. CRL 9096), using the cationic liposome-mediated procedure (Felgner, P. L. et al., *Proc. Natl. Acad. Sci.* 84, 7413–7417; 1987), as follows. CHO/dhfr- cells were cultured in Ham's F-12 media supplemented with 10% fetal calf serum, L-glutamine (1 mM) and freshly seeded into a 25 cm$^2$ flask at a density of 5–8×10$^5$ cells per flask. The cells were grown to between 60 and 80% confluency for transfection. Twenty micrograms of plasmid DNA was added to 1.5 ml of Opti-MEM I medium and 100 microliters ($\mu$l) of Lipofectin Reagent (Gibco-BRL; Grand Island, N.Y.) was added to a second 1.5 ml portion of Opti-MEM I media. The two solutions were mixed and incubated at room temperature for 20 minutes. The culture medium was removed from cells and cells were rinsed three times with 5 ml of Opti-MEM I medium. The Opti-MEM I-Lipofection-plasmid DNA solution was then overlaid onto the cells. The cells were incubated for three hours at 37° C., after which time the Opti-MEM I-Lipofectin-DNA solution was replaced with culture medium for an additional 24 hours prior to selection.

C. Selection and Amplification

One day after transfection, cells were passaged 1:3 and incubated with dhfr/G418 selection medium (hereafter, "F-12 minus medium G"). Selection medium was Ham's F-12 with L-glutamine and without hypoxanthine, thymidine, and glycine (JRH Biosciences, Lenexa, Kans.), and 300 micrograms per ml G418 (Gibco-BRL; Grand Island, N.Y.). Media volume to surface area ratios of 5 ml per 25 cm$^2$ were maintained.

Colonies showing the presence of dihydrofolate reductase (Ringold, et al., *J. Mol Appl. Genet.* 1:165–174; 1981) plus aminoglycoside phosphotransferase (Southern, P. J. and Berg, P. J., *Mol. Appl. Genet.* 1:327–341; 1981) appeared after 4–5 days of incubation of transfected cells with F-12 minus medium G. After approximately two weeks, DHFR/G418 cells were sufficiently expanded to allow passage and continuous maintenance in F-12 minus medium G.

Amplification of each of the transfected GBV-C E2 genes was achieved by stepwise selection of DHFR$^+$, G418$^+$ cells with methotrexate (reviewed by Schimke, R., *Cell* 37, 705–713 (1984). Cells were incubated with F-12 minus medium G containing 150 nM methotrexate (MTX) (Sigma; St. Louis, Mo.) for approximately two weeks until resistant colonies appeared. Further gene amplification was achieved by selection of 150 nM adapted cells with 5 $\mu$M MTX. This adaption process also took several weeks. Five $\mu$M MTX adapted cells were used for all antigen production.

D. Maintenance and Storage of Cell Lines

Cells in culture and undergoing selection or amplification procedures were re-fed with either F-12 minus medium G, F-12 minus medium G with 150 nm MTX or F-12 minus medium G with 5 $\mu$M MTX three times weekly. Cells were passaged 1:4 into 75 cm$^2$ flasks with 15 ml of media described hereinabove and incubated at 37° C. with 5% CO$_2$ using standard methods. Cryostorage was accomplished by resuspension of 2–4×10$^6$ cells in 1.8 ml of either F-12 minus medium G, F-12 minus medium G with 150 nm MTX or F-12 minus medium G with 5 $\mu$M MTX depending on the stage of selection and amplification of the cell line, which also contained 5% DMSO (Sigma; St. Louis, Mo.). Cells underwent cold storage for 24 hours at –80° C. and then permanent storage at –135° C.

E. GBV-C E2 Antigen Production

F-12 minus medium G supplemented with 5 $\mu$M MTX was overlaid onto just confluent monolayers for 12 to 24 hours at 37° C. in 5% CO$_2$. Then, the growth medium was removed and the cells were rinsed three times with Dulbecco's phosphate buffered saline (PBS) (with calcium and magnesium) (Gibco-BRL; Grand Island, N.Y.), to remove the remaining media/serum which might be present. Cells then were incubated with VAS custom medium (VAS custom formulation with L-glutamine with HEPES without phenol red, available from JRH Bioscience; Lenexa, Kans., product number 52-08678P), for one hour at 37° C. in 5% CO$_2$. Cells then were overlaid with VAS for production at 5 ml per T 25 cm$^2$ flask, scaled proportionally for larger flasks or roller bottles). For harvest 1, the medium was removed after 7 days of incubation and then frozen to await purification with harvests 2, 3 and 4. The monolayers were overlaid with VAS for three more 7-day harvests. The cultures were observed daily to determine cell conditions.

F. Analysis of GBV-C E2 Antigen Expression

Aliquots of VAS supernatants from the cells expressing the GBV-C E2-336 amino acid construct were analyzed by SDS-polyacrylamide gel electrophoresis (SDS-PAGE) using standard methods and reagents known in the art (Laemmli discontinuous gels) to assess protein expression levels and reactivity with human and rabbit antisera. In some cases, supernatants were first concentrated by ultrafiltration using Amicon concentrator units with 10 kilodalton (kDa) MWCO (Amicon, Inc., Beverly, Mass.). After electrophoresis, proteins were electrophoretically transferred to polyvinylidene fluoride membranes and analyzed by immunoblotting as described in Example 13 of U.S. Ser. No. 08/424,550 and known in the art. An immunoreactive band of approximately 54 kDa was found to be reactive with several sera, including: (1) sera from eight rabbits previously immunized with an *E. coli* derived GBV-C E2 protein or with peptides whose sequences are found within the GBV-C E2 protein; (2) two GBV-C E2 RT-PCR positive human sera which previously tested seronegative with other GBV-C derived recombinant proteins; (3) two GBV-C RT-PCR positive human sera which previously had tested seropositive with other GBV-C derived recombinant proteins; (4) three RT-PCR negative human sera which previously tested seropositive with other GBV-C derived recombinant proteins; and (5) four RT-PCR negative human sera which previously tested seronegative with other GBV-C derived recombinant proteins. Deglycosylation of this 54 kDa protein with N-Glycanase (Genzyme Corp.; Cambridge, Mass.) was performed after denaturation in the presence of 0.5% SDS, 50 mM b-mercaptoethanol and 50 mM EDTA. Deglycosylation was for 60 hours at 37° C. in pH 7.5 buffer containing 0.17% SDS, 16.7 mM b-mercaptoethanol, 16.7 mM EDTA, 1.25% Nonidet P40 and 0.9 units of N-Glycanase per mg protein. Immunoblotting showed a shift of the immunoreactive band down to 37 kilodaltons, the expected size of the non-glycosylated GBV-C E2-336 protein.

G. Purification of GBV-C E2 Antigens

Protein purification of CHO/E2-315 was performed as follows. For purification of protein, VAS medium from harvests was clarified by centrifugation at 1500×g for 15 minutes or by filtration through a 0.45 $\mu$m cellulose acetate membrane, followed by concentration up to 100× by ultrafiltration using Amicon concentrator units with 10 kDa molecular weight cut-off (Amicon, Inc.; Beverly, Mass.).

Figure 7:
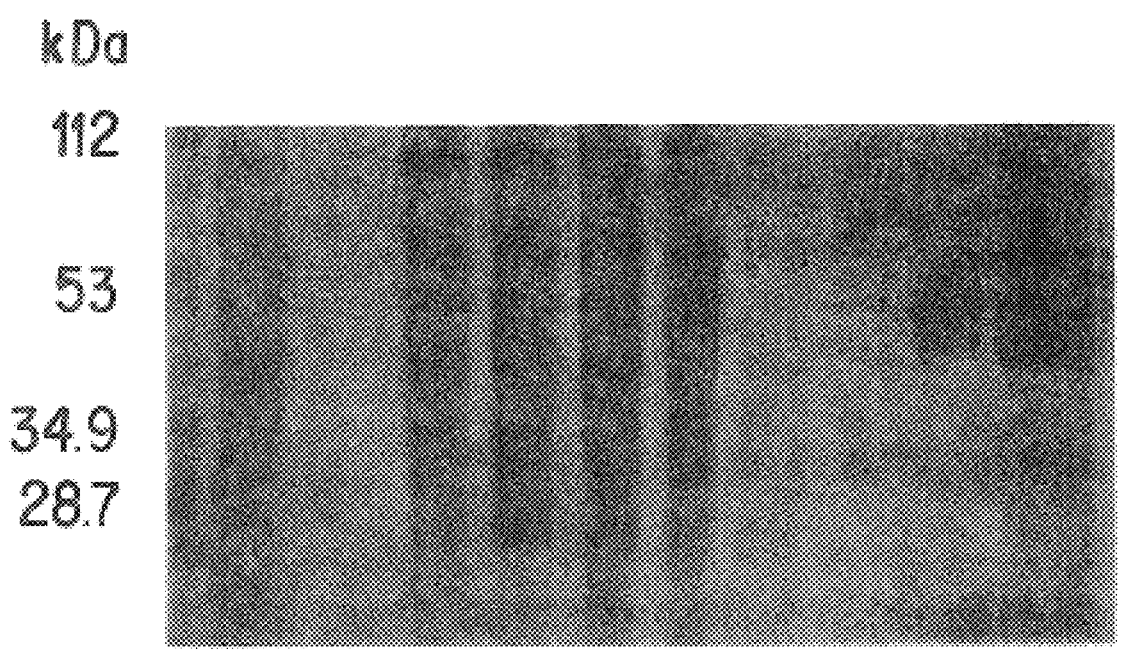
FIG. 7 shows a Coomassie Brilliant Blue R-250 stained SDS polyacrylamide gel of the GBV-C E2 315 protein, wherein M designates molecular weight markers, SM designates starting material (concentrated, clarified VAS medium from GBV-C E2 315-transfected cells, wherein non-binding fractions refer to protein which did not bind to anti-FLAG antibody affinity column, wherein GBV-C E2 315 refers to the protein eluted from anti-FLAG M2 antibody affinity column by competition with FLAG peptide, and wherein SDS-PAGE and staining with Coomassie Brilliant Blue R-250 was performed using standard methods and reagents known in the art.

Purification of the GBV-C E2-315 amino acid construct containing the eight amino acid FLAG sequence (Asp-Tyr-Lys-Asp-Asp-Asp-Asp-Lys) at its C-terminus was performed by immunoaffinity chromatography using an affinity matrix comprising anti-FLAG M2 monoclonal antibody covalently attached to agarose by hydrazide linkage (Eastman Kodak Co., New Haven, Conn.). Prior to affinity purification, protein in pooled VAS medium harvests from roller bottles was exchanged into 50 mM Tris, 150 mM NaCl, pH 7.5 buffer using a Sephadex G-25 (Pharmacia Biotech Inc., Uppsala, Sweden) column. Protein in this buffer was applied to the anti-FLAG M2 antibody affinity column, non-binding protein was eluted by washing the column with 50 mM Tris, 150 mM NaCl, pH 7.5 and bound protein was eluted using an excess of FLAG peptide (in 50 mM Tris, 150 mM NaCl, pH 7.5) over the number of moles of antigen binding sites of anti-FLAG M2 monoclonal antibody on the column. FIG. 7 shows a Coomassie Brilliant Blue R-250 stained SDS polyacrylamide gel of the purification. This procedure provided, in one step, GBV-C E2-315 protein judged homogeneous by scanning densitometry of Coomassie Brilliant Blue R-250 stained SDS polyacrylamide gels of the FLAG peptide - eluted protein. For use in immunoassay, the FLAG peptide used for elution was removed from the GBV-C E2 315 purified stock by gel filtration using Sephadex G-25 (Pharmacia Biotech Inc., Uppsala, Sweden).

Purification of the GBV-C E2-336 amino acid construct was performed using a series of columns which included utilizing two or more of the following types of chromatographies: cation exchange, anion exchange, lectin affinity, hydrophobic interaction.

Example 4

Transient Expression of GBV-C Polypeptides Using the Sindbis and Semliki Forest Virus Vector Systems A. Construction of Secretion Vectors Two systems for transient expression of proteins in alphavirus vectors are now commercially available. The Sindbis virus system (Invitrogen Corp., San Diego, Calif.) and Semliki forest virus (SFV) system (Gibco/BRL; Grand Island, N.Y.) allow for high expression levels of proteins in a variety of eukaryotic cell lines. In both cases, the gene of interest is inserted into a plasmid such that it is under the control of the viral subgenomic promoter. This plasmid is used to make a genome length RNA transcript in vitro. This RNA can then be transfected into a eukaryotic cell line and, once inside the cell, this RNA acts as a messenger RNA and directs translation of protein from the inserted gene of interest. Because this subgenomic RNA becomes the most abundant mRNA in the cell, it recruits a large portion of the cell's translational machinery and thus results in production of high levels of the protein of interest. For a more detailed description of the two systems, see Liljestrom and Garoff, Bio/Technology 9:1356–1361 (1991) and Bredenbeek et al., J. Virol. 67:6439–6446 (1993).

In order to direct secretion of proteins not normally secreted, a cassette encoding the human lysozyme secretion signal was inserted into both the Sindbis expression plasmid (pSinRep5) and the SFV expression plasmid (pSFV1). For pSinRep5, two oligonucleotides were generated (SEQUENCE I.D. NOs. 41 and 42) such that when annealed, the duplex had on each end overhangs compatible with cloning into an XbaI site. This oligonucleotide duplex then was ligated into XbaI-digested pSinRep5. When the resulting plasmid, pSinRep-ss, was digested with XbaI, the upstream site was not cut due to a mutation of one base in the XbaI recognition site. This allowed cloning of a gene at the downstream XbaI site such that the first amino acid encoded by the inserted gene followed directly after the signal peptidase cleavage site encoded by the lysozyme signal sequence. The lysozyme signal sequence thus directed the protein encoded by the inserted gene into the cellular secretion pathway. An analogous strategy was used for insertion of the signal sequence into pSFV1, except that the cloning site was BamHI. The oligonucleotides used for this construct were SEQUENCE I.D. NOs. 43 and 44, and the resulting plasmid was designated pSFV-ss.

B. Sindbis Constructs

Following the methods described hereinabove, a number of GBV-C sequences encoding both structural and non-structural proteins were inserted into pSinRep5 or pSinRep-ss. These are listed in TABLE 4. The sequences were derived from one of two GBV-C isolates: SEQUENCE I.D. NO. 34 is the prototype GBV-C sequence previously described in patent application Ser. No. 08/580,038, and belongs to GBV-C genotype 1 based on analysis described in that application. SEQUENCE I.D. NO. 45 belongs to GBV-C genotype 3 based on analysis described in the same application. Four of the fragments expressed in this system were the same GBV-C E2 constructs described hereinabove in Example 3 (designated E2-222, E2-289, E2-315, and E2-336). These E2 constructs were truncated on the N-terminus to delete the E2 signal sequence and truncated to varying degrees on the C-terminus to delete a putative membrane anchoring domain and other hydrophobic regions which may interfere with secretion. E2-289 and E2-315 have the anti-FLAG recognition sequence on the C-teminus as described supra. All four of these were inserted into pSinRep-ss. An additional E2 construct (from the GBV-C genotype 3 isolate) was generated which had the same 3' end as E2-336, but included an additional 16 amino acid residues of GBV-C on the N-terminus. These residues represent the putative GBV-C E2 signal sequence. This fragment, designated E2-352, was cloned into pSinRep5 to allow secretion directed by the putative GBV-C E2 signal sequence. A GBV-C E1 fragment designated E1-168, also from the genotype 3 isolate, was inserted into pSinRep5. It encompassed amino acid residues 12 to 179 of SEQUENCE I.D. NO. 46 and incorporated the putative E1 signal sequence at the 5' end and terminated at the 3' end just upstream of the hydrophobic putative membrane anchoring domain of the E1 protein. Two additional constructs were amplified for expression as non-secreted proteins in pSinRep5. These represented two of the non-structural proteins, NS3 and NS5A, from GBV-C. The NS3 fragment (from the GBV-C genotype 1 isolate) encompassed amino acid residues 912 to 1566 of SEQUENCE I.D. NO. 35 and the NS5A fragment (from the GBV-C genotype 3 isolate) encompassed residues 1877 to 2290 of SEQUENCE I.D. NO. 46.

TABLE 4

| INSERTED FRAGMENT | VECTOR | PCR PRIMERS | NUCLEOTIDE RESIDUES IN SEQ ID #1 | AMINO ACID RESIDUES IN SEQ ID #2 | NUCLEOTIDE RESIDUES IN SEQ ID #3 | AMINO ACID RESIDUES IN SEQ ID #4 |
|---|---|---|---|---|---|---|
| E2-336 | pSinRep-ss | SEQ ID #5/SEQ ID #6 | 1143–2150 | 221–556 | N/A | N/A |
| E2-315 | pSinRep-ss | SEQ ID #7/SEQ ID #6 | 1143–2087 | 221–535 | N/A | N/A |
| E2-289 | pSinRep-ss | SEQ ID #8/SEQ ID #6 | 1143–2009 | 221–509 | N/A | N/A |
| E2-222 | pSinRep-ss | SEQ ID #9/SEQ ID #6 | 1143–1808 | 221–442 | N/A | N/A |
| E2-352 | pSinRep5 | SEQ ID #14/SEQ ID #6 | N/A | N/A | 1085–2140 | 199–550 |
| E1-168 | pSinRep5 | SEQ ID #15/SEQ ID #16 | N/A | N/A | 524–1027 | 12–179 |
| NS3 | pSinRep5 | SEQ ID #17/SEQ ID #18 | 3216–5180 | 912–1566 | N/A | N/A |
| NS5A | pSinRep5 | SEQ ID #19/SEQ ID #20 | N/A | N/A | 6119–7360 | 1877–2290 |

The sense PCR primers for all constructs inserted into pSinRep5, namely constructs not utilizing the lysozyme secretion signal, included a ribosome binding site sequence and initiator methionine just upstream of the GBV-C sequence. The primers for all constructs except NS5A incorporated XbaI sites for cloning into the Sindbis vectors. The primers for the NS5A construct incorporated AvrII sites due to an XbaI site within the NS5A region of GBV-C. The overhang generated by digestion with AvrII was compatible with cloning into an XbaI site. PCRs were performed using GeneAmp® reagents obtained from Perkin-Elmer-Cetus, essentially as directed by the supplier's instructions. PCR primers were used at a final concentration of 1 μM. PCRs were performed on plasmid or cDNA templates in 50 μl reactions for 2540 cycles (94° C., 20 seconds; 50° C., 30 seconds; 72° C., 1–2 min) followed by an extension cycle of 72° C. for 10 min. All PCR products were then digested with XbaI (or AvrII for NS5A), ligated into XbaI-digested, de-phosphorylated pSinRep5 or pSinRep-ss and transformed into E. coli by standard methods. All inserts were sequenced using the dideoxynucleotide chain termination technique (Sanger et al., supra) using either a kit (T7 Sequenase 7-deaza-dGTP DNA sequencing kit, Amersham Life Sciences, Inc.; Arlington Heights, Ill.) followed by manual gel electrophoresis or alternatively, using the ABI Prism Dye Terminator Cycle Sequencing Ready Reaction Kit and an ABI 373 automated sequencer (Perkin Elmer Corp.; Foster City, Calif.).

C. SFV Constructs

TABLE 5 below lists the fragments generated for cloning into the SFV vectors. All were from the GBV-C genotype 1 isolate (SEQUENCE I.D. NO. 34). The E2-222, E2-336, E2-352, E1-168, NS3 and NS5A fragments are identical to those described above for the Sindbis vectors, except for the isolate of GBV-C from which they were derived. Two additional clones were generated for expression in this system. E1-149 is identical to E1-168, except that the sequence encoding the 19 residue putative E1 secretion signal on the 5' end was eliminated, and the fragment was cloned into pSFV-ss in order to utilize the lysozyme signal sequence. The other, E1-E2-NS2/3, is a large fragment encompassing all of E1, E2, NS2, and the 5' third of NS3. It has been predicted that this fragment will direct co-expression, appropriate processing and interaction of E1 and E2.

TABLE 5

| INSERTED FRAGMENT | VECTOR | PRIMERS | NUCLEOTIDE RESIDUES IN SEQ ID #34 | AMINO ACID RESIDUES IN SEQ ID #35 |
|---|---|---|---|---|
| E2-222 | pSFV-ss | SEQ ID #54/SEQ ID #55 | 1143–1808 | 221–442 |
| E2-336 | pSFV-ss | SEQ ID #56/SEQ ID #55 | 1143–2150 | 221–556 |
| E2-352 | pSFV1 | SEQ ID #57/SEQ ID #58 | 1095–2150 | 205–556 |
| E1-149 | pSFV-ss | SEQ ID #59/SEQ ID #60 | 591–1037 | 37–185 |
| E1-168 | pSFV1 | SEQ ID #61/SEQ ID #60 | 534–1037 | 18–185 |
| NS3 | pSFV1 | SEQ ID #62/SEQ ID #63 | 3216–5180 | 912–1566 |
| NS5A | pSFV1 | SEQ ID #64/SEQ ID #65 | 6129–7370 | 1883–2296 |
| E1-E2-NS2/3 | pSFV1 | SEQ ID #66/SEQ ID #67 | 534–3755 | 18–1091 |

The PCR primers for all constructs inserted into pSFV1 and pSFV-ss incorporated BglII sites for cloning. The BglII overhang was compatible with cloning into the BamHI site of the vector, and was utilized because there were BamHI sites but not BglII sites within the amplified GBV-C sequences. PCRs were performed as described above for the Sindbis fragments. All PCR products were then digested with BglII, ligated into BamHI-digested, de-phosphorylated pSFV1 or pSFV-ss and transformed into *E. coli* by employing standard methods. All inserts were sequenced as described above.

D. RNA Synthesis

Prior to in vitro synthesis of RNA, each of the Sindbis and SFV plasmids were linearized at a restriction site downstream of the inserted fragment. The Sindbis constructs were linearized with NotI, while the SFV constructs were linearized with SpeI. After digestion, the DNAs were extracted with phenol-chloroform-isoamyl alcohol (25:24:1), precipitated with ethanol, and resuspended in DEPC-treated $H_2O$. RNA was synthesized using the InvitroScript CAP SP6 In Vitro Transcription Kit (Invitrogen Corp.; San Diego, Calif.) as directed by the manufacturer. The synthesized RNA was divided into approximately 5 mg aliquots and stored at −70° C. without any further manipulations.

E. Cell Culture

The cell line BHK-21 (A.T.C.C. CCL-10) was obtained from the American Type Culture Collection (A.T.C.C.) Rockville, Md. Cells were cultured in growth media consisting of Glasgow Minimum Essential Medium with 2 mM glutamine, 10% tryptose phosphate broth, 5% FCS, 10 mM HEPES, 100 U/ml Penicillin/streptomycin (Gibco-BRL; Grand Island, N.Y.) at 37° C. and 5% $CO_2$. Cultures were routinely split at confluency on 3 or 4 day intervals. For transfection, cells were planted in 850 $cm^2$ roller bottles and grown to 50% confluency. For cell passage or transfection, cells were harvested by removing the growth media and rinsing three times with Dulbecco's Phosphate Buffered Saline (D-PBS) (Gibco-BRL; Grand Island, N.Y.) without calcium and magnesium. Cells were then overlaid with trypsin EDTA (Gibco-BRL; Grand Island, N.Y.) for 5 minutes, and the trypsin and cell suspension was decanted from the bottle. The trypsin in the cell suspension was neutralized with 10% growth media, and the suspension centrifuged at low speed to pellet the cells. For passage, cells were resuspended in growth media and planted in a vessel with a surface area to volume ratio of 25 $cm^2$ to 5 ml of growth media.

F. Transfections

Cells were grown to mid-log phase and harvested from the culture vessel as described above. Cell density was adjusted to a final count of $1\times10^7$ cells in 0.8 ml after 3 washes in D-PBS without calcium and magnesium. Cells were kept at room temperature for less than 30 minutes before electroporation. Approximately 5–10 mg of RNA was added to the 0.8 ml cell suspension and immediately electroporated. Electroporation was conducted at 1250 volts, 25 uF with 3 manual pulses using a Bio-Rad Gene Pulser and a 4 cm Gene Pulser cuvette (Hercules, Calif.). After transfection, cells were allowed to rest for 5 minutes at room temperature in the electroporation cuvette. Cells were then transferred to growth media and planted in a culture vessel. Transfection efficiencies were routinely observed to be 95–100% using RNA derived from the Lac-Z positive control plasmids pSFV3-lacZ or pSinRep/lacZ, and b-galactosidase assay reagents as supplied/described by Gibco BRL.

G. Metabolic Labeling of Transfected Cells

After transfection cells were allowed 5 hours in Glasgow Minimum Essential Medium with 2 mM glutamine, 10% tryptose phosphate broth, 5% FCS, 10 mM HEPES, 100 U/ml Penicillin/Streptomycin (Gibco-BRL, Grand Island, N.Y.) at 37° C. and 5% $CO_2$ to firmly attach to the culture vessel. The growth media was then removed and the cells were washed 3 times with D-PBS with calcium and magnesium. Cells were then overlaid with minimum essential medium without cystine (MEM minus) constructed with a MEM Select-Amine kit (Gibco-BRL; Grand Island, N.Y.). A culture vessel surface area to volume ratio of 25 $cm^2$ to 2 ml was maintained. Radio-labeled [$^{35}$S]cysteine (Amersham Life Sciences; Arlington Heights, Ill.) was added to a final concentration of 75 mCi per ml and cells were incubated at 37° C. and 5% $CO_2$ until the cells and supernatants were harvested. Supernatants were harvested and spun at low speed to pellet any non-adherent cells. Clarified supernatant was then ready for analysis. Adherent cells were washed 3 times in D-PBS with calcium and magnesium and overlaid with lysis buffer (1% Nonidet P-40, 50 mM Tris-HCl pH 7.6, 150 mM NaCl, 2 mM EDTA, 1 mg/ml PMSF). A surface area to volume ratio of 25 cm² to 250 ml of lysis buffer was maintained. Lysis was conducted on wet ice for 10 minutes. Lysates were then harvested from the culture vessel and ready for analysis.

H. Analysis of Protein Expression

Aliquots of labeled cell lysates or supernatants were analyzed by SDS-polyacrylamide gel electrophoresis (SDS-PAGE) using standard methods and reagents (Laemmli discontinuous gels) to assess protein expression levels. In some cases, supernatants were first concentrated by ultra-filtration through Microcon filter units (Amicon, Inc.; Beverly, Mass.) in order to analyze lysates and supernatants from equivalent numbers of cells. After electrophoresis, gels were fixed in 10% acetic acid/40% methanol, dried and developed using a Molecular Dynamics PhosphorImager (Sunnyvale, Calif.), or alternatively, proteins in the gel were electrophoretically transferred to nitrocellulose and analyzed by immunoblotting as described in Example 1.

Radioimmune precipitations were performed on labeled cell lysates and supernatants as follows. Lysates or supernatants were first pre-incubated for 1 hour at 4° C. with Pansorbin cells (Calbiochem Corp.; La Jolla, Calif.). After centrifuging for 15 minutes at 10,000×g, an aliquot of the pre-adsorbed supernatant or lysate was mixed with 2–8 μl of each sera to be examined and incubated on ice for 2–4 hours. Protein A agarose beads were added and tubes were incubated at 4° C. for 1 hour with rocking. The protein A agarose beads were pelleted and washed 2 times with lysis buffer (0.2% NP40, 50 mM Tris pH 8.0, 150 mM NaCl), 1 time with lysis buffer containing 0.2% SDS, 1 time with lysis buffer containing 500 mM NaCl and finally 1 time with $H_2O$. The beads were resuspended in Laemmli sample buffer (62.5 mM Tris pH 6.8, 2% SDS, 10% glycerol, 5% 2-mercaptoethanol, and 0.1 mg/ml bromophenol blue) and heated at 90° C. for 5 minutes. Supernatants were run on SDS-PAGE, fixed, dried and exposed as above.

I. Immunoreactivity with Sindbis and SFV-expressed GBV-C E2 Proteins

Results obtained by immunoblotting and RIPAs on the GBV-C proteins expressed in the Sindbis system were as follows: GBV-C E2 proteins expressed from pSin-ss/E2-222, pSin-ss/E2-315 and pSin-ss/E2-336 were detected in cell lysates and supernatants (indicating secretion from the cells) as analyzed by immunoblotting using the rabbit anti-GBV-C peptide and E. coli recombinant protein sera described in Example 3. GBV-C E2 protein expressed from pSin-ss/E2-289 was detected only in cell lysate, but not in supernatant.

Results obtained by immunoblotting and RIPAs on the GBV-C proteins expressed in the SFV system are summarized below:

GBV-C E2 proteins expressed from pSFV-ss/E2-222 and pSFV-ss/E2-336 were detected in cell lysates and supernatants (indicating secretion from the cells) as analyzed by immunoblotting using the rabbit anti-GBV-C E2 peptide sera and rabbit anti-E. coli GBV-C E2 recombinant protein serum described in Example 3. RIPAs were performed on pSFV-ss/E2-336 supernatant and lysate using the rabbit anti-E. coli GBV-C E2 recombinant protein serum and various human sera. The GBV-C E2 protein expressed from this construct was detected in both lysates and supernatants with the post-immune rabbit serum, but not with the pre-immune serum. It was also detected in lysates and supernatants with 2 GBV-C RT-PCR positive human sera found thus far to be seronegative against E. coli derived GBV-C proteins (as tested by ELISA as described in patent application Ser. No. 08/424,550 and with 4 GBV-C RT-PCR negative human sera previously found to be immunoreactive with E. coli derived GBV-C proteins.

Sera from 27 GBV-C RT-PCR negative intravenous drug users were tested in RIPAs using the pSFV-ss/E2-336 supernatant and all 27 were reactive with the E2 protein. It is known that this population is at very high risk of exposure to parenterally transmitted agents, as evidenced by the seroprevalence of antibodies to hepatitis C virus (99%) and hepatitis B virus (75%). Testing for hepatitis C virus was performed with an HCV EIA second generation assay, with confirmatory testing by synthetic peptides and the antibodies for hepatitis B core antigen were determined with the Corzyme® test (all available from Abbott Laboratories, North Chicago, Ill.). The seroprevalence level of antibody to GBV-C E2 protein indicated a similar level exposure to GBV-C in this population as to these other parenterally transmitted hepatitis agents.

Figure 6:
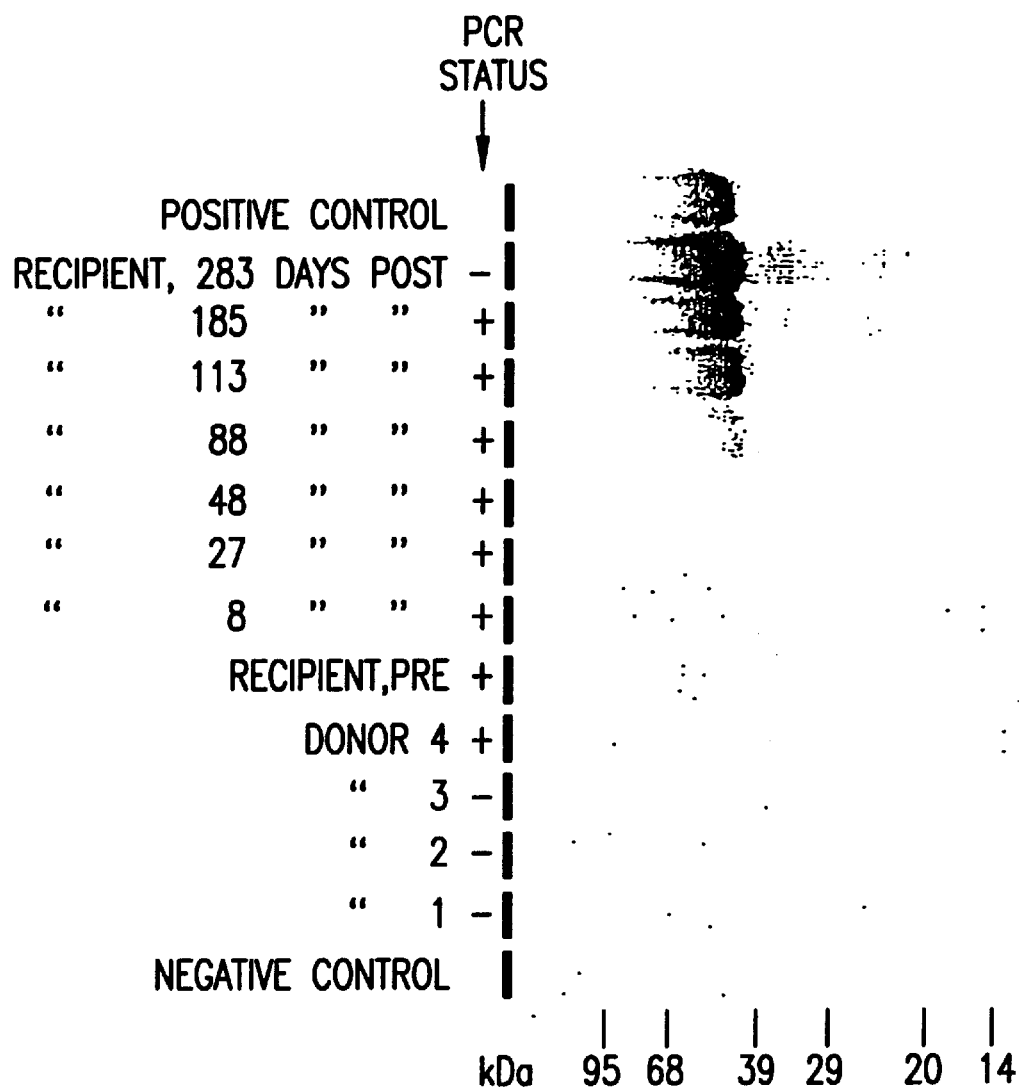
FIG. 6 is a photograph depicting the GBV-CE2 RIPA results of another individual infected with GBV-C.

RIPAs were performed with the pSFV-ss/E2-336 supernatant using serial bleeds from 7 patients who were all PCR negative for GBV-C prior to being transfused. Subsequent to transfusion with blood containing GBV-C, each of these 7 individuals developed elevated liver enzymes and became GBV-C RNA positive as detected by RT-PCR. The PCR and RIPA results from this study are summarized in TABLE 6. FIG. 6 shows the RIPA results from patient 2 (TABLE 6).

TABLE 6

| | SAMPLE | PCR STATUS | pSFV-ss/E2-336 RIPA STATUS | E2-315 ELISA S/N |
|---|---|---|---|---|
| Patient 1 | Donor | + | − | 0.80 |
| | Recipient, pre-inoculation | − | − | 0.80 |
| | Recipient, 10 days post-inoculation | − | − | 0.91 |
| | Recipient, 18 days post-inoculation | + | − | 0.86 |
| | Recipient, 33 days post-inoculation | + | − | 0.68 |
| | Recipient, 46 days post-inoculation | + | − | 0.92 |
| | Recipient, 104 days post-inoculation | + | − | 0.83 |
| | Recipient, 117 days post-inoculation | + | weak + | 1.28 |
| | Recipient, 154 days post-inoculation | + | + | 25.76 |
| | Recipient, 184 days post-inoculation | − | + | 27.07 |
| | Recipient, 207 days post-inoculation | − | + | 44.49 |

TABLE 6-continued

| | SAMPLE | PCR STATUS | pSFV-ss/E2-336 RIPA STATUS | E2-315 ELISA S/N |
|---|---|---|---|---|
| | Recipient, 284 days post-inoculation | − | + | 38.43 |
| Patient 2 | Donor 1 | − | − | 0.32 |
| | Donor 2 | − | − | 0.54 |
| | Donor 3 | − | − | 0.80 |
| | Donor 4 | + | − | 1.43 |
| | Recipient, pre-inoculation | − | − | 0.26 |
| | Recipient, 8 days post-inoculation | + | − | 0.34 |
| | Recipient, 27 days post-inoculation | + | − | 0.67 |
| | Recipient, 48 days post-inoculation | + | − | 0.80 |
| | Recipient, 88 days post-inoculation | + | weak + | 2.22 |
| | Recipient, 113 days post-inoculation | + | + | 6.55 |
| | Recipient, 185 days post-inoculation | + | + | 71.97 |
| | Recipient, 283 days post-inoculation | − | + | 79.79 |
| Patient 3 | Donor 1 | − | + | 9.88 |
| | Donor 2 | + | − | 0.76 |
| | Recipient, 6 days post-inoculation | − | − | 1.74 |
| | Recipient, 17 days post-inoculation | − | − | 1.63 |
| | Recipient, 33 days post-inoculation | − | − | 1.55 |
| | Recipient, 45 days post-inoculation | − | − | 1.05 |
| | Recipient, 62 days post-inoculation | − | − | 1.29 |
| | Recipient, 75 days post-inoculation | + | − | 1.32 |
| | Recipient, 90 days post-inoculation | + | − | 1.01 |
| | Recipient, 97 days post-inoculation | + | − | 1.12 |
| | Recipient, 151 days post-inoculation | + | − | 1.30 |
| | Recipient, 339 days post-inoculation | − | + | 31.32 |
| Patient 4 | Donor 1 | − | − | ND |
| | Donor 2 | + | − | ND |
| | Donor 3 | − | + | ND |
| | Recipient, pre-inoculation | − | − | ND |
| | Recipient, 8 days post-inoculation | − | − | ND |
| | Recipient, 15 days post-inoculation | + | − | ND |
| | Recipient, 43 days post-inoculation | + | − | ND |
| | Recipient, 64 days post-inoculation | + | − | ND |
| | Recipient, 85 days post-inoculation | + | − | ND |
| | Recipient, 125 days post-inoculation | + | − | ND |
| | Recipient, 145 days post-inoculation | + | − | ND |
| | Recipient, 173 days post-inoculation | + | − | ND |
| | Recipient, 278 days post-inoculation | − | + | ND |
| Patient 5 | Donor | + | − | 4.09 |
| | Recipient, pre-inoculation | − | weak + | 0.92 |
| | Recipient, 35 days post-inoculation | + | weak + | 1.43 |
| | Recipient, 80 days post-inoculation | + | + | 10.22 |
| | Recipient, 106 days post-inoculation | + | + | 14.67 |
| | Recipient, 134 days post-inoculation | − | + | 14.51 |
| | Recipient, 169 days post-inoculation | − | + | 10.09 |
| | Recipient, 184 days post-inoculation | − | + | 12.62 |
| | Recipient, 212 days post-inoculation | + | + | 10.53 |
| | Recipient, 239 days post-inoculation | − | + | 13.36 |
| | Recipient, 339 days post-inoculation | − | + | 12.17 |
| | Recipient, 428 days post-inoculation | − | + | 10.32 |
| | Recipient, 522 days post-inoculation | − | + | 7.33 |
| Patient 6 | Donor 1 | + | − | 0.39 |
| | Donor 2 | − | − | 0.43 |
| | Donor 3 | − | + | 11.79 |
| | Donor 4 | − | − | 0.49 |
| | Donor 5 | + | − | 0.79 |
| | Donor 6 | − | − | 1.00 |
| | Donor 7 | − | − | 0.76 |
| | Donor 8 | − | − | 0.57 |
| | Donor 9 | − | − | 0.58 |
| | Donor 10 | − | − | 0.46 |
| | Recipient, pre-inoculation | − | − | 1.18 |
| | Recipient, 14 days post-inoculation | − | weak + | 2.12 |
| | Recipient, 41 days post-inoculation | − | weak + | 1.54 |
| | Recipient, 68 days post-inoculation | − | − | 1.41 |
| | Recipient, 83 days post-inoculation | − | − | 1.53 |
| | Recipient, 89 days post-inoculation | + | − | 1.17 |
| | Recipient, 105 days post-inoculation | + | − | 0.97 |
| | Recipient, 118 days post-inoculation | + | − | 1.00 |
| | Recipient, 166 days post-inoculation | + | − | 1.24 |
| | Recipient, 280 days post-inoculation | + | + | 3.16 |
| Patient 7 | Donor 1 | − | − | 0.79 |
| | Donor 2 | − | − | 1.43 |
| | Donor 3 | + | − | 0.34 |
| | Donor 4 | + | − | 0.29 |
| | Recipient, pre-inoculation | − | − | 0.32 |

TABLE 6-continued

| SAMPLE | PCR STATUS | pSFV-ss/E2-336 RIPA STATUS | E2-315 ELISA S/N |
|---|---|---|---|
| Recipient, 16 days post-inoculation | + | − | 0.66 |
| Recipient, 44 days post-inoculation | + | − | 0.51 |
| Recipient, 85 days post-inoculation | + | − | 0.53 |
| Recipient, 127 days post-inoculation | + | − | 0.46 |
| Recipient, 161 days post-inoculation | + | − | 0.36 |
| Recipient, 265 days post-inoculation | + | − | 0.41 |

J. Results

Six of the 7 patients (patients 1–6) developed immunoreactivity against the GBV-C E2 protein during the study period, and all but one of these individuals (patient 6) was GBV-C RT-PCR negative by their last bleed date. Patients 6 and 7 were still GBV-C RT-PCR positive on the last date of sample availability and patient 7 exhibited no immunoreactivity to the GBV-C E2 protein.

These results indicate that, as has been found for other viruses including some flavi- and pesti-viruses, there may be a neutralizing epitope or epitopes found on the GBV-C E2 envelope protein which signifies or predicts that the viremic stage of infection is ending. The presence of antibodies to the E2 protein appears to be a good marker of recovery from GBV-C infection. In addition, this protein is a good candidate for potential vaccines to protect against exposure to GBV-C. Further, the vaccine could be used to treat chronically infected patients to assist in viral clearance. Moreover, the use of antisera harboring antibodies against this protein may be an efficacious treatment for patients infected with GBV-C who have not mounted an immune response sufficient to clear the virus, or to eliminate cells harboring E2 proteins. Such cells may contribute to tissue damage or even carcinogenesis.

Example 5

ELISA for Detection of Antibodies to GBV-C E2 315

A. Polystyrene Bead Coating Procedure

The GBV-C E2 315 expressed in CHO cells as described hereinabove in preceding examples was evaluated for antigenicity on polystyrene coated beads, and an enzyme-linked immunosorbent assay (ELISA) was developed for detecting antibodies to GBV-C E2. In the first study, one-quarter inch polystyrene beads were coated with purified protein (approximately 60 beads per lot) and evaluated in an ELISA test (described below). Briefly, polystyrene beads were coated with the purified proteins by adding the washed beads to a scintillation vial and immersing the beads (approximately 0.233 ml per bead) in a buffered solution containing the GBV-C E2 protein. The GBV-C E2 protein was approximately 125 ug/ml. The protein was diluted into bead coating buffer (0.1 M sodium phosphate pH 7.5) at 2 and 4 ug/ml. The vials were then placed on a rotating device in a 40° C. incubator for 2 hours, after which the fluids were aspirated and the beads were washed three times in phosphate buffered saline (PBS), pH 6.8. The beads were then treated with 0.1% Triton X-100® for 1 hour at 40° C. and washed three times in PBS. Next, the beads were overcoated with 5% bovine serum albumin and incubated at 40° C. for 1 hour with agitation. After additional washing steps with PBS, the beads were overcoated with 5% sucrose for 20 minutes at room temperature and the fluids were aspirated. Finally, the beads were air dried and then utilized for developing ELISA's for detection of antibodies to GBV-C E2.

B. ELISA Protocol for Detection of Antibodies to HGBV

An indirect assay format was utilized for the ELISA. Briefly, specimens (sera or plasma) being tested were diluted in specimen diluent (available from Abbott Laboratories, Abbott Park, Ill.) and reacted with a GBV-C E2 antigen coated solid phase (bead) having the GBV-C E2 antigen grown in CHO cells, all as described hereinabove. After a washing step, the beads were reacted with horseradish-peroxidase (HRPO) labeled antibodies directed against human immunoglobulins to detect human antibodies bound to the solid phase. Specimens which produced signals above a cutoff value were considered reactive. Additional details pertaining to the ELISA's are described below.

The format for the ELISAs entailed contacting the GBV-C E2 antigen-coated solid phase (prepared in CHO cells as described hereinabove and coated on beads as described hereinabove) with human serum pre-diluted in specimen diluent (buffered solution containing animal sera and non-ionic detergents, available from Abbott Laboratories, Abbott Park, Ill.). This specimen diluent was formulated to reduce background signals obtained from non-specific binding of immunoglobulins to the solid phase while enhancing the binding of specific antibodies to the antigen-coated solid phase. Specifically, 10 µl of human serum was diluted in 150 µl of specimen diluent and vortexed. Ten microliters of this pre-diluted specimen was then added to the well of a reaction tray, followed by the addition of 200 µl of specimen diluent and an antigen coated polystyrene bead. The reaction tray was then incubated in a Dynamic Incubator (Abbott Laboratories, Abbott Park, Ill.) set for constant agitation at room temperature. After a 1 hour incubation, the fluids were aspirated, and the wells containing the beads were washed three times in distilled water (5 ml per wash). Next, 200 µl of HRPO-labeled goat anti-human immunoglobulin (available from Kirkegaard and Perry, Gaithersburg, Md.) diluted in a conjugate diluent (buffered solution containing animal sera and non-ionic detergents, available from Abbott Laboratories, Abbott Park, Ill.) was added to each well and the reaction tray was incubated again as described hereinabove for 1 hour. The fluids then were aspirated, and the wells containing the beads were washed three times in distilled water as described above. The beads containing complexed antigen and bound immunoglobulins were removed from the wells, each bead was placed in a test tube and reacted with 300 µl of a solution of 0.3% o-phenylenediamine-2 HCl in 0.1 M citrate buffer (pH 5.5) with 0.02% $H_2O_2$ (available from Abbott Laboratories, Abbott Park, Ill.). After incubation for 30 minutes at room temperature, the reaction was terminated by the addition of 1 N $H_2SO_4$. The absorbance at 492 nm was read on a spectrophotometer. The color produced was directly proportional to the amount of antibody present in the test sample.

A small panel was tested to determine whether the GBV-C E2 ELISA might be useful. Serum from volunteer donors who were prescreened as negative for GBV-C RNA by RT-PCR and negative for GBV-C proteins tested in other ELISAs utilizing proteins other than GBV-C E2 proteins were used as the negative controls. Positive controls included specimens identified as having antibodies to GBV-C E2 either by Western blotting (as described in Example 3F) or by SDS-PAGE RIPA on GBV-C E2 pSFV-ss/E2-336 proteins (as described in Example 4I). The results obtained with these first coated beads indicated that low absorbance values were obtained with the presumed negative controls and higher absorbance values were noted for the specimens which were presumed to contain antibodies to GBV-C E2. Further experiments then were undertaken.

C. Separation of GBV-E2 Protein from Free FLAG Peptides

The first preparation of GBV-C E2 315 purified protein used to coat beads was likely to also contain free FLAG peptide used for elution from the anti-FLAG M2 affinity column. Since the possibility existed that FLAG peptide might interfere with the ability of the GBV-C E2 protein to coat the solid phase, the protein was further purified for the scaled-up bead coating procedure to remove the free FLAG. This was performed using Sephadex G-25® as described above.

D. Utility of GBV-C E2 ELISA

The bead coating was scaled up to 500 beads utilizing the same procedure described above. Five hundred beads coated with the E2-315 protein were prepared as described hereinabove and utilized in ELISA testing as described hereinabove. The results were as follows.

Figure 3:
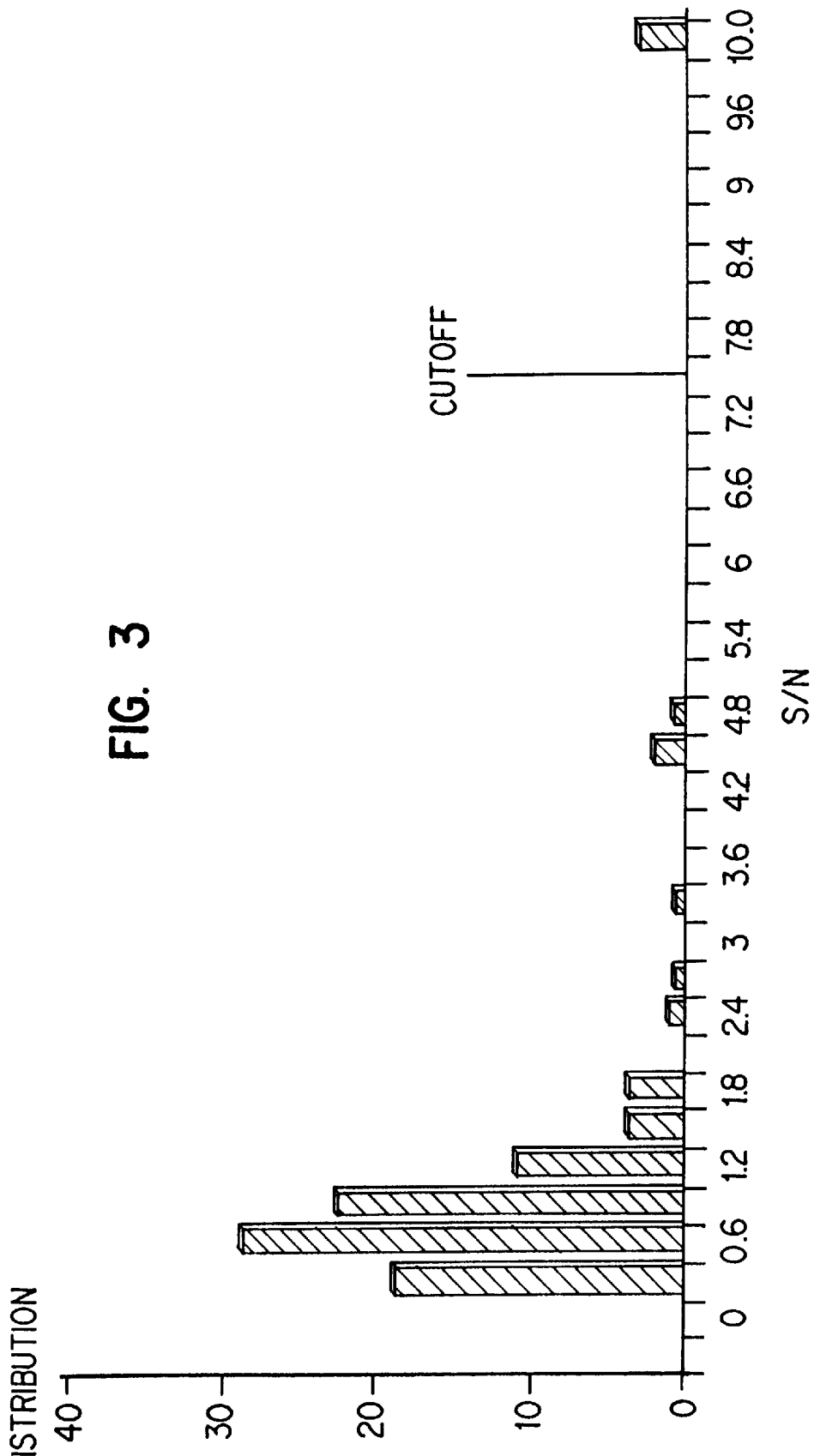
FIG. 3 presents a graphic of anti-GBV-C E2 reactivity of 100 volunteer blood donors demonstrating the distribution for determining the preliminary cutoff.

1. Volunteer Blood Donors. A population of 100 volunteer blood donors assumed to be at "low risk" for exposure to GBV-C were tested for antibodies to GBV-C E2 utilizing the GBV-C E2 ELISA. (These specimens were considered as low risk since the serum had been screened as negative for evidence of active infection with known hepatotropic agents (hepatitis B virus [HBV], hepatitis C virus [HCV]) utilizing appropriate tests (hepatitis B surface antigen test, anti-HCV test, available from Abbott Laboratories, Abbott Park, Ill.) and were screened as having normal serum alanine aminotransferase levels (ALT), suggesting that there was no current evidence of active liver disease). Three specimens among the 100 samples tested had relatively high absorbance values and were considered as likely to contain antibodies to GBV-C E2. The other 97 specimens had relatively low absorbance values and appeared to represent a typical profile of seronegative individuals. A preliminary cutoff was determined by calculating the population mean of the 97 negative specimens and determining the standard deviation (FIG. 3). The cutoff was determined as the sum of the population mean and seven standard deviations from the population mean. Utilizing this cutoff, three of the volunteer blood donors were positive for antibodies to GBV-C E2. In general, the cutoff corresponded to sample to negative control ratio (S/N) of 7.5.

Figure 4:
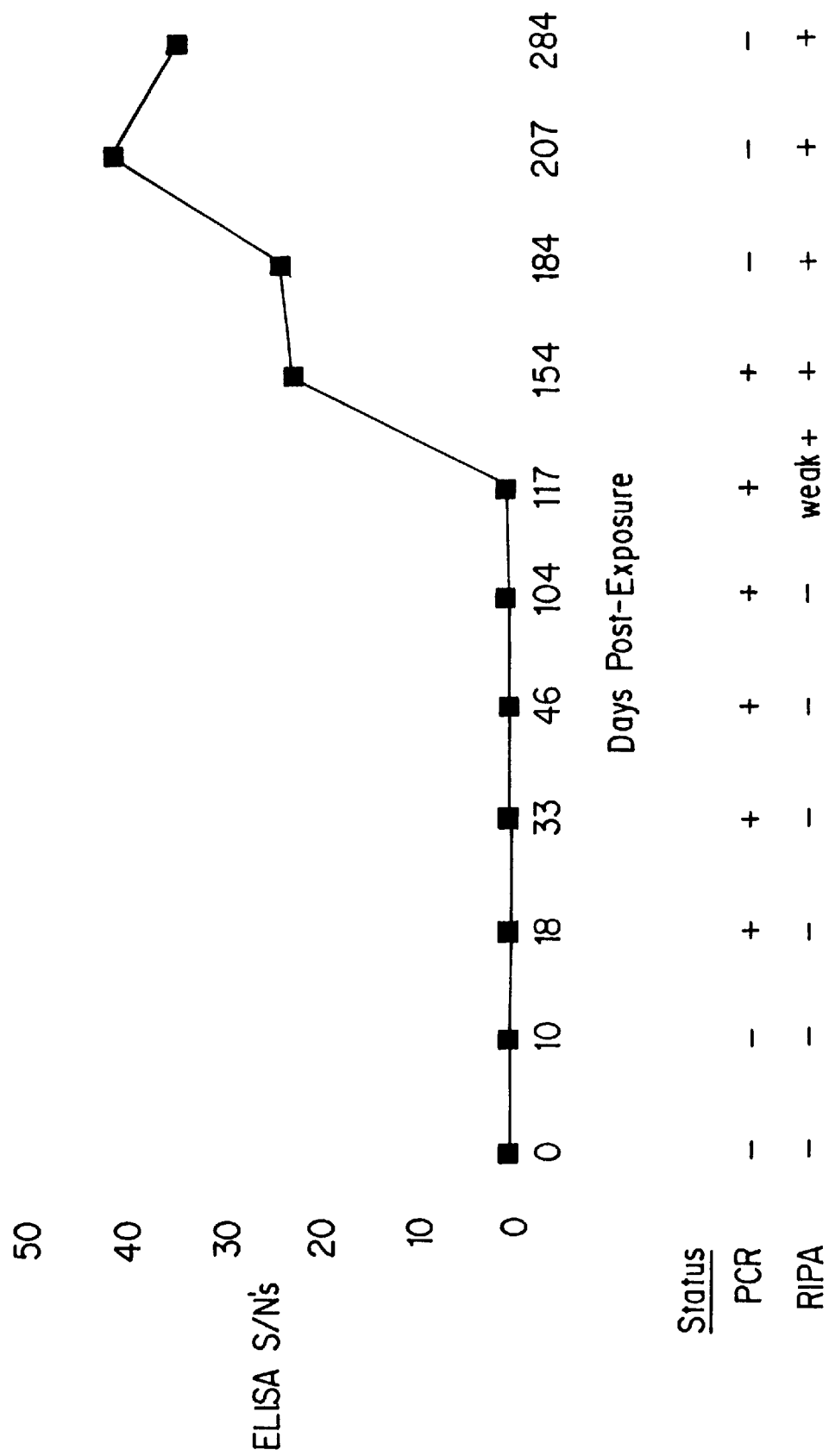
FIG. 4 is a graph of a serological profile of an individual acutely infected with GBV-C wherein the GBV-CE2 ELISA's S/N is plotted against days post exposure, and the GBV-C PCR and GBV-CE2 RIPA reactivities corresponding to the days post exposure are presented.
Figure 5:
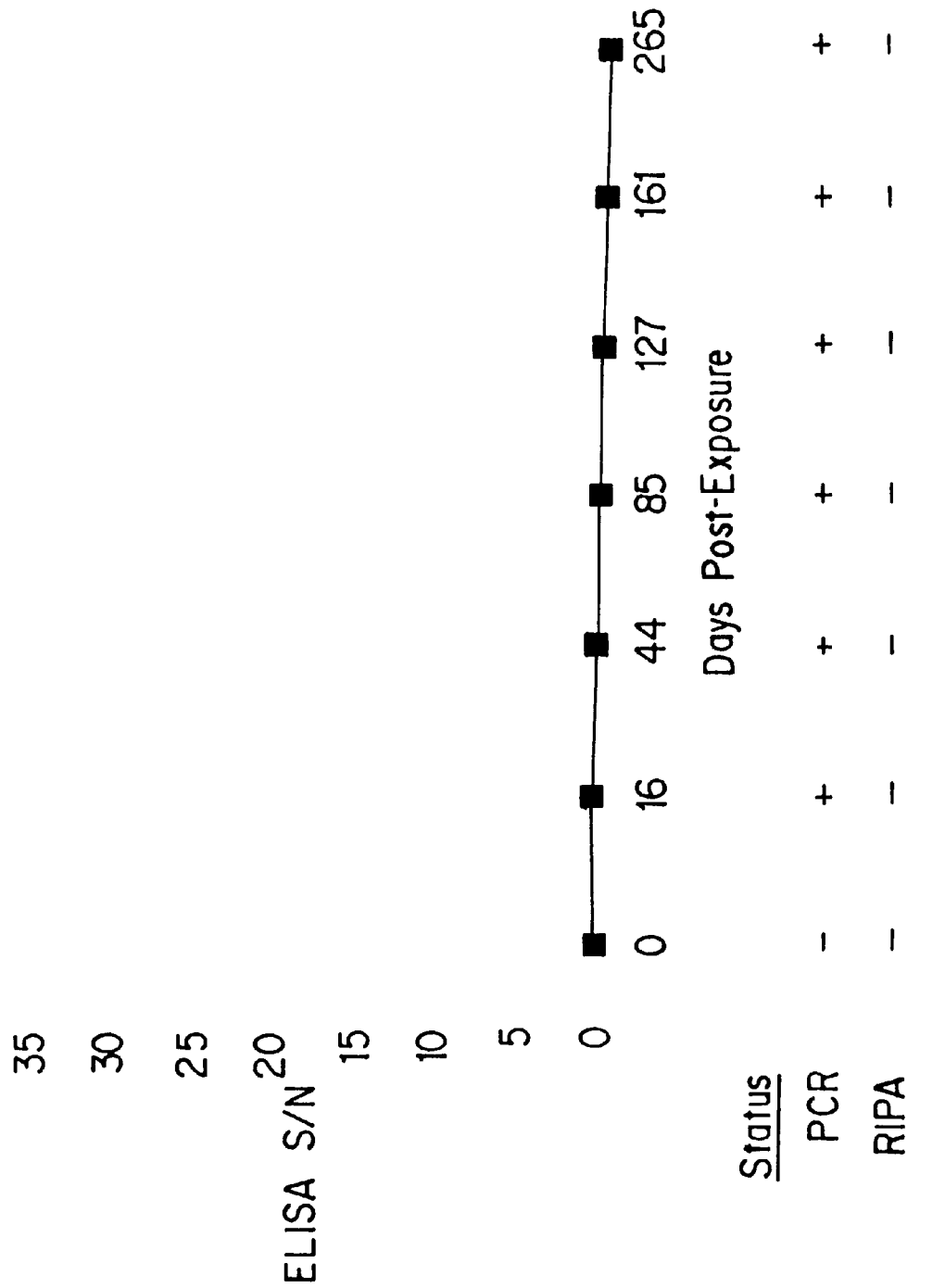
FIG. 5 is a graph of a serological profile of an individual acutely infected with GBV-C wherein the GBV-CE2 ELISA's S/N is plotted against days post exposure, and the GBV-C PCR and RIPA GBV-CE2 reactivities corresponding to the days post exposure are presented.

2. GBV-C RNA Positive Blood Transfusion Recipients. Serial specimens were obtained from several individuals who were exposed to GBV-C via blood transfusion. In all cases, each individual was negative for GBV-C RNA by RT-PCR prior to transfusion and became GBV-C RNA positive following transfusion with blood from at least one GBV-C RNA positive blood donor. A typical profile showing the PCR reactivity and the ELISA values is depicted in FIG. 4. This individual (Patient #1 in TABLE 6) was PCR negative for GBV-C RNA prior to exposure to GBV-C and on day 10 post exposure. GBV-C RNA was detected on days 18, 33, 46, 104, 117 and 154 post exposure. Antibodies to GBV-C E2 were first detected by RIPA against the GBV-C E2-336 protein generated via the SFV vector (described in Example 4J, above) on day 117 post exposure and continued to be detected on all follow-up specimens (days 154, 184, 207 and 284 post exposure). The GBV-C E2 ELISA detected antibodies to GBV-C E2 on days 154, 184, 207 and 284 post exposure. These data suggest that the antibodies to GBV-C E2 are associated with viral clearance and further suggest that, once antibodies to GBV-C E2 are present, the individual's viremia will resolve in a short period of time. An example of a second profile from a second individual is depicted in FIG. 5. This individual (Patient #7 in TABLE 6) was negative for GBV-C RNA prior to transfusion, became GBV-C RNA positive on day 16 and remained PCR positive on all of the follow-up specimens (days 44, 85, 127, 161 and 265 post exposure). No antibody response was noted either by the ELISA or RIPA. These data support the hypothesis that antibodies to GBV-C E2 must be generated in order to clear GBV-C virus from the bloodstream.

3. Other Sera. Several other different classifications of individuals were tested for antibodies to GBV-C E2. These data are presented in TABLE 7. As noted previously, only three of 100 volunteer blood donors were antibody positive in the GBV-C E2 ELISA test. In stark contrast, however, 25 of 25 Intravenous drug users (IVDU's) who were negative for GBV-C RNA were antibody positive in the ELISA. These data indicate that the IVDU's indeed represent a population of individuals who are now conclusively shown to be "at high risk" for exposure to GBV-C. Previous studies had indicated that GBV-C RNA can be detected in about 15% of IVDU's. Combined, the PCR data and antibody data indicate that within the limits of the study, 100% of the IVDU's from this cohort have been exposed to GBV-C. Further, four of 20 West Africans who were GBV-C RNA negative were antibody positive in the GBV-C E2 ELISA. (Previous data had indicated that GBV-C RNA was detected in 10–15% of the West African residents; these antibody results indicate that the exposure to GBV-C is actually much higher than noted with the GBV-C RNA studies alone). Moreover, among 50 PCR positive individuals from different patient categories (IVDU's, West Africans, non A–E hepatitis patients), only seven of the 50 (14.0%) were antibody positive to GBV-C. These data lend additional support to previous studies which indicated that antibodies to GBV-C E2 may be more readily detected in individuals recovering or having recovered from GBV-C infection.

TABLE 7

Preliminary Anti-GBV-C E2 Prevalence in Various Groups

| Category | Number Tested | Number Positive | Percentage |
| --- | --- | --- | --- |
| Volunteer Blood Donors PCR Negative Individuals | 100 | 3 | 3.0 |
| Intravenous Drug Users | 25 | 25 | 100.0 |
| West African Residents | 20 | 4 | 20.0 |
| PCR Positive Individuals | 50 | 7 | 14.0 |

Example 6

Expression of GBV-C Polypeptides Using a Baculovirus Vector System

A. Baculovirus Transfer Vector Construction

A transfer vector for the expression of GBV-C E2 protein was constructed by restricting pAcGP67A with both Bam HI and Pst I restriction endonucleases. A GBV-C E2 gene fragment with compatible Bam HI and Pst I ends was generated by PCR as described supra using a plasmid template containing a portion of GBV-C. Vector assembly was performed by standard methods known to those skilled in the art and termed pAcGP67A/E2C. The fragment encoded a 336 amino acid segment of the GBV-C E2 gene (amino acids 221 to 556 of SEQUENCE I.D. NO. 35). Contained within the sense PCR primer sequence (SEQUENCE I.D. NO. 68) was a Bam HI site, followed immediately by nucleotides corresponding to template sequences encoding amino acids starting at residue 221 of GBV-C. The antisense PCR primer (SEQUENCE I.D. NO. 69) contained nucleotides complementary to template sequences that encode amino acids ending at residue 556 of GBV-C, followed by a sequence encoding the 8 amino acids Asp-Tyr-Lys-Asp-Asp-Asp-Asp-Lys (see anti-FLAG recognition site supra), two stop codons and a Pst I restriction enzyme site compatible with the cloning vector.

B. Transfection and Amplification of Recombinant Baculovirus

The transfer vector described above was transfected into shaker flask adapted Sf9 cells (available from Gibco-BRL; Grand Island, N.Y.) using the BaculoGold™ Transfection Kit (PharMingen). Briefly, 3 ml of Sf9 cells diluted to $1 \times 10^6$/ml in Sf-900 II SFM medium (Gibco-BRL) were dispensed into T25 cell culture flasks. After being allowed to adhere at room temperature for 10 minutes, medium was removed and 1 ml of Buffer A (obtained from the BaculoGold™ Transfection Kit described hereinabove) was added. 4 µg of pAcGP67A-E2C was mixed with 0.5 µg BaculoGold DNA and 1 ml of Buffer B (obtained from the BaculoGold™ Transfection Kit described hereinabove). After 5 minutes at room temperature, DNA mix was added drop-by-drop to the Sf9 cells in Buffer A. Cultures were incubated at 28° C. for 4 hours, at which time the precipitate was removed, the cells were washed with Sf-900 II SFM and cultured with 3 ml of fresh medium at 28° C. After 4 days, 0.5 ml of the transfected cell supernatant was added to Sf9 cells to expand the concentration of recombinant virus. Upon observing viral CPE, both cells and cell supernatants were evaluated for successful expression of the recombinant protein. It was observed that both cells and cell supernatants contained a band of approximately 40–50 kD that was immunoreactive with anti-FLAG BioM2 monoclonal antibody (Eastman Kodak Co., New Haven, Conn.) reactive with the 8 amino acid FLAG peptide engineered to the carboxyl-terminus. Additionally, this band was reactive with sera from rabbits immunized with an *E. coli* derived GBV-C E2 antigen or with a synthetic peptide "GE2-1" having the amino acid sequence "QGAPASVLGSRPFE" (SEQUENCE ID NO. 70) corresponding to sequences within GBV-C E2. Recombinant virus was plaque-purified in Sf9 cells under an agarose-overlay using methods known to those skilled in the art. Plaque-pure viruses were isolated and expanded in Sf9 cells as described hereinabove, from which high-titered stocks were made (Invitrogen, San Diego, Calif.). Titering was conducted with Sf9 cells utilizing standard methodologies, and stocks were stored at 4° C. Analysis and purification of GBV-C E2 was performed as described supra.

D. Maintenance and Storage of Cell Lines

Sf9 cells maintained in culture or being used for infection purposes were passaged twice weekly in Sf-900 II SFM medium. Cells were diluted to $3-4 \times 10^5$/ml (100 ml volumes) in 250 ml shaker flasks and incubated at 28° C. on a shaker platform rotating at 150 rpm. Cryostorage was by resuspension of $1 \times 10^7$ cells into 1.0 ml of Sf-900 II SFM medium supplemented with 10% FBS (Sigma Chem. Co., St. Louis, Mo.) and 7.5% DMSO (Sigma) and cold storage for 24–48 hours at −80° C. Permanent storage was in liquid nitrogen.

Strains replicated from the HGBV nucleic acid sequence library have been deposited at the American Type Culture Collection, 12301 Parklawn Drive, Rockville, Md. 20852, as of May 31, 1996, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone pSinRep5/NS5A was accorded A.T.C.C. deposit No. 98073; Clone pCHO/E2-336 was accorded A.T.C.C. deposit No. CRL12111; Clone pSFV-ss/E2-336 was accorded A.T.C.C. deposit No. 98070; Clone pSFV-ss/NS3 was accorded A.T.C.C. deposit No. 98071; Clone pCHO/E2-315 was accorded A.T.C.C. deposit No. CRL12110; and Clone pAcGP67A-E2C was accorded A.T.C.C. deposit No. 98072.

The present invention is intended to be limited only by the appended claims.

What is claimed is:

1. An assay kit for determining the presence of hepatitis GB virus (HGBV) E2 antigen or antibody in a test sample comprising a container containing a polypeptide possessing at least one HGBV epitope of an HGBV E2 antigen, wherein said kit detects only HGBV E2 antigen or antibody present in said test sample and no other HGV antigens or antibodies in said test sample.

2. The assay kit of claim 1 wherein said polypeptide is attached to a solid phase.

3. The assay kit of claim 1 wherein said polypeptide is attached to a signal generating compound which generates a measurable signal.

4. The assay kit of claim 3 wherein said signal generating compound is selected from the group consisting of an enzyme, a fluorescent compound, and a chemiluminescent compound.

5. The assay kit of claim 4 wherein said polypeptide is produced by recombinant technology.

6. The assay kit of claim 5 wherein said polypeptide is a fusion polypeptide.

7. The assay kit of claim 1 wherein said polypeptide is produced from a plasmid selected from the group consisting of pCHO/E2-336, pSFV-ss/E2-336, pCHO/E2-315, and pAcGP67-E2C.

8. A method for detecting hepatitis GB virus (HGBV) E2 antibodies in a test sample suspected of containing said E2 antibodies, comprising:

(a) contacting said test sample with a polypeptide of HGBV E2 antigen, for a time and under conditions sufficient to allow antigen/antibody complexes to form; and (b) detecting said complexes which contain the polypeptide, wherein said method detects only HGBV E2 antibodies in said test sample and no other HGV antibodies in said test sample.

9. The method of claim 8 wherein said polypeptide is atttached to a solid phase.

10. The method of claim 9, wherein said solid phase is selected from the group consisting of beads, microtiter wells, walls of a test tube, nitrocellulose strips, magnetic beads, and nonmagnetic beads.

11. The method of claim 10 further comprising the step of contacting said complexes of step (a) with an indicator reagent comprising a signal generating compound which generates a measurable signal, for a a time and under conditions sufficient to allow antigen/antibody/indicator reagent complexes to form prior to performing step (b).

12. The method of claim 11, wherein said signal generating compound is selected from the group consisting of an enzyme, a fluorescent compound, and a chemiluminescent compound.

13. The method of claim 12 wherein said polypeptide is produced by recombinant technology.

14. The method of claim 13 wherein said polypeptide is a fusion polypeptide.

15. The method of claim 8 wherein said polypeptide is produced from a plasmid selected from the group consisting of pCHO/E2-336, pSFV-ss/E2-336, pCHO/E2-315, and pAcGP67-E2C.

16. A method for determining the clearance of hepatitis GB virus (HGBV) E2 antigen from a patient infected with HGBV, comprising:

(a) contacting a test sample obtained from said patient with a HGBV E2 polypeptide, for a time and under conditions sufficient to allow antigen/antibody complexes to form; and (b) detecting said complexes, wherein the presence of said complexes is an indication of the clearance of said HGBV E2 antigen from said patient.

17. The method of claim 16 wherein said polypeptide is attached to a solid phase.

18. The method of claim 17, where in said solid phase is selected from the group consisting of beads, micreotiter wells, walls of a test tube, nitrocellulose strips, magnetic beads, and nonmagnetic beads.

19. The method of claim 18, further comprising the step of contacting said complexes of step (a) with an indicator reagent comprising a signal generating compound which generates a measurable signal, for a a time and under conditions sufficient to allow antigen/antibody/indicator reagent complexes to form prior to performing step (b).

20. The method of claim 19, wherein said signal generating compound is selected from the group consisting of an enzyme, a fluorescent compund, and a chemiluminescent compound.

21. The method of claim 20 wherein said polypeptide is produced by recombinant technology.

22. The method of claim 21 wherein said polypeptide is a fusion polypeptide.

23. The method of claim 16 wherein said polypeptide is produced from a plasmid selected from the group consisting of pCHO/E2-336, pSFV-ss/E2-336, pCHO/E2-315, and pAcGP67-E2C.

24. Plasmid pCHO/E2-336, having A.T.C.C. deposit No. CRL-12111.

25. Plasmid pSFV-ssE2-336, having A.T.C.C. deposit No. 98070.

26. Plasmid pCHO/E2-315, having A.T.C.C. deposit No. CRL-12110.

27. Plasmid pAcGP67A-E2C, having A.T.C.C. deposit No. 98072.

* * * * *

UNITED STATES PATENT AND TRADEMARK OFFICE
CERTIFICATE OF CORRECTION

PATENT NO. : 6,156,495  
DATED : December 5, 2000  
INVENTOR(S) : Tami J. Pilot-Matias et al.

Page 1 of 1

It is certified that error appears in the above-identified patent and that said Letters Patent is hereby corrected as shown below:

<u>Column 140,</u>
Line 25, replace "signal, for a a time and under" with -- signal, for a time and under --.
Line 59, replace "for a a time and under" with -- for a time and under --.
Line 64, replace "enzyme, a fluorescent compund," witn -- enzyme, a fluorescent compound, --.

Signed and Sealed this

Twenty-ninth Day of January, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GGAAAAGGAT CCCGGCTTGT GTCCAAGATG TGCG                                    34
```

(2) INFORMATION FOR SEQ ID NO:2:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
GGGGAAAAGC TTAAGCCTTA GTGACCCCGA GGAAG                                   35
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GGGGAAGAAT TCGGAAAGGG CTTCCTCGGG GT                                      32
```

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GGCGGCAAGC TTACACGTCC AGTTCTACCT TGTCCC                                  36
```

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GGAAAAGGAT CCAGCAAGGG GGACAAGGTA GA                                      32
```

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GGGGAAAAGC TTACATGGCC CTCACAGTGG CAA                                     33
```

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGAAAAGGAT CCAACCCGTC GGTTGCCACT GTGA                         34

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGCGGCAAGC TTAGTCCAGC TTTGTCTCAA TTATGG                       36

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGAAAAGGAT CCCATCCATC CATAATTGAG AC                           32

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGGGAAAAGC TTAAGGGACA GTCCGCAAGG AAAT                         34

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGTTTTGGAT CCACCATTAC CATTTCCTTG CGGAC                        35

(2) INFORMATION FOR SEQ ID NO:12:

(i) SEQUENCE CHARACTERISTICS:
        (A) LENGTH: 36 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:12:

GGGAAAAAGC TTACCAATTG ACGCCGCGAA CTTTTG                                      36

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGGAAAGGAT CCAGCTGGGC AAAAGTTCGC GGCGGCG                                     37

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGCGGCAAGC TTAAAGGGGA TTGCCACCTC CCTTC                                       35

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GGAAAAGGAT CCTGGGATGT GAAGGGAGGT GGC                                         33

(2) INFORMATION FOR SEQ ID NO:16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGCGGAAAGC TTAACCCCCG GCGAAGAGCT TGTCAAC                                     37

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGTTTTGGAT CCTCAATTGT TGACAAGCTC TTCG                                           34

(2) INFORMATION FOR SEQ ID NO:18:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:18:

GGCGGAAAGC TTAAAGGTCT TCTGTTGAAA GTTTCC                                         36

(2) INFORMATION FOR SEQ ID NO:19:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:19:

GGAAAAGGAT CCATGGCTGG GAAACTTTCA ACAG                                           34

(2) INFORMATION FOR SEQ ID NO:20:

(i) SEQUENCE CHARACTERISTICS:
             (A) LENGTH: 37 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:20:

GGGGAAAAGC TTATCTAGAC ATCACCATGC GCACCTC                                        37

(2) INFORMATION FOR SEQ ID NO:21:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:21:

GGAAAAGGAT CCATGCGCCA GGTGCGCATG GTGATG                                         36

(2) INFORMATION FOR SEQ ID NO:22:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:22:

GGGGAAAAAA GCTTAGATCA CCACGTGGGT AGGGGTCAC                                      39

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GGAAAAGGAT CCGTGGTGGT GACCCCTACC CAC                    33

(2) INFORMATION FOR SEQ ID NO:24:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GGCGGCAAGC TTATCTCGCA GCATTCTCTA TCGC                   34

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GGAAAAGGAT CCGCCCTCCA AGCGATAGAG AATG                   34

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GGCGGCAAGC TTACTTAACC GTTAGCTTTC GTG                    33

(2) INFORMATION FOR SEQ ID NO:27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GGAAAAGGAT CCAGCGATGC CACACGAAAG CTAAC                  35

(2) INFORMATION FOR SEQ ID NO:28:

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GGGGAAAAGC TTAGGTGGTG TCTGCCACCA ACAAG                          35

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:29:

CTCGTATGAT GCGACAGTCC GTCC                                      24

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:30:

GATTATGGCC TTTGTGCTTC CACCC                                     25

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:31:

GCATCGAGAT CGGGACGGAG ACTG                                      24

(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:32:

GAATGTGACA AGTGTGAGGC ACG                                       23

(2) INFORMATION FOR SEQ ID NO:33:

(i) SEQUENCE CHARACTERISTICS:
        (A) LENGTH: 2905 amino acids
        (B) TYPE: amino acid
        (D) TOPOLOGY: linear
```

(ii) MOLECULE TYPE: protein (xi) SEQUENCE DESCRIPTION: SEQ ID NO:33:

```
Pro Ile Gly Val Arg Arg Val Asp Lys Asp Gln Trp Gly Pro Gly Gly
 1               5                  10                  15

Arg Gly Lys Asp Pro His Arg Cys Pro Ser Arg Gly Gly Lys Cys
             20                  25                  30

Met Gly Pro Pro Ser Ser Ala Ala Tyr Ser Arg Gly Ser Pro Arg
         35                  40                  45

Thr Ser Gly Glu Gly Gly Trp His Phe Phe Ser Tyr Thr Asp His Gly
     50                  55                  60

Ser Pro Ser Ala Pro Thr Arg Gly Gly Ala Gly Ala Ile Leu Ala Pro
 65                  70                  75                  80

Ala Thr His Ala Cys Ser Ala Lys Gly Gln Tyr Xaa Leu Thr Asn Cys
                 85                  90                  95

Cys Ala Leu Glu Asp Ile Gly Phe Cys Leu Glu Gly Gly Cys Leu Val
                100                 105                 110

Ala Leu Gly Cys Thr Ile Cys Thr Asp Arg Cys Trp Pro Leu Tyr Gln
            115                 120                 125

Ala Gly Leu Ala Val Arg Pro Gly Lys Ser Ala Ala Gln Leu Val Gly
        130                 135                 140

Glu Leu Gly Ser Leu Tyr Gly Pro Leu Ser Val Ser Ala Tyr Val Ala
145                 150                 155                 160

Gly Ile Leu Gly Leu Gly Glu Val Tyr Ser Gly Val Leu Thr Val Gly
                165                 170                 175

Val Ala Leu Thr Arg Arg Val Tyr Pro Val Pro Asn Leu Thr Cys Ala
                180                 185                 190

Val Glu Cys Glu Leu Lys Trp Glu Ser Glu Phe Trp Arg Trp Thr Glu
            195                 200                 205

Gln Leu Ala Ser Asn Tyr Trp Ile Leu Glu Tyr Leu Trp Lys Val Pro
        210                 215                 220

Phe Asp Phe Trp Arg Gly Val Met Ser Leu Thr Pro Leu Leu Val Cys
225                 230                 235                 240

Val Ala Ala Leu Leu Leu Glu Gln Arg Ile Val Met Val Phe Leu
                245                 250                 255

Leu Val Thr Met Ala Gly Met Ser Gln Gly Ala Pro Ala Ser Ser Val
                260                 265                 270

Gly Val Thr Ala Phe Arg Gly Gly Phe Asp Leu Ala Val Leu Phe Leu
            275                 280                 285

Gln Val Glu Arg Val Pro Arg Ala Asp Arg Glu Arg Val Trp Glu Arg
        290                 295                 300

Gly Asn Val Thr Leu Leu Cys Asp Cys Pro Asn Gly Pro Trp Val Trp
305                 310                 315                 320

Val Pro Ala Leu Cys Gln Ala Ile Gly Trp Gly Asp Pro Ile Thr His
                325                 330                 335

Trp Ser His Gly Gln Asn Gln Trp Pro Leu Ser Cys Pro Gln Phe Val
                340                 345                 350

Tyr Gly Ala Val Ser Val Thr Cys Val Trp Gly Ser Val Ser Trp Phe
            355                 360                 365

Ala Ser Thr Gly Gly Arg Asp Ser Lys Val Asp Val Trp Ser Leu Val
        370                 375                 380

Pro Val Gly Ser Ala Ser Cys Thr Ile Ala Ala Leu Gly Ser Ser Asp
385                 390                 395                 400
```

```
Arg Asp Thr Val Val Glu Leu Ser Glu Trp Gly Ile Pro Cys Ala Thr
            405                 410                 415
Cys Ile Leu Asp Arg Arg Pro Ala Ser Cys Gly Thr Cys Val Arg Asp
            420                 425                 430
Cys Trp Pro Glu Thr Gly Ser Val Arg Phe Pro Phe His Arg Cys Gly
            435                 440                 445
Ala Gly Pro Arg Leu Thr Arg Asp Leu Glu Ala Val Pro Phe Val Asn
            450                 455                 460
Arg Thr Thr Pro Phe Thr Ile Arg Gly Pro Leu Gly Asn Gln Gly Arg
465                 470                 475                 480
Gly Asn Pro Val Arg Ser Pro Leu Gly Phe Gly Ser Tyr Thr Met Thr
            485                 490                 495
Lys Ile Arg Asp Ser Leu His Leu Val Lys Cys Pro Thr Pro Ala Ile
            500                 505                 510
Glu Pro Pro Thr Gly Thr Phe Gly Phe Pro Gly Val Pro Pro Leu
            515                 520                 525
Asn Asn Cys Met Leu Leu Gly Thr Glu Val Ser Glu Val Leu Gly Gly
            530                 535                 540
Ala Gly Leu Thr Gly Gly Phe Tyr Glu Pro Leu Val Arg Arg Cys Ser
545                 550                 555                 560
Glu Leu Met Gly Arg Arg Asn Pro Val Cys Pro Gly Phe Ala Trp Leu
            565                 570                 575
Ser Ser Gly Arg Pro Asp Gly Phe Ile His Val Gln Gly His Leu Gln
            580                 585                 590
Glu Val Asp Ala Gly Asn Phe Ile Pro Pro Pro Arg Trp Leu Leu Leu
            595                 600                 605
Asp Phe Val Phe Val Leu Leu Tyr Leu Met Lys Leu Ala Glu Ala Arg
            610                 615                 620
Leu Val Pro Leu Ile Leu Leu Leu Trp Trp Val Asn Gln Leu
625                 630                 635                 640
Ala Val Leu Xaa Val Xaa Ala Xaa Xaa Ala Ala Val Ala Gly Glu Val
            645                 650                 655
Phe Ala Gly Pro Ala Leu Ser Trp Cys Leu Gly Leu Pro Phe Val Ser
            660                 665                 670
Met Ile Leu Gly Leu Ala Asn Leu Val Leu Tyr Phe Arg Trp Met Gly
            675                 680                 685
Pro Gln Arg Leu Met Phe Leu Val Leu Trp Lys Leu Ala Arg Gly Ala
            690                 695                 700
Phe Pro Leu Ala Leu Leu Met Gly Ile Ser Ala Thr Arg Gly Arg Thr
705                 710                 715                 720
Ser Val Leu Gly Ala Glu Phe Cys Phe Asp Val Thr Phe Glu Val Asp
            725                 730                 735
Thr Ser Val Leu Gly Trp Val Val Ala Ser Val Val Ala Trp Ala Ile
            740                 745                 750
Ala Leu Leu Ser Ser Met Ser Ala Gly Gly Trp Lys His Lys Ala Ile
            755                 760                 765
Ile Tyr Arg Thr Trp Cys Lys Gly Tyr Gln Xaa Leu Arg Gln Arg Val
            770                 775                 780
Val Arg Ser Pro Leu Gly Glu Gly Arg Pro Thr Lys Pro Leu Thr Ile
785                 790                 795                 800
Ala Trp Cys Leu Ala Ser Tyr Ile Trp Pro Asp Ala Val Met Leu Val
            805                 810                 815
```

-continued

```
Val Val Ala Met Val Leu Leu Phe Gly Leu Phe Asp Ala Leu Asp Trp
            820                 825                 830

Ala Leu Glu Glu Leu Leu Val Ser Arg Pro Ser Leu Arg Arg Leu Ala
            835                 840                 845

Arg Val Val Glu Cys Cys Val Met Ala Gly Glu Lys Ala Thr Thr Val
            850                 855                 860

Arg Leu Val Ser Lys Met Cys Ala Arg Gly Ala Tyr Leu Phe Asp His
865                 870                 875                 880

Met Gly Ser Phe Ser Arg Ala Val Lys Glu Arg Leu Leu Glu Trp Asp
                885                 890                 895

Ala Ala Leu Glu Xaa Leu Ser Phe Thr Arg Thr Asp Cys Arg Ile Ile
            900                 905                 910

Arg Asp Ala Ala Arg Thr Leu Ser Cys Gly Gln Cys Val Met Gly Leu
            915                 920                 925

Pro Val Val Ala Arg Arg Gly Asp Glu Val Leu Ile Gly Val Phe Gln
            930                 935                 940

Asp Val Asn His Leu Pro Pro Gly Phe Xaa Pro Thr Ala Pro Val Val
945                 950                 955                 960

Ile Arg Arg Cys Gly Lys Gly Phe Leu Gly Val Thr Lys Ala Ala Leu
                965                 970                 975

Thr Gly Arg Asp Pro Asp Leu His Pro Gly Asn Val Met Val Leu Gly
            980                 985                 990

Thr Ala Thr Ser Arg Ser Met Gly Thr Cys Leu Asn Gly Leu Leu Phe
            995                 1000                1005

Thr Thr Phe His Gly Ala Ser Ser Arg Thr Ile Ala Thr Pro Val Gly
            1010                1015                1020

Ala Leu Asn Pro Arg Trp Trp Ser Ala Ser Asp Asp Val Thr Val Tyr
1025                1030                1035                1040

Pro Leu Pro Asp Gly Ala Asn Ser Leu Val Pro Cys Ser Cys Gln Ala
                1045                1050                1055

Glu Ser Cys Trp Val Xaa Arg Ser Asp Gly Ala Leu Cys His Gly Leu
                1060                1065                1070

Ser Lys Gly Asp Lys Val Glu Leu Asp Val Ala Met Glu Val Ala Asp
            1075                1080                1085

Phe Arg Gly Ser Ser Gly Ser Pro Val Leu Cys Asp Glu Gly His Ala
            1090                1095                1100

Val Gly Met Leu Val Ser Val Leu His Ser Gly Gly Arg Val Thr Ala
1105                1110                1115                1120

Ala Arg Phe Thr Arg Pro Trp Thr Gln Val Pro Thr Asp Ala Lys Thr
                1125                1130                1135

Thr Thr Glu Pro Pro Val Pro Ala Lys Gly Val Phe Lys Glu Ala
            1140                1145                1150

Pro Leu Phe Met Pro Thr Gly Ala Gly Lys Ser Thr Arg Val Pro Leu
            1155                1160                1165

Glu Tyr Gly Asn Met Gly His Lys Val Leu Ile Leu Asn Pro Ser Val
            1170                1175                1180

Ala Thr Val Arg Ala Met Gly Pro Tyr Met Glu Arg Leu Ala Gly Lys
1185                1190                1195                1200

His Pro Ser Ile Phe Cys Gly His Asp Thr Thr Ala Phe Thr Arg Ile
                1205                1210                1215

Thr Asp Ser Pro Leu Thr Tyr Ser Thr Tyr Gly Arg Phe Leu Ala Asn
            1220                1225                1230

Pro Arg Gln Met Leu Arg Gly Val Ser Val Val Ile Cys Asp Glu Cys
```

-continued

```
                1235                1240                     1245

His Ser His Asp Ser Thr Val Leu Leu Gly Ile Gly Arg Val Arg Asp
    1250                1255                1260

Val Ala Arg Gly Cys Gly Val Gln Leu Val Leu Tyr Ala Thr Ala Thr
1265                1270                1275                1280

Pro Pro Gly Ser Pro Met Thr Gln His Pro Ser Ile Ile Glu Thr Lys
                1285                1290                1295

Leu Asp Val Gly Glu Ile Pro Phe Tyr Gly His Gly Ile Pro Leu Glu
    1300                1305                1310

Arg Met Arg Thr Gly Arg His Leu Val Phe Cys His Ser Lys Ala Glu
        1315                1320                1325

Cys Glu Arg Leu Ala Gly Gln Phe Ser Ala Arg Gly Val Asn Ala Ile
    1330                1335                1340

Ala Tyr Tyr Arg Gly Lys Asp Ser Ser Ile Ile Lys Asp Gly Asp Leu
1345                1350                1355                1360

Val Val Cys Ala Thr Asp Ala Leu Ser Thr Gly Tyr Thr Gly Asn Phe
                1365                1370                1375

Asp Ser Val Thr Asp Cys Gly Leu Val Val Glu Glu Val Val Glu Val
            1380                1385                1390

Thr Leu Asp Pro Thr Ile Thr Ile Ser Leu Arg Thr Val Pro Ala Ser
        1395                1400                1405

Ala Glu Leu Ser Met Gln Arg Arg Gly Arg Thr Gly Arg Gly Arg Ser
    1410                1415                1420

Gly Arg Tyr Tyr Tyr Ala Gly Val Gly Lys Ala Pro Ala Gly Val Val
1425                1430                1435                1440

Arg Ser Gly Pro Val Trp Ser Ala Val Glu Ala Gly Val Thr Trp Tyr
                1445                1450                1455

Gly Met Glu Pro Asp Leu Thr Ala Asn Leu Leu Arg Leu Tyr Asp Asp
    1460                1465                1470

Cys Pro Tyr Thr Ala Ala Val Ala Ala Asp Ile Gly Glu Ala Ala Val
        1475                1480                1485

Phe Phe Ala Gly Leu Ala Pro Leu Arg Met His Pro Asp Val Ser Trp
    1490                1495                1500

Ala Lys Val Arg Gly Val Asn Trp Pro Leu Leu Val Gly Val Gln Arg
1505                1510                1515                1520

Thr Met Cys Arg Glu Thr Leu Ser Pro Gly Pro Ser Asp Asp Pro Gln
                1525                1530                1535

Trp Ala Gly Leu Lys Gly Pro Asn Pro Val Pro Leu Leu Leu Arg Trp
            1540                1545                1550

Gly Asn Asp Leu Pro Ser Lys Val Ala Gly His His Ile Val Asp Asp
        1555                1560                1565

Leu Val Arg Arg Leu Gly Val Ala Glu Gly Tyr Val Arg Cys Asp Ala
    1570                1575                1580

Xaa Pro Ile Leu Met Val Gly Leu Ala Ile Ala Gly Gly Met Ile Tyr
1585                1590                1595                1600

Ala Ser Tyr Thr Gly Ser Leu Val Val Thr Asp Trp Asp Val Lys
                1605                1610                1615

Gly Gly Gly Asn Pro Leu Tyr Arg Ser Gly Asp Gln Ala Thr Pro Gln
            1620                1625                1630

Pro Val Val Gln Val Pro Pro Val Asp His Arg Pro Gly Gly Glu Ser
        1635                1640                1645

Ala Pro Arg Asp Ala Lys Thr Val Thr Asp Ala Val Ala Ala Ile Gln
    1650                1655                1660
```

-continued

```
Val Asn Cys Asp Trp Ser Val Met Thr Leu Ser Ile Gly Glu Val Leu
1665                1670                1675                1680

Thr Leu Ala Gln Ala Lys Thr Ala Glu Ala Tyr Ala Ala Thr Ser Arg
            1685                1690                1695

Trp Leu Ala Gly Cys Tyr Thr Gly Thr Arg Ala Val Pro Thr Val Ser
            1700                1705                1710

Ile Val Asp Lys Leu Phe Ala Gly Gly Trp Ala Ala Val Val Gly His
            1715                1720                1725

Cys His Ser Val Ile Ala Ala Val Ala Ala Tyr Gly Ala Ser Arg
            1730                1735            1740

Ser Pro Pro Leu Ala Ala Ala Ser Tyr Leu Met Gly Leu Gly Val
1745                1750                1755                1760

Gly Gly Asn Ala Gln Ala Arg Leu Ala Ser Ala Leu Leu Gly Ala
            1765                1770                1775

Ala Gly Thr Ala Leu Gly Thr Pro Val Val Gly Leu Thr Met Ala Gly
            1780                1785                1790

Ala Phe Met Gly Gly Ala Ser Val Ser Pro Ser Leu Val Thr Val Leu
            1795                1800                1805

Leu Gly Ala Val Gly Gly Trp Glu Gly Val Val Asn Ala Ala Ser Leu
    1810                1815                1820

Val Phe Asp Phe Met Ala Gly Lys Leu Ser Thr Glu Asp Leu Trp Tyr
1825                1830                1835                1840

Ala Ile Pro Val Leu Thr Ser Pro Xaa Ala Gly Leu Ala Gly Ile Ala
            1845                1850                1855

Leu Gly Leu Val Leu Tyr Ser Ala Asn Asn Ser Gly Thr Thr Thr Trp
            1860                1865                1870

Leu Asn Arg Leu Leu Thr Thr Leu Pro Arg Ser Ser Cys Ile Pro Asp
    1875                1880                1885

Ser Tyr Phe Gln Gln Ala Asp Tyr Cys Asp Lys Val Ser Ala Ile Val
    1890                1895                1900

Arg Arg Leu Ser Leu Thr Arg Thr Val Val Ala Leu Val Asn Arg Glu
1905                1910                1915                1920

Pro Lys Val Asp Glu Val Gln Val Gly Tyr Val Trp Asp Leu Trp Glu
            1925                1930                1935

Trp Val Met Arg Gln Val Arg Met Val Met Ser Arg Leu Arg Ala Leu
            1940                1945                1950

Cys Pro Val Val Ser Leu Pro Leu Trp His Cys Gly Glu Gly Trp Ser
            1955                1960                1965

Gly Glu Trp Leu Leu Asp Gly His Val Glu Ser Arg Cys Leu Cys Gly
    1970                1975                1980

Cys Val Ile Thr Gly Asp Val Leu Asn Gly Gln Leu Lys Asp Pro Val
1985                1990                1995                2000

Tyr Ser Thr Lys Leu Cys Arg His Tyr Trp Met Gly Thr Val Pro Val
            2005                2010                2015

Asn Met Leu Gly Tyr Gly Glu Thr Ser Pro Leu Leu Ala Ser Asp Thr
            2020                2025                2030

Pro Lys Val Val Pro Phe Gly Thr Ser Gly Trp Ala Glu Val Val Val
            2035                2040                2045

Thr Pro Thr His Val Val Ile Arg Arg Thr Ser Cys Tyr Lys Leu Leu
        2050                2055                2060

Arg Gln Gln Ile Leu Ser Ala Val Ala Glu Pro Tyr Tyr Val Asp
2065                2070                2075                2080
```

-continued

```
Gly Ile Pro Val Ser Trp Glu Ala Asp Ala Arg Ala Pro Ala Met Val
            2085                2090                2095

Tyr Gly Pro Gly Gln Ser Val Thr Ile Asp Gly Glu Arg Tyr Thr Leu
        2100                2105                2110

Pro His Gln Leu Arg Met Arg Asn Val Ala Pro Ser Glu Val Ser Ser
        2115                2120                2125

Glu Val Ser Ile Glu Ile Gly Thr Glu Thr Glu Asp Ser Glu Leu Thr
    2130                2135                2140

Glu Ala Asp Leu Pro Pro Ala Ala Ala Leu Gln Ala Ile Glu Asn
2145                2150                2155                2160

Ala Ala Arg Ile Leu Glu Pro His Ile Asp Val Xaa Met Glu Asp Cys
            2165                2170                2175

Ser Thr Pro Ser Leu Cys Gly Ser Ser Arg Glu Met Pro Val Trp Gly
        2180                2185                2190

Glu Asp Ile Pro Arg Thr Pro Ser Pro Ala Leu Ile Ser Val Thr Glu
        2195                2200                2205

Ser Ser Ser Asp Glu Lys Thr Leu Ser Val Thr Ser Ser Gln Glu Asp
    2210                2215                2220

Thr Pro Ser Ser Asp Ser Phe Glu Val Ile Gln Glu Ser Asp Thr Ala
2225                2230                2235                2240

Glu Ser Glu Glu Ser Val Phe Asn Val Ala Leu Ser Val Leu Lys Ala
        2245                2250                2255

Leu Phe Pro Gln Ser Asp Ala Thr Arg Lys Leu Thr Val Lys Met Ser
        2260                2265                2270

Cys Cys Val Glu Lys Ser Val Thr Arg Phe Phe Ser Leu Gly Leu Thr
        2275                2280                2285

Val Ala Asp Val Ala Ser Leu Cys Glu Met Glu Ile Gln Asn His Thr
        2290                2295                2300

Ala Tyr Cys Asp Lys Val Arg Thr Pro Leu Glu Leu Gln Val Gly Cys
2305                2310                2315                2320

Leu Val Gly Asn Glu Leu Thr Phe Glu Cys Asp Lys Cys Glu Ala Arg
        2325                2330                2335

Gln Glu Thr Leu Ala Ser Phe Ser Tyr Ile Trp Ser Gly Val Pro Leu
        2340                2345                2350

Thr Arg Ala Thr Pro Ala Lys Pro Pro Val Val Arg Pro Val Gly Ser
        2355                2360                2365

Leu Leu Val Ala Asp Thr Thr Lys Val Tyr Val Thr Asn Pro Asp Asn
    2370                2375                2380

Val Gly Arg Arg Val Asp Lys Val Thr Phe Trp Arg Ala Pro Arg Val
2385                2390                2395                2400

His Asp Lys Phe Leu Val Asp Ser Ile Glu Arg Ala Arg Arg Ala Ala
            2405                2410                2415

Gln Gly Cys Leu Ser Met Gly Tyr Thr Tyr Glu Glu Ala Ile Arg Thr
        2420                2425                2430

Val Arg Pro His Ala Ala Met Gly Trp Gly Ser Lys Val Ser Val Lys
        2435                2440                2445

Asp Leu Ala Thr Pro Ala Gly Lys Met Ala Val His Asp Arg Leu Gln
    2450                2455                2460

Glu Ile Leu Glu Gly Thr Pro Val Pro Phe Thr Leu Thr Val Lys Lys
2465                2470                2475                2480

Glu Val Phe Phe Lys Asp Arg Lys Glu Glu Lys Ala Pro Arg Leu Ile
            2485                2490                2495

Val Phe Pro Pro Leu Asp Phe Arg Ile Ala Glu Lys Leu Ile Leu Gly
```

-continued

```
                  2500                2505                2510
Asp Pro Gly Arg Val Ala Lys Ala Gly Val Gly Gly Ala Tyr Ala Phe
            2515                2520                2525
Gln Tyr Thr Pro Asn Gln Arg Val Lys Glu Met Leu Lys Leu Trp Glu
        2530                2535                2540
Ser Lys Lys Thr Pro Cys Ala Ile Cys Val Asp Ala Thr Cys Phe Asp
2545                2550                2555                2560
Ser Ser Ile Thr Xaa Glu Asp Val Ala Leu Glu Thr Glu Leu Tyr Ala
                2565                2570                2575
Leu Ala Ser Asp His Pro Glu Trp Val Arg Ala Leu Gly Lys Tyr Xaa
            2580                2585                2590
Ala Ser Gly Thr Met Val Thr Pro Glu Gly Val Pro Val Gly Glu Arg
        2595                2600                2605
Tyr Cys Arg Ser Ser Gly Val Leu Thr Thr Ser Ala Ser Asn Cys Leu
    2610                2615                2620
Thr Cys Tyr Ile Lys Val Arg Ala Ala Cys Glu Arg Ile Gly Leu Lys
2625                2630                2635                2640
Asn Val Ser Leu Leu Ile Ala Gly Asp Asp Cys Leu Ile Val Cys Glu
                2645                2650                2655
Arg Pro Val Cys Asp Pro Cys Glu Ala Leu Gly Arg Thr Leu Ala Ser
            2660                2665                2670
Tyr Gly Tyr Ala Cys Glu Pro Ser Tyr His Ala Ser Leu Asp Thr Ala
        2675                2680                2685
Pro Phe Cys Ser Thr Trp Leu Ala Glu Cys Asn Ala Asp Gly Xaa Arg
    2690                2695                2700
His Phe Phe Leu Thr Thr Asp Phe Arg Arg Pro Leu Ala Arg Met Ser
2705                2710                2715                2720
Ser Glu Tyr Ser Asp Pro Met Ala Ser Ala Ile Gly Tyr Ile Leu Leu
                2725                2730                2735
Tyr Pro Trp Xaa Pro Ile Thr Arg Trp Val Ile Ile Pro His Val Leu
            2740                2745                2750
Thr Cys Ala Ser Ser Arg Gly Gly Gly Thr Xaa Ser Asp Pro Val Trp
        2755                2760                2765
Cys Gln Val His Gly Asn Tyr Tyr Lys Phe Pro Leu Asp Lys Leu Pro
    2770                2775                2780
Asn Ile Ile Val Ala Leu His Gly Pro Ala Ala Leu Arg Val Thr Ala
2785                2790                2795                2800
Asp Thr Thr Lys Thr Lys Met Glu Ala Gly Lys Val Leu Ser Asp Leu
                2805                2810                2815
Lys Leu Pro Gly Leu Ala Val His Arg Lys Lys Ala Gly Ala Leu Arg
            2820                2825                2830
Thr Arg Met Leu Arg Ser Arg Gly Trp Ala Glu Leu Ala Arg Gly Leu
        2835                2840                2845
Leu Trp His Pro Gly Leu Arg Leu Pro Pro Glu Ile Ala Gly Ile
    2850                2855                2860
Pro Gly Gly Phe Pro Leu Ser Pro Pro Tyr Met Gly Val Val His Gln
2865                2870                2875                2880
Leu Asp Phe Thr Xaa Gln Arg Ser Arg Trp Arg Trp Leu Gly Phe Leu
                2885                2890                2895
Ala Leu Leu Ile Val Ala Leu Phe Gly
            2900                2905

(2) INFORMATION FOR SEQ ID NO:34:
```

(i) SEQUENCE CHARACTERISTICS:
        (A) LENGTH:9126 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
CCCCCCCCCC GGCACTGGGT GCAAGCCCCA GAAACCGACG CCTACTGAAG TAGACGTAAT      60
GGCCCCGCGC CGAACCGGCG ACCGGCCAAA AGGTGGTGGA TGGGTGATGA CAGGGTTGGT     120
AGGTCGTAAA TCCCGGTCAT CCTGGTAGCC ACTATAGGTG GGTCTTAAGG GGAGGCTACG     180
GTCCCTCTTG CGCATATGGA GGAAAAGCGC ACGGTCCACA GGTGTTGGTC CTACCGGTGT     240
AATAAGGACC CGGCGCTAGG CACGCCGTTA AACCGAGCCC GTTACTCCCC TGGGCAAACG     300
ACGCCCACGT ACGGTCCACG TCGCCCTTCA ATGTCTCTCT TGACCAATAG GCGTAGCCGG     360
CGAGTTGACA AGGACCAGTG GGGGCCGGGC GGGAGGGGGA AGGACCCCCA CCGCTGCCCT     420
TCCCGGGGAG GCGGGAAATG CATGGGGCCA CCCAGCTCCG CGGCGGCCTA CAGCCGGGGT     480
AGCCCAAGAA CCTTCGGGTG AGGGCGGGTG GCATTTCTTT TCCTATACCG ATCATGGCAG     540
TCCTTCTGCT CCTACTCGTG GTGGAGGCCG GGGCTATTTT AGCCCCGGCC ACCCATGCTT     600
GTAGCGCGAA AGGGCAATAT TTBCTCACAA ACTGTTGCGC CCTGGAGGAC ATAGGCTTCT     660
GCCTGGAGGG CGGATGCCTG GTGGCTCTGG GGTGCACCAT TTGCACCGAC CGCTGCTGGC     720
CACTGTATCA GGCGGGTTTG GCCGTGCGGC CCGGCAAGTC CGCCGCCCAG TTGGTGGGGG     780
AACTCGGTAG TCTCTACGGG CCCTTGTCGG TCTCGGCTTA TGTGGCCGGG ATCCTGGGGC     840
TTGGGGAGGT CTACTCGGGG GTCCTCACCG TCGGGTGGC GTTGACGCGC AGGGTCTACC     900
CGGTCCCGAA CCTGACGTGT GCAGTAGAGT GTGAGTTGAA GTGGGAAAGT GAGTTTTGGA     960
GATGGACTGA ACAGCTGGCC TCAAACTACT GGATTCTGGA ATACCTCTGG AAGGTGCCTT    1020
TCGACTTTTG GCGGGGAGTG ATGAGCCTTT CTCCTCTCTT GGTGTGCGTG GCGGCCCTCC    1080
TCCTGCTGGA GCAGCGTATT GTCATGGTCT TCCTCCTGGT CACTATGGCG GGCATGTCAC    1140
AAGGCGCGCC CGCCTCAGTG TTGGGGTCAC GGCCTTTCGA GGCCGGGCTG ACTTGGCAGT    1200
CTTGTTCTTG CAGGTCGAAC GGGTCCCGCG CGCCGACAGG GGAGAGGGTT TGGGAACGTG    1260
GGAACGTCAC ACTTTTGTGT GACTGCCCCA ACGGTCCTTG GGTGTGGGTC CCGGCCCTTT    1320
GCCAGGCAAT CGGATGGGGC GACCCTATCA CTCATTGGAG CCACGGACGA AATCAGTGGC    1380
CCCTTTCTTG TCCCCAATTT GTCTACGGCG CCGTTTCAGT GACCTGCGTG TGGGGTTCTG    1440
TGTCTTGGTT TGCTTCCACT GGGGGTCGCG ACTCCAAGGT TGATGTGTGG AGTTTGGTTC    1500
CAGTTGGCTC TGCCAGCTGT ACCATAGCCG CACTGGGATC TTCGGATCGC GACACAGTGG    1560
TTGAGCTCTC CGAATGGGGA ATCCCCTGCG CCACTTGTAT CCTGGACAGG CGGCCTGCCT    1620
CGTGTGGCAC CTGTGTGAGG GACTGCTGGC CCGAGACCGG GTCGGTACGT TTCCCATTCC    1680
ACAGGTGTGG CGCGGGACCG AGGCTGACCA GAGACCTTGA GGCTGTGCCC TTCGTCAATA    1740
GGACAACTCC CTTCACCATA AGGGGCCCC TGGGCAACCA GGGGCGAGGC GACCCGGTGC    1800
GGTCGCCCTT GGGTTTTGGG TCCTACACCA TGACCAAGAT CCGAGACTCC TTACACTTGG    1860
TGAAATGTCC CACCCCAGCC ATTGAGCCTC CCACCGGAAC GTTTGGGATC TTCCCAGGAG    1920
TCCCCCCCCT TAACAACTGC ATGCTTCTCG GCACTGAGGT GTCAGAGGTA TTGGGTGGGG    1980
CGGGCCTCAC TGGGGGGTTT TACGAACCTC TGGTGCGGCG GTGTTCAGAG CTGATGGGTC    2040
```

```
GGCGGAATCC GGTCTGCCCG GGGTTTGCAT GGCTCTCTTC GGGACGGCCT GATGGGTTCA    2100

TACATGTACA GGGCCACTTG CAGGAGGTGG ATGCGGGCAA CTTCATTCCG CCCCCACGCT    2160

GGTTGCTCTT GGACTTTGTA TTTGTCCTGT CATACCTGAT GAAGCTGGCA GAGGCACGGT    2220

TGGTCCCGCT GATCCTCCTC CTGCTATGGT GGTGGGTGAA CCAGTTGGCG GTCCTTGKAC    2280

TGSCGGCTGC KCRCGCCGCC GTGGCTGGAG AGGTGTTTGC GGGCCCTGCC TTGTCCTGGT    2340

GTCTGGGCCT ACCCTTCGTG AGTATGATCC TGGGGCTAGC AAACCTGGTG TTGTACTTCC    2400

GCTGGATGGG TCCTCAACGC CTGATGTTCC TCGTGTTGTG GAAGCTCGCT CGGGGGGCTT    2460

TCCCGCTGGC ATTACTGATG GGATTTCCG CCACTCGCGG CCGCACCTCT GTGCTTGGCG    2520

CCGAATTCTG CTTTGATGTC ACCTTTGAAG TGGACACGTC AGTCTTGGGT TGGGTGGTTG    2580

CTAGTGTGGT GGCTTGGGCC ATAGCGCTCC TGAGCTCTAT GAGCGCGGGG GGGTGGAAGC    2640

ACAAAGCCAT AATCTATAGG ACGTGGTGTA AAGGGTACCA GGCYCTTCGC CAGCGCGTGG    2700

TGCGTAGCCC CCTCGGGGAG GGGCGGCCCA CCAAGCCGCT GACGATAGCC TGGCGTCTGG    2760

CCTCTTACAT CTGGCCGGAC GCTGTGATGT TGGTGGTTGT GGCCATGGTC CTCCTCTTCG    2820

GCCTTTTCGA CGCGCTCGAT TGGGCCTTGG AGGAGCTCCT TGTGTCGCGG CCTTCGTTGC    2880

GTCGTTTGGC AAGGGTGGTG GAGTGTTGTG TGATGGCGGG CGAGAAGGCC ACTACCGTCC    2940

GGCTTGTGTC CAAGATGTGC GCGAGAGGGG CCTACCTGTT TGACCACATG GGGTCGTTCT    3000

CGCGCGCGGT CAAGGAGCGC TTGCTGGAGT GGGACGCGGC TTTGGAGMCC CTGTCATTCA    3060

CTAGGACGGA CTGCCGCATC ATACGAGACG CCGCCAGGAC TCTGAGCTGC GGCCAATGCG    3120

TCATGGGCTT GCCCGTGGTG GCTAGGCGCG GCGATGAGGT CCTGGTTGGG GTCTTTCAGG    3180

ATGTGAACCA CTTGCCTCCG GGGTTTGYTC CTACAGCGCC TGTTGTCATC CGTCGGTGCG    3240

GAAAGGGCTT CCTCGGGGTC ACTAAGGCTG CCTTGACTGG TCGGGATCCT GACTTACACC    3300

CAGGAAACGT CATGGTTTTG GGGACGGCTA CCTCGCGCAG CATGGGAACG TGCTTAAACG    3360

GGTTGCTGTT CACGACATTC CATGGGGCTT CTTCCCGAAC CATTGCGACA CCTGTGGGGG    3420

CCCTTAACCC AAGGTGGTGG TCGGCCAGTG ATGACGTCAC GGTCTATCCC CTCCCCGATG    3480

GAGCTAACTC GTTGGTTCCC TGCTCGTGTC AGGCTGAGTC CTGTTGGGTC ATYCGATCCG    3540

ATGGGGCTCT TTGCCATGGC TTGAGCAAGG GGACAAGGT AGAACTGGAC GTGGCCATGG    3600

AGGTTGCTGA CTTTCGTGGG TCGTCTGGGT CTCCTGTCCT ATGCGACGAG GGGCACGCTG    3660

TAGGAATGCT CGTGTCCGTC CTTCATTCGG GGGGAGGGT GACCGCGGCT CGATTCACTC    3720

GGCCGTGGAC CCAAGTCCCA ACAGACGCCA AGACTACCAC TGAGCCACCC CCGGTGCCAG    3780

CTAAAGGGGT TTTCAAAGAG GCTCCTCTTT TCATGCCAAC AGGGGCGGGG AAAAGCACAC    3840

GCGTCCCTTT GGAATATGGA AACATGGGGC ACAAGGTCCT GCTTCTCAAC CCGTCGGTTG    3900

CCACTGTGAG GGCCATGGGC CCTTACATGG AGAAGCTGGC GGGGAAACAT CCTAGCATTT    3960

TCTGTGGACA CGACACAACA GCTTTCACAC GGATCACGGA CTCTCCATTG ACGTACTCTA    4020

CCTATGGGAG GTTTCTGGCC AACCCGAGGC AGATGCTGAG GGGAGTTTCC GTGGTCATCT    4080

GTGATGAGTG CCACAGTCAT GACTCAACTG TGTTGCTGGG TATAGGCAGG GGCAGGGAGC    4140

TGGCGCGGGG GTGTGGAGTG CAATTAGTGC TCTACGCTAC TGCGACTCCC CCGGGCTCGC    4200

CTATGACTCA GCATCCATCC ATAATTGAGA CAAAGCTGGA CGTCGGTGAG ATCCCCTTTT    4260

ATGGGCATGG TATCCCCCTC GAGCGTATGA GGACTGGTCG CCACCTTGTA TTCTGCCATT    4320

CCAAGGCGGA GTGCGAGAGA TTGGCCGGCC AGTTCTCCGC GCGGGGGGTT AATGCCATCG    4380

CCTATTATAG GGGTAAGGAC AGTTCCATCA TCAAAGACGG AGACCTGGTG GTTTGTGCGA    4440
```

```
CAGACGCGCT CTCTACCGGG TACACAGGAA ACTTCGATTC TGTCACCGAC TGTGGGTTAG    4500

TGGTGGAGGA GGTCGTTGAG GTGACCCTTG ATCCCACCAT TACCATTTCC TTGCGGACTG    4560

TCCCTGCTTC GGCTGAATTG TCGATGCAGC GGCGCGGACG CACGGGGAGA GGTCGGTCGG    4620

GCCGCTACTA CTACGCTGGG GTCGGTAAGG CTCCCGCGGG GGTGGTGCGG TCTGGTCCGG    4680

TCTGGTCGGC AGTGGAAGCT GGAGTGACCT GGTATGGAAT GGAACCTGAC TTGACAGCAA    4740

ACCTTCTGAG ACTTTACGAC GACTGCCCTT ACACCGCAGC CGTCGCAGCT GACATTGGTG    4800

AAGCCGCGGT GTTCTTTGCG GGCCTCGCGC CCCTCAGGAT GCATCCCGAT GTTAGCTGGG    4860

CAAAAGTTCG CGGCGTCAAT TGGCCCCTCC TGGTGGGTGT TCAGCGGACG ATGTGTCGGG    4920

AAACACTGTC TCCCGGCCCG TCGGACGACC CTCAGTGGGA GGTCTGAAA GGCCCGAATC    4980

CTGCCCCACT ACTGCTGAGG TGGGGCAATG ATTTGCCATC AAAAGTGGCC GGCCACCACA    5040

TAGTTGACGA TCTGGTCCGT CGGCTCGGTG TGGCGGAGGG ATACGTGCGC TGTGATGCTG    5100

GRCCCATCCT CATGGTGGGC TTGGCCATAG CGGGCGGCAT GATCTACGCC TCTTACACTG    5160

GGTCGCTAGT GGTGGTAACA GACTGGAATG TGAAGGGAGG TGGCAATCCC CTTTATAGGA    5220

GTGGTGACCA GGCCACCCCT CAACCCGTGG TGCAGGTCCC CCCGGTAGAC CATCGGCCGG    5280

GGGGGGAGTC TGCGCCAGCG GATGCCAAGA CAGTGACAGA TGCGGTGGCA GCCATCCAGG    5340

TGAACTGCGA TTGGTCTGTG ATGACCCTGT CGATCGGGGA AGTCCTCACC TTGGCTCAGG    5400

CTAAGACAGC CGAGGCCTAC GCAGCTACTT CCAGGTGGCT CGCTGGCTGC TACACGGGGA    5460

CGCGGGCCGT CCCCACTGTA TCAATTGTTG ACAAGCTCTT CGCCGGGGGT TGGGCCGCCG    5520

TGGTGGGTCA CTGTCACAGC GTCATTGCTG CGGTGGTGGC TGCCTATGGG GTTTCTCGAA    5580

GTCCTCCACT GGCCGCGGCG GCATCCTACC TCATGGGGTT GGGCGTCGGA GGCAACGCAC    5640

AGGCGCGCTT GGCTTCAGCT CTTCTACTGG GGGCTGCTGG TACGGCTCTG GGACCCCTG    5700

TCGTGGGACT CACCATGGCG GGGGCCTTCA TGGGCGGTGC CAGCGTGTCC CCCTCCCTCG    5760

TCACTGTCCT ACTTGGGGCT GTGGGAGGTT GGGAGGGCGT TGTCAACGCT GCCAGTCTCG    5820

TCTTCGACTT CATGGCTGGG AAACTTTCAA CAGAAGACCT TTGGTATGCC ATCCCGGTAC    5880

TCACTAGTCC TGGRGCGGGC CTCGCGGGGA TTGCCCTTGG TCTGGTTTTG TACTCAGCAA    5940

ACAACTCTGG CACTACCACA TGGCTGAACC GTCTGCTGAC GACGTTGCCA CGGTCATCTT    6000

GCATACCCGA CAGCTACTTC CAACAGGCTG ACTACTGCGA CAAGGTCTCG GCAATGCTGC    6060

GCCGCCTGAG CCTTACTCGC ACCGTGGTGG CCCTGGTCAA CAGGGAGCCT AAGGTGGATG    6120

AGGTCCAGGT GGGGTACGTC TGGGATCTGT GGGAGTGGGT AATGCGCCAG GTGCGCATGG    6180

TGATGTCTAG ACTCCGGGCC CTCTGCCCTG TGGTGTCACT CCCCTTGTGG CACCGCGGGG    6240

AGGGGTGGTC CGGTGAATGG CTTCTCGATG GGCACGTGGA GAGTCGTTGT CTGTGCGGGT    6300

GTGTAATCAC CGGCGACGTC CTCAATGGGC AACTCAAAGA TCCAGTTTAC TCTACCAAGC    6360

TGTGCAGGCA CTACTGGATG GGAACTGTGC CGGTCAACAT GCTGGGCTAC GGGGAAACCT    6420

CACCTCTTCT CGCCTCTGAC ACCCCGAAGG TGGTACCCTT CGGGACGTCG GGGTGGGCTG    6480

AGGTGGTGGT GACCCCTACC CACGTGGTGA TCAGGCGCAC GTCCTGTTAC AAACTGCTTC    6540

GCCAGCAAAT TCTTTCAGCA GCTGTAGCTG AGCCCTACTA CGTTGATGGC ATTCGGTCT    6600

CTTGGGAGGC TGACGCGAGA GCGCCGGCCA TGGTCTACGG TCCGGGCCAA AGTGTTACCA    6660

TTGATGGGGA GCGCTACACC CTTCCGCACC AGTTGCGGAT GCGGAATGTG GCGCCCTCTG    6720

AGGTTTCATC CGAGGTCAGC ATCGAGATCG GGACGGAGAC TGAAGACTCA GAACTGACTG    6780
```

```
AGGCCGATTT GCCACCAGCG GCTGCTGCCC TCCAAGCGAT AGAGAATGCT GCGAGAATTC    6840

TCGAACCGCA CATCGATGTC AYCATGGAGG ATTGCAGTAC ACCCTCTCTC TGTGGTAGTA    6900

GCCGAGAGAT GCCTGTGTGG GGAGAAGACA TACCCCGCAC TCCATCGCCT GCACTTATCT    6960

CGGTTACGGA GAGCAGCTCA GATGAGAAGA CCCTGTCGGT GACCTCCTCG CAGGAGGACA    7020

CCCCGTCCTC AGACTCATTT GAAGTCATCC AAGAGTCTGA TACTGCTGAA TCAGAGGAAA    7080

GCGTCTTCAA CGTGGCTCTT TCCGTACTAA AAGCATTATT TCCACAGAGC GTTGCCACAC    7140

GAAAGCTAAC GGTTAAGATG TCTTGCTGTG TTGAGAAGAG CGTAACACGC TTCTTTTCTT    7200

TAGGGTTGAC CGTGGCTGAC GTGGCTAGCC TGTGTGAGAT GGAGATCCAG AACCATACAG    7260

CCTATTGTGA CAAGGTGCGC ACTCCGCTCG AATTGCAAGT TGGGTGCTTG GTGGGCAATG    7320

AACTTACCTT TGAATGTGAC AAGTGTGAGG CACGCCAAGA GACCCTTGCC TCCTTCTCCT    7380

ACATATGGTC CGGGGTCCCA CTTACTCGGG CCACTCCGGC CAAACCACCA GTGGTGAGGC    7440

CGGTGGGGTC CTTGTTGGTG GCAGACACCA CCAAGGTCTA CGTGACCAAT CCGGACAATG    7500

TTGGGAGGAG GGTTGACAAG GTGACTTTCT GGCGCGCTCC TCGGGTACAC GACAAGTTCC    7560

TCGTGGACTC GATCGAGCGC GCTCGGAGAG CTGCTCAAGG CTGCCTAAGC ATGGGTTACA    7620

CTTATGAGGA GGCAATAAGG ACTGTTAGGC CGCATGCTGC CATGGGCTGG GGATCTAAGG    7680

TGTCGGTCAG GGACTTGGCC ACCCCTGCGG GGAAGATGGC TGTTCATGAC CGGCTTCAGG    7740

AGATACTTGA AGGGACTCCA GTCCCTTTTA CCCTGACTGT CAAAAAGGAG GTGTTCTTCA    7800

AAGATCGTAA GGAGGAGAAG GCCCCCCGCC TCATTGTGTT CCCCCCCCTG GACTTCCGGA    7860

TAGCTGAAAA GCTCATTCTG GGAGACCCGG GGCGGGTTGC AAAGGCGGTG TGGGGGGGGG    7920

CTTACGCCTT CCAGTACACC CCCAACCAGC GGGTTAAGGA GATGCTAAAG CTGTGGGAAT    7980

CAAAGAAGAC CCCGTGCGCC ATCTGTGTGG ATGCCACTTG CTTCGACAGT AGCATTACTG    8040

ARGAGGACGT GGCACTAGAG ACAGAGCTTT ACGCCCTGGC CTCGGACCAT CCAGAATGGG    8100

TGCGCGCCCT GGGGAAATAC TRTGCCTCTG GCACAATGGT GACCCCGGAA GGGGTGCCAG    8160

TGGGCGAGAG GTATTGTAGG TCCTCGGGTG TGTTAACCAC AAGTGCTAGC AACTGTTTGA    8220

CCTGCTACAT CAAAGTGAGA GCCGCCTGTG AGAGGATCGG ACTGAAAAAT GTCTCGCTTC    8280

TCATCGCGGG CGATGACTGC TTAATTGTGT GCGAGAGGCC TGTATGCGAC CCTTGCGAGG    8340

CCCTGGGCCG AGCCCTGGCT TCGTACGGGT ACGCGTGTGA GCCCTCGTAT CACGCTTCAC    8400

TGGACACAGC CCCCTTCTGC TCCACTTGGC TTGCTGAGTG CAATGCGGAT GGGRAAAGGC    8460

ATTTCTTCCT GACCACGGAC TTTCGGAGAC CACTCGCTCG CATGTCGAGC GAGTACAGTG    8520

ACCCTATGGC TTCGGCCATT GGTTACATTC TCCTCTATCC CTGGCRTCCC ATCACACGGT    8580

GGGTCATCAT CCCGCATGTG CTAACATGCG CTTCTTTCCG GGGTGGTGGC ACACSGTCTG    8640

ATCCGGTTTG GTGTCAGGTT CATGGTAACT ACTACAAGTT TCCCCTGGAC AAAACTGCCTA   8700

ACATCATCGT GGCCCTCCAC GGACCAGCAG CGTTGAGGGT TACCGCAGAC ACAACCAAAA    8760

CAAAGATGGA GGCTGGGAAG GTTCTGAGCG ACCTCAAGCT CCCTGGTCTA GCCGTCCACC    8820

GCAAGAAGGC CGGGGCATTG CGAACACGCA TGCTCCGGTC GCGCGGTTGG GCGGAGTTGG    8880

CTAGGGGCCT GTTGTGGCAT CCAGGACTCC GGCTTCCTCC CCCTGAGATT GCTGGTATCC    8940

CAGGGGGTTT CCCTCTGTCC CCCCCCTACA TGGGGGTGGT TCATCAATTG GATTTCACAG    9000

CSCAGCGGAG TCGCTGGCGG TGGTTGGGGT TCTTAGCCCT GCTCATCGTA GCGCTCTTTG    9060

GGTGAACTAA ATTCATCTGT TGCGGCCGGA GTCAGACCTG AGCCCCGTTC AAAAGGGGAT    9120

TGAGAC                                                              9126
```

(2) INFORMATION FOR SEQ ID NO:35:

(i) SEQUENCE CHARACTERISTICS:
        (A) LENGTH: 2860 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Pro Lys Asn Leu Arg Val Arg Ala Gly Gly Ile Ser Phe Pro Ile Pro
                 5                  10                  15
Ile Met Ala Val Leu Leu Leu Leu Val Val Glu Ala Gly Ala Ile
         20                  25                  30
Leu Ala Pro Ala Thr His Ala Cys Ser Ala Lys Gly Gln Tyr Xaa Leu
             35                  40                  45
Thr Asn Cys Cys Ala Leu Glu Asp Ile Gly Phe Cys Leu Glu Gly Gly
         50                  55                  60
Cys Leu Val Ala Leu Gly Cys Thr Ile Cys Thr Asp Arg Cys Trp Pro
 65                  70                  75                  80
Leu Tyr Gln Ala Gly Leu Ala Val Arg Pro Gly Lys Ser Ala Ala Gln
             85                  90                  95
Leu Val Gly Glu Leu Gly Ser Leu Tyr Gly Pro Leu Ser Val Ser Ala
            100                 105                 110
Tyr Val Ala Gly Ile Leu Gly Leu Gly Glu Val Tyr Ser Gly Val Leu
            115                 120                 125
Thr Val Gly Val Ala Leu Thr Arg Arg Val Tyr Pro Val Pro Asn Leu
            130                 135                 140
Thr Cys Ala Val Glu Cys Glu Leu Lys Trp Glu Ser Glu Phe Trp Arg
145                 150                 155                 160
Trp Thr Glu Gln Leu Ala Ser Asn Tyr Trp Ile Leu Glu Tyr Leu Trp
                165                 170                 175
Lys Val Pro Phe Asp Phe Trp Arg Gly Val Met Ser Leu Ser Pro Leu
            180                 185                 190
Leu Val Cys Val Ala Ala Leu Leu Leu Glu Gln Arg Ile Val Met
            195                 200                 205
Val Phe Leu Leu Val Thr Met Ala Gly Met Ser Gln Gly Ala Pro Ala
    210                 215                 220
Ser Val Leu Gly Ser Arg Pro Phe Glu Ala Gly Leu Thr Trp Gln Ser
225                 230                 235                 240
Cys Ser Cys Arg Ser Asn Gly Ser Arg Ala Pro Thr Gly Glu Arg Val
                245                 250                 255
Trp Glu Arg Gly Asn Val Thr Leu Leu Cys Asp Cys Pro Asn Gly Pro
            260                 265                 270
Trp Val Trp Val Pro Ala Leu Cys Gln Ala Ile Gly Trp Gly Asp Pro
        275                 280                 285
Ile Thr His Trp Ser His Gly Arg Asn Gln Trp Pro Leu Ser Cys Pro
    290                 295                 300
Gln Phe Val Tyr Gly Ala Val Ser Val Thr Cys Val Trp Gly Ser Val
305                 310                 315                 320
Ser Trp Phe Ala Ser Thr Gly Gly Arg Asp Ser Lys Val Asp Val Trp
                325                 330                 335
Ser Leu Val Pro Val Gly Ser Ala Ser Cys Thr Ile Ala Ala Leu Gly
            340                 345                 350
```

```
Ser Ser Asp Arg Asp Thr Val Val Glu Leu Ser Glu Trp Gly Ile Pro
        355                 360                 365
Cys Ala Thr Cys Ile Leu Asp Arg Arg Pro Ala Ser Cys Gly Thr Cys
        370                 375                 380
Val Arg Asp Cys Trp Pro Glu Thr Gly Ser Val Arg Phe Pro Phe His
385                 390                 395                 400
Arg Cys Gly Ala Gly Pro Arg Leu Thr Arg Asp Leu Glu Ala Val Pro
                405                 410                 415
Phe Val Asn Arg Thr Thr Pro Phe Thr Ile Arg Gly Pro Leu Gly Asn
            420                 425                 430
Gln Gly Arg Gly Asp Pro Val Arg Ser Pro Leu Gly Phe Gly Ser Tyr
            435                 440                 445
Thr Met Thr Lys Ile Arg Asp Ser Leu His Leu Val Lys Cys Pro Thr
            450                 455                 460
Pro Ala Ile Glu Pro Pro Thr Gly Thr Phe Gly Ile Phe Pro Gly Val
465                 470                 475                 480
Pro Pro Leu Asn Asn Cys Met Leu Leu Gly Thr Glu Val Ser Glu Val
                485                 490                 495
Leu Gly Gly Ala Gly Leu Thr Gly Gly Phe Tyr Glu Pro Leu Val Arg
            500                 505                 510
Arg Cys Ser Glu Leu Met Gly Arg Arg Asn Pro Val Cys Pro Gly Phe
            515                 520                 525
Ala Trp Leu Ser Ser Gly Arg Pro Asp Gly Phe Ile His Val Gln Gly
            530                 535                 540
His Leu Gln Glu Val Asp Ala Gly Asn Phe Ile Pro Pro Arg Trp
545                 550                 555                 560
Leu Leu Leu Asp Phe Val Phe Val Leu Ser Tyr Leu Met Lys Leu Ala
                565                 570                 575
Glu Ala Arg Leu Val Pro Leu Ile Leu Leu Leu Trp Trp Trp Val
            580                 585                 590
Asn Gln Leu Ala Val Leu Xaa Leu Xaa Ala Ala Xaa Ala Ala Val Ala
            595                 600                 605
Gly Glu Val Phe Ala Gly Pro Ala Leu Ser Trp Cys Leu Gly Leu Pro
            610                 615                 620
Phe Val Ser Met Ile Leu Gly Leu Ala Asn Leu Val Leu Tyr Phe Arg
625                 630                 635                 640
Trp Met Gly Pro Gln Arg Leu Met Phe Leu Val Leu Trp Lys Leu Ala
                645                 650                 655
Arg Gly Ala Phe Pro Leu Ala Leu Leu Met Gly Ile Ser Ala Thr Arg
                660                 665                 670
Gly Arg Thr Ser Val Leu Gly Ala Glu Phe Cys Phe Asp Val Thr Phe
            675                 680                 685
Glu Val Asp Thr Ser Val Leu Gly Trp Val Val Ala Ser Val Val Ala
            690                 695                 700
Trp Ala Ile Ala Leu Leu Ser Ser Met Ser Ala Gly Gly Trp Lys His
705                 710                 715                 720
Lys Ala Ile Ile Tyr Arg Thr Trp Cys Lys Gly Tyr Gln Ala Leu Arg
                725                 730                 735
Gln Arg Val Val Arg Ser Pro Leu Gly Glu Gly Arg Pro Thr Lys Pro
            740                 745                 750
Leu Thr Ile Ala Trp Arg Leu Ala Ser Tyr Ile Trp Pro Asp Ala Val
            755                 760                 765
```

-continued

```
Met Leu Val Val Val Ala Met Val Leu Leu Phe Gly Leu Phe Asp Ala
    770                 775                 780

Leu Asp Trp Ala Leu Glu Glu Leu Leu Val Ser Arg Pro Ser Leu Arg
785                 790                 795                 800

Arg Leu Ala Arg Val Val Glu Cys Cys Val Met Ala Gly Glu Lys Ala
                805                 810                 815

Thr Thr Val Arg Leu Val Ser Lys Met Cys Ala Arg Gly Ala Tyr Leu
            820                 825                 830

Phe Asp His Met Gly Ser Phe Ser Arg Ala Val Lys Glu Arg Leu Leu
        835                 840                 845

Glu Trp Asp Ala Ala Leu Glu Xaa Leu Ser Phe Thr Arg Thr Asp Cys
    850                 855                 860

Arg Ile Ile Arg Asp Ala Ala Arg Thr Leu Ser Cys Gly Gln Cys Val
865                 870                 875                 880

Met Gly Leu Pro Val Val Ala Arg Arg Gly Asp Glu Val Leu Val Gly
                885                 890                 895

Val Phe Gln Asp Val Asn His Leu Pro Pro Gly Phe Xaa Pro Thr Ala
            900                 905                 910

Pro Val Val Ile Arg Arg Cys Gly Lys Gly Phe Leu Gly Val Thr Lys
        915                 920                 925

Ala Ala Leu Thr Gly Arg Asp Pro Asp Leu His Pro Gly Asn Val Met
    930                 935                 940

Val Leu Gly Thr Ala Thr Ser Arg Ser Met Gly Thr Cys Leu Asn Gly
945                 950                 955                 960

Leu Leu Phe Thr Thr Phe His Gly Ala Ser Ser Arg Thr Ile Ala Thr
                965                 970                 975

Pro Val Gly Ala Leu Asn Pro Arg Trp Trp Ser Ala Ser Asp Asp Val
            980                 985                 990

Thr Val Tyr Pro Leu Pro Asp Gly Ala Asn Ser Leu Val Pro Cys Ser
        995                 1000                1005

Cys Gln Ala Glu Ser Cys Trp Val Ile Arg Ser Asp Gly Ala Leu Cys
    1010                1015                1020

His Gly Leu Ser Lys Gly Asp Lys Val Glu Leu Asp Val Ala Met Glu
1025                1030                1035                1040

Val Ala Asp Phe Arg Gly Ser Ser Gly Ser Pro Val Leu Cys Asp Glu
                1045                1050                1055

Gly His Ala Val Gly Met Leu Val Ser Val Leu His Ser Gly Gly Arg
            1060                1065                1070

Val Thr Ala Ala Arg Phe Thr Arg Pro Trp Thr Gln Val Pro Thr Asp
        1075                1080                1085

Ala Lys Thr Thr Thr Glu Pro Pro Val Pro Ala Lys Gly Val Phe
    1090                1095                1100

Lys Glu Ala Pro Leu Phe Met Pro Thr Gly Ala Gly Lys Ser Thr Arg
1105                1110                1115                1120

Val Pro Leu Glu Tyr Gly Asn Met Gly His Lys Val Leu Leu Leu Asn
                1125                1130                1135

Pro Ser Val Ala Thr Val Arg Ala Met Gly Pro Tyr Met Glu Lys Leu
            1140                1145                1150

Ala Gly Lys His Pro Ser Ile Phe Cys Gly His Asp Thr Thr Ala Phe
        1155                1160                1165

Thr Arg Ile Thr Asp Ser Pro Leu Thr Tyr Ser Thr Tyr Gly Arg Phe
    1170                1175                1180

Leu Ala Asn Pro Arg Gln Met Leu Arg Gly Val Ser Val Val Ile Cys
```

-continued

```
        1185                1190                1195                1200
Asp Glu Cys His Ser His Asp Ser Thr Val Leu Leu Gly Ile Gly Arg
                    1205                1210                1215
Gly Arg Glu Leu Ala Arg Gly Cys Gly Val Gln Leu Val Leu Tyr Ala
                    1220                1225                1230
Thr Ala Thr Pro Pro Gly Ser Pro Met Thr Gln His Pro Ser Ile Ile
                    1235                1240                1245
Glu Thr Lys Leu Asp Val Gly Glu Ile Pro Phe Tyr Gly His Gly Ile
                    1250                1255                1260
Pro Leu Glu Arg Met Arg Thr Gly Arg His Leu Val Phe Cys His Ser
1265                1270                1275                1280
Lys Ala Glu Cys Glu Arg Leu Ala Gly Gln Phe Ser Ala Arg Gly Val
                    1285                1290                1295
Asn Ala Ile Ala Tyr Tyr Arg Gly Lys Asp Ser Ser Ile Ile Lys Asp
                    1300                1305                1310
Gly Asp Leu Val Val Cys Ala Thr Asp Ala Leu Ser Thr Gly Tyr Thr
                    1315                1320                1325
Gly Asn Phe Asp Ser Val Thr Asp Cys Gly Leu Val Val Glu Glu Val
                    1330                1335                1340
Val Glu Val Thr Leu Asp Pro Thr Ile Thr Ile Ser Leu Arg Thr Val
1345                1350                1355                1360
Pro Ala Ser Ala Glu Leu Ser Met Gln Arg Arg Gly Arg Thr Gly Arg
                    1365                1370                1375
Gly Arg Ser Gly Arg Tyr Tyr Ala Gly Val Gly Lys Ala Pro Ala
                    1380                1385                1390
Gly Val Val Arg Ser Gly Pro Val Trp Ser Ala Val Glu Ala Gly Val
                    1395                1400                1405
Thr Trp Tyr Gly Met Glu Pro Asp Leu Thr Ala Asn Leu Leu Arg Leu
                    1410                1415                1420
Tyr Asp Asp Cys Pro Tyr Thr Ala Ala Val Ala Ala Asp Ile Gly Glu
1425                1430                1435                1440
Ala Ala Val Phe Phe Ala Gly Leu Ala Pro Leu Arg Met His Pro Asp
                    1445                1450                1455
Val Ser Trp Ala Lys Val Arg Gly Val Asn Trp Pro Leu Leu Val Gly
                    1460                1465                1470
Val Gln Arg Thr Met Cys Arg Glu Thr Leu Ser Pro Gly Pro Ser Asp
                    1475                1480                1485
Asp Pro Gln Trp Ala Gly Leu Lys Gly Pro Asn Pro Ala Pro Leu Leu
                    1490                1495                1500
Leu Arg Trp Gly Asn Asp Leu Pro Ser Lys Val Ala Gly His His Ile
1505                1510                1515                1520
Val Asp Asp Leu Val Arg Arg Leu Gly Val Ala Glu Gly Tyr Val Arg
                    1525                1530                1535
Cys Asp Ala Gly Pro Ile Leu Met Val Gly Leu Ala Ile Ala Gly Gly
                    1540                1545                1550
Met Ile Tyr Ala Ser Tyr Thr Gly Ser Leu Val Val Val Thr Asp Trp
                    1555                1560                1565
Asn Val Lys Gly Gly Gly Asn Pro Leu Tyr Arg Ser Gly Asp Gln Ala
                    1570                1575                1580
Thr Pro Gln Pro Val Val Gln Val Pro Pro Val Asp His Arg Pro Gly
1585                1590                1595                1600
Gly Glu Ser Ala Pro Ala Asp Ala Lys Thr Val Thr Asp Ala Val Ala
                    1605                1610                1615
```

```
Ala Ile Gln Val Asn Cys Asp Trp Ser Val Met Thr Leu Ser Ile Gly
        1620                1625                1630

Glu Val Leu Thr Leu Ala Gln Ala Lys Thr Ala Glu Ala Tyr Ala Ala
        1635                1640                1645

Thr Ser Arg Trp Leu Ala Gly Cys Tyr Thr Gly Thr Arg Ala Val Pro
        1650                1655                1660

Thr Val Ser Ile Val Asp Lys Leu Phe Ala Gly Gly Trp Ala Ala Val
1665                1670                1675                1680

Val Gly His Cys His Ser Val Ile Ala Ala Val Val Ala Ala Tyr Gly
        1685                1690                1695

Val Ser Arg Ser Pro Pro Leu Ala Ala Ala Ser Tyr Leu Met Gly
        1700                1705                1710

Leu Gly Val Gly Gly Asn Ala Gln Ala Arg Leu Ala Ser Ala Leu Leu
        1715                1720                1725

Leu Gly Ala Ala Gly Thr Ala Leu Gly Thr Pro Val Val Gly Leu Thr
        1730                1735                1740

Met Ala Gly Ala Phe Met Gly Gly Ala Ser Val Ser Pro Ser Leu Val
1745                1750                1755                1760

Thr Val Leu Leu Gly Ala Val Gly Gly Trp Glu Gly Val Val Asn Ala
        1765                1770                1775

Ala Ser Leu Val Phe Asp Phe Met Ala Gly Lys Leu Ser Thr Glu Asp
        1780                1785                1790

Leu Trp Tyr Ala Ile Pro Val Leu Thr Ser Pro Gly Ala Gly Leu Ala
        1795                1800                1805

Gly Ile Ala Leu Gly Leu Val Leu Tyr Ser Ala Asn Asn Ser Gly Thr
        1810                1815                1820

Thr Thr Trp Leu Asn Arg Leu Leu Thr Thr Leu Pro Arg Ser Ser Cys
1825                1830                1835                1840

Ile Pro Asp Ser Tyr Phe Gln Gln Ala Asp Tyr Cys Asp Lys Val Ser
        1845                1850                1855

Ala Met Leu Arg Arg Leu Ser Leu Thr Arg Thr Val Val Ala Leu Val
        1860                1865                1870

Asn Arg Glu Pro Lys Val Asp Glu Val Gln Val Gly Tyr Val Trp Asp
        1875                1880                1885

Leu Trp Glu Trp Val Met Arg Gln Val Arg Met Val Met Ser Arg Leu
        1890                1895                1900

Arg Ala Leu Cys Pro Val Val Ser Leu Pro Leu Trp His Arg Gly Glu
1905                1910                1915                1920

Gly Trp Ser Gly Glu Trp Leu Leu Asp Gly His Val Glu Ser Arg Cys
        1925                1930                1935

Leu Cys Gly Cys Val Ile Thr Gly Asp Val Leu Asn Gly Gln Leu Lys
        1940                1945                1950

Asp Pro Val Tyr Ser Thr Lys Leu Cys Arg His Tyr Trp Met Gly Thr
        1955                1960                1965

Val Pro Val Asn Met Leu Gly Tyr Gly Glu Thr Ser Pro Leu Leu Ala
        1970                1975                1980

Ser Asp Thr Pro Lys Val Val Pro Phe Gly Thr Ser Gly Trp Ala Glu
1985                1990                1995                2000

Val Val Val Thr Pro Thr His Val Val Ile Arg Arg Thr Ser Cys Tyr
        2005                2010                2015

Lys Leu Leu Arg Gln Gln Ile Leu Ser Ala Ala Val Ala Glu Pro Tyr
        2020                2025                2030
```

-continued

```
Tyr Val Asp Gly Ile Pro Val Ser Trp Glu Ala Asp Ala Arg Ala Pro
         2035                2040                2045

Ala Met Val Tyr Gly Pro Gly Gln Ser Val Thr Ile Asp Gly Glu Arg
     2050                2055                2060

Tyr Thr Leu Pro His Gln Leu Arg Met Arg Asn Val Ala Pro Ser Glu
2065                2070                2075                2080

Val Ser Ser Glu Val Ser Ile Glu Ile Gly Thr Glu Thr Glu Asp Ser
             2085                2090                2095

Glu Leu Thr Glu Ala Asp Leu Pro Pro Ala Ala Ala Leu Gln Ala
         2100                2105                2110

Ile Glu Asn Ala Ala Arg Ile Leu Glu Pro His Ile Asp Val Xaa Met
         2115                2120                2125

Glu Asp Cys Ser Thr Pro Ser Leu Cys Gly Ser Ser Arg Glu Met Pro
         2130                2135                2140

Val Trp Gly Glu Asp Ile Pro Arg Thr Pro Ser Pro Ala Leu Ile Ser
2145                2150                2155                2160

Val Thr Glu Ser Ser Ser Asp Glu Lys Thr Leu Ser Val Thr Ser Ser
             2165                2170                2175

Gln Glu Asp Thr Pro Ser Ser Asp Ser Phe Glu Val Ile Gln Glu Ser
         2180                2185                2190

Asp Thr Ala Glu Ser Glu Glu Ser Val Phe Asn Val Ala Leu Ser Val
     2195                2200                2205

Leu Lys Ala Leu Phe Pro Gln Ser Val Ala Thr Arg Lys Leu Thr Val
         2210                2215                2220

Lys Met Ser Cys Cys Val Glu Lys Ser Val Thr Arg Phe Phe Ser Leu
2225                2230                2235                2240

Gly Leu Thr Val Ala Asp Val Ala Ser Leu Cys Glu Met Glu Ile Gln
             2245                2250                2255

Asn His Thr Ala Tyr Cys Asp Lys Val Arg Thr Pro Leu Glu Leu Gln
             2260                2265                2270

Val Gly Cys Leu Val Gly Asn Glu Leu Thr Phe Glu Cys Asp Lys Cys
         2275                2280                2285

Glu Ala Arg Gln Glu Thr Leu Ala Ser Phe Ser Tyr Ile Trp Ser Gly
     2290                2295                2300

Val Pro Leu Thr Arg Ala Thr Pro Ala Lys Pro Val Val Arg Pro
2305                2310                2315                2320

Val Gly Ser Leu Leu Val Ala Asp Thr Thr Lys Val Tyr Val Thr Asn
             2325                2330                2335

Pro Asp Asn Val Gly Arg Arg Val Asp Lys Val Thr Phe Trp Arg Ala
         2340                2345                2350

Pro Arg Val His Asp Lys Phe Leu Val Asp Ser Ile Glu Arg Ala Arg
         2355                2360                2365

Arg Ala Ala Gln Gly Cys Leu Ser Met Gly Tyr Thr Tyr Glu Glu Ala
     2370                2375                2380

Ile Arg Thr Val Arg Pro His Ala Ala Met Gly Trp Gly Ser Lys Val
2385                2390                2395                2400

Ser Val Arg Asp Leu Ala Thr Pro Ala Gly Lys Met Ala Val His Asp
             2405                2410                2415

Arg Leu Gln Glu Ile Leu Glu Gly Thr Pro Val Pro Phe Thr Leu Thr
             2420                2425                2430

Val Lys Lys Glu Val Phe Phe Lys Asp Arg Lys Glu Lys Ala Pro
         2435                2440                2445

Arg Leu Ile Val Phe Pro Pro Leu Asp Phe Arg Ile Ala Glu Lys Leu
```

-continued

```
        2450                2455                  2460
Ile Leu Gly Asp Pro Gly Arg Val Ala Lys Ala Val Trp Gly Gly Ala
2465                2470                  2475                2480

Tyr Ala Phe Gln Tyr Thr Pro Asn Gln Arg Val Lys Glu Met Leu Lys
            2485                  2490                2495

Leu Trp Glu Ser Lys Lys Thr Pro Cys Ala Ile Cys Val Asp Ala Thr
            2500                  2505                2510

Cys Phe Asp Ser Ser Ile Thr Glu Glu Asp Val Ala Leu Glu Thr Glu
            2515                  2520                2525

Leu Tyr Ala Leu Ala Ser Asp His Pro Glu Trp Val Arg Ala Leu Gly
            2530                  2535                2540

Lys Tyr Xaa Ala Ser Gly Thr Met Val Thr Pro Glu Gly Val Pro Val
2545                2550                  2555                2560

Gly Glu Arg Tyr Cys Arg Ser Ser Gly Val Leu Thr Thr Ser Ala Ser
            2565                  2570                2575

Asn Cys Leu Thr Cys Tyr Ile Lys Val Arg Ala Ala Cys Glu Arg Ile
            2580                  2585                2590

Gly Leu Lys Asn Val Ser Leu Leu Ile Ala Gly Asp Asp Cys Leu Ile
2595                2600                  2605

Val Cys Glu Arg Pro Val Cys Asp Pro Cys Glu Ala Leu Gly Arg Ala
2610                2615                  2620

Leu Ala Ser Tyr Gly Tyr Ala Cys Glu Pro Ser Tyr His Ala Ser Leu
2625                2630                  2635                2640

Asp Thr Ala Pro Phe Cys Ser Thr Trp Leu Ala Glu Cys Asn Ala Asp
            2645                  2650                2655

Gly Xaa Arg His Phe Phe Leu Thr Thr Asp Phe Arg Arg Pro Leu Ala
            2660                  2665                2670

Arg Met Ser Ser Glu Tyr Ser Asp Pro Met Ala Ser Ala Ile Gly Tyr
            2675                  2680                2685

Ile Leu Leu Tyr Pro Trp Xaa Pro Ile Thr Arg Trp Val Ile Ile Pro
            2690                  2695                2700

His Val Leu Thr Cys Ala Ser Phe Arg Gly Gly Gly Thr Xaa Ser Asp
2705                2710                  2715                2720

Pro Val Trp Cys Gln Val His Gly Asn Tyr Tyr Lys Phe Pro Leu Asp
            2725                  2730                2735

Lys Leu Pro Asn Ile Ile Val Ala Leu His Gly Pro Ala Ala Leu Arg
            2740                  2745                2750

Val Thr Ala Asp Thr Thr Lys Thr Lys Met Glu Ala Gly Lys Val Leu
            2755                  2760                2765

Ser Asp Leu Lys Leu Pro Gly Leu Ala Val His Arg Lys Lys Ala Gly
            2770                  2775                2780

Ala Leu Arg Thr Arg Met Leu Arg Ser Arg Gly Trp Ala Glu Leu Ala
2785                2790                  2795                2800

Arg Gly Leu Leu Trp His Pro Gly Leu Arg Leu Pro Pro Glu Ile
            2805                  2810                2815

Ala Gly Ile Pro Gly Gly Phe Pro Leu Ser Pro Pro Tyr Met Gly Val
            2820                  2825                2830

Val His Gln Leu Asp Phe Thr Ala Gln Arg Ser Arg Trp Arg Trp Leu
            2835                  2840                2845

Gly Phe Leu Ala Leu Leu Ile Val Ala Leu Phe Gly
            2850                  2855                2860

(2) INFORMATION FOR SEQ ID NO:36:
```

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GATCGTCTAG AAGCAATGAA CTTGGCGCGC CCGCCTCAGT GTTG                              44

(2) INFORMATION FOR SEQ ID NO:37:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

ATATATCTAG ACTATCACGG AATGAAGTTG CCCGCATCCA C                                 41

(2) INFORMATION FOR SEQ ID NO:38:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

ATATATCTAG ACTATCACTT GTCGTCGTCG TCCTTGTAGT CCCGTCCCGA AGAGAGCCA             59

(2) INFORMATION FOR SEQ ID NO:39:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

ATATATCTAG ACTATCACTT GTCGTCGTCG TCCTTGTAGT CAGGTTCGTA AAACCCCCCA            60

(2) INFORMATION FOR SEQ ID NO:40:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

AATATATCTA GACTATCAGG GCGACCGCAC CGGGTTGCCT                                   40

(2) INFORMATION FOR SEQ ID NO:41:

(i) SEQUENCE CHARACTERISTICS:
        (A) LENGTH: 64 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:41:

CTAGCCACCA TGAAGGCTCT CATTGTTCTG GGGCTTGTCC TCCTTTCTGT TACGGTCCAG     60

GGCT                                                                 64

(2) INFORMATION FOR SEQ ID NO:42:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:42:

CTAGAGCCCT GGACCGTAAC AGAAAGGAGG ACAAGCCCCA GAACAATGAG AGCCTTCATG     60

GTGG                                                                 64

(2) INFORMATION FOR SEQ ID NO:43:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:43:

GATCATAGCG CACTATTATA GCACCATGAA GGCTCTCATT GTTCTGGGGC TTGTCCTCCT     60

TTCTGTTACG GTCCAGGGG                                                 79

(2) INFORMATION FOR SEQ ID NO:44:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:44:

GATCCCCCTG GACCGTAACA GAAAGGAGGA CAAGCCCCAG AACAATGAGA GCCTTCATGG     60

TGCTATAATA GTGCGCTAT                                                 79

(2) INFORMATION FOR SEQ ID NO:45:

(i) SEQUENCE CHARACTERISTICS:
            (A) LENGTH: 9014 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

CACTGGGTGC AAGCCCCAGA AACCGACGCC TATCTAAGTA GACGCAATGA CTCGGCGCCG     60

ACCCGGCGAC CGGCCAAAAG GTGGTGGATG GGTGATGCCA GGGTTGGTAG GTCGTAAATC    120

```
CCGGTCATCT TGGTAGCCAC TATAGGTGGG TCTTAAGGGA AGGTTAAGAT TCCTCTTGTG      180

CCTGTGGCGA GACAGCGCAC GGTCCACAGG TGTTGGCCCT ACCGGTGGGA ATAAGGGCCC      240

GACGTCAGGC TCGTCGTTAA ACCGAGACCG ACACCCACCT GGGCAAACGA CGCCCACGTA      300

CGGTCCACGT CGCCCTTCAA TGTCTCTCTT GACCAATAGG CTTTGCCGGC GAGTTGACAA      360

GGACCAGTGG GGGCCGGGGG TGGAGGGAAG GACCCTCTCA CCCTGYCCTT CCCGGTGGGA      420

CGGGAAATGC ATGGGCCAC  CCAGCTCCGC GGCGGCCTGC AGCCGGGGTA GCCCAAGAGC      480

CTTCGGGTGA GGGCGGGTGG CATTTTTCTT TTCTATACCG ATCATGGCAG TCCTTCTGCT      540

CTTCTTCGTG GTTGAGGCCG GGGCCATTCT GGCCCCGGCC ACCCACGCTT GCCGAGCTGA      600

TGGGCAATAT TTCCTCACAA ACTGTTGCGC CCCGGAGGAC ATTGGGTTCT GCCTGGAAGG      660

TGGATGCCTG GTGGCCTTGG GTTGCACTAT TTGTACTGAC CGATGCTGGC CACTGTATCA      720

GGCGGGTTTG GCTGTGCGGC CTGGCAAGTC CGCGGCCCAG CTGGTGGGGG AACTGGGGAG      780

CCTTTATGGG CCCTTGTCGG TCTCSGCYTA CGTGGCGGGG ATCTTGGGCC TAGGAGAGGT      840

TTACTCCGGT GTCCTCACGG TTGGGGTCGC GTTGACGCGC CGGGTCTACC CGGCCCCTAA      900

CCTGACGTGC ACCGTAGAGT GTGAGTTAAA GTGGGAAAGT GAGTTTTGGA GATGGACTGA      960

ACAGCTGGCC TCCAACTACT GGATTCTGGA ATATCTCTGG AAAGTGCCTT TTGACTTCTG     1020

GCGGGGAGTG ATGAGCTTGA CCCCCTTGTT GGTGTGTGTC GCGGCCCTCC TCCTGCTTGA     1080

GCAGAGGCTC GTCATGGTCT TCCTGTTGGT GACGATGGCT GGGATGTCGC AAGGCGCTCC     1140

GGCCTCCGTT TTGGGGTCAC GCCCCTTTGA CCGCGGGTTG ACATGGCAGT CTTGTTCTTG     1200

TAGGGCGAAT GGCTCACGCA TTCCTACTGG GGAGAAAGTT TGGGACCGAG GGAACGTCAC     1260

ACTTCTGTGT GACTGCCCCA ATGGCCCCTG GGTCTGGCTG CCGGCCGTGT RCCAAGCGAT     1320

CGGCTGGGGC GACCCTATCA CTCATTGGAG CCATGGACAA AATCAATGGC CCCTATCATG     1380

CCCCCAGTAC GTCTACGGTG CTGTTTCAGT GACATGCGTT TGGGGTTCCG TGTCTTGGTT     1440

TGCAACCACA GGTGGCCGCG ATTCCAAGCT CGACGTGTGG AGTTTGGTAC CAGTTGGCTC     1500

TGCCAGCTGC ACCATAGCCG CTCTCGGGTC ATCGGATCGT GACACCGTGG TGGAGCTCTC     1560

CGAGTGGGGG ATCCCTTGCG CTACCTGCAT TCTGGATCGT CGACCGGCCT CGTGTGGCAC     1620

CTGTGTGCGG GACTGCTGGC CCGAGACCGG GTCTGTCAGA TTCCCTTTCC ATCGGTGCGG     1680

CGCGGGGCCT AGGTTGACAA AGGACTTGGA AGCTGTGCCC TTCGTCAATA GGACAACTCC     1740

CTTCACCATA AGGGCCCCC  TGGGCAACCA GGGGAGAGGC AACCCGGTGC GGTCGCCCCT     1800

GGGTTTTGGG TCCTACACCA TGACCAAGAT CCGGGACTCC TTACATCTGG TGAAATGTCC     1860

CACACCAGCC ATTGAGCCTY CCACCGGGAC GTTTGGGTTC TTCCCTGGAG TGCCGCCCCT     1920

TAACAACTGC ATGCTCCTGG GCACTGAGGT GTCAGAAGCA TTGGGTGGGG CTGGCCTCAC     1980

GGGGGGGTTC TATGAACCCC TGGTGCGCAG GTGTTCGGAG CTGATGGGGC GCCGAAATCC     2040

GGTTTGCCCG GGGTACGCAT GGCTGTCCTC GGGTAGGCCT GATGGGTTCA TACATGTTCA     2100

GGGCCACTTG CAGGAGGTGG ATGCGGGCAA CTTCATCCCG CCTCCTTGCT GGTTGCTTTT     2160

GGACTTTGTA TTTGTCCTGT TATACCTGAT GAAGCTGGCG GAGGCACGGC TGGTCCCGCT     2220

GATACTTCTC CTGTTGTGGT GGTGGGTTAA CCAGCTGGCG GTCTTAGGAT TGCCGGCTGC     2280

TCACGCCGCC GTGGCGGGGG AGGTGTTTGC GGGTCCAGCC CTGTCGTGGT GTTTGGGCT      2340

CCCCTTCGTT AGTATGATAC TCGGTCTAGC AAACCTGGTG TTGTATTTCC GATGGATGGG     2400

GCCTCAACGT CTCATGTTCC TTGTGTTGTG GAAGCTCGCT CGGGGGCTT   TCCCGCTGGC     2460

TCYCTTGATG GGGATTTCGG CTACCCGTGG TCGCACCTCA GTGCTCGGGG CCGAGTTCCG     2520
```

```
CTTCGACATG ACATTCGAGG TTGACACGTC GGTCTTGGGA TGGGTGGTTG CTAGTGTGGT    2580

TGCTTGGGCC ATAGCGCTCC TGAGCTCGAT GAGCGCAGGG GGGTGGAAGC ACAAAGCTGT    2640

GATCTACAGG ACGTGGTGCA AGGGGTACCA GGCCATACGC CAGAGGGTTG TGCGGAGCCC    2700

CCTCGGGGAG GGGCGTYCCA CAAAGCCTTT GACCATTGCT TGGTGCTTGG CCTCATACAT    2760

CTGGCCGGAC GCTGTGATGA TGGTGGTGGT CGCCATGGTT CTTCTCTTCG GCCTGTTCGA    2820

CGCGTTGGAC TGGGCTTTGG AGGAGCTCCT GGTGGCTAGG CCCTCGCTGC GGCGCCTTKC    2880

CCGGGTGGTT GAGTGTTGTG TKATGGCTGG CGAAAGGGCG ACCACCATAA GGCTGGTGTC    2940

CAAGATGTGT GCAAGAGGGG CCTACTTGTT CGATCACATG GGCTCTTTTT CGCGCGCTGT    3000

CAAGGAACGC TTGCTAGAAT GGGATGCCGC TCTCGAGCCT CTTTCATTCA CCAGGACGGA    3060

CTGTCGCATC ATTCGGGACG CCGCCAGGAC CTTGTCCTGC GGGCAGTGCG TTATGGGTTT    3120

ACCTGTAGTC GCGCGCCGTG GTGATGAAGT TTTGATCGGC GTTTTCCAAG ATGTGAATCA    3180

TCTGCCTCCC GGGTTTGTCC CGACCGCGCC TGTTGTCATC CGTCGGTGCG GGAAGGGCTT    3240

TCTCGGAGTC ACAAAGGCTG CCTTGACTGG ACGGGATCCT GACTTACACC CAGGGAACGT    3300

CATGGTGCTG GGGACGGCAA CGTCGCGAAG CATGGGAACA TGTCTGAACG GCTTGTTGTT    3360

CACAACATTC CATGGGGCTT CTTCCCGAAC CATCGCCACA CCCGTGGGGG CCCTAAATCC    3420

AAGATGGTGG TCGGCCAGTG ATGACGTAAC CGTGTACCCC CTACCTGATG GTGCTACCTC    3480

GCTGACCCCT TGCACATGCC AGGCGGAGTC CTGCTGGGTC ATCAGATCCG ACGGGCTTT    3540

GTGCCATGGC TTGTCCAAGG GAGACAAGGT TGAGCTCGAT GTGGCCATGG AGGTTTCTGA    3600

CTTTCGTGGT TCGTCGGGCT CGCCCGTCTT GTGCGACGAG GGACACGCAG TGGGAATGCT    3660

GGTGTCAGTG CTCCATTCAG GTGGTAGGGT GACGGCGGCC CGATTCACAC GGCCTTGGAC    3720

CCAAGTTCCA ACAGAGCCA AGACCACCAC TGAACCCCCG CCGGTTCCGG CAAAAGGAGT    3780

TTTCAAAGAG GCCCCGTTGT TTATGCCTAC GGGAGCCGGG AAGAGCACCC GGGTCCCGCT    3840

GGAGTACGGC AACATGGGTC ACAAGGTTCT GATTCTCAAC CCGTCGGTAG CTACTGTGAG    3900

GGCCATGGGC CCTTACATGG AGCGGTTGGC GGGCAAACAC CCAAGCATTT ACTGTGGACA    3960

CGATACAACA GCTTTCACGA GGATCACTGA CTCGCCCCTC ACGTACTCAA CCTACGGAAG    4020

GTTTTTGGCC AACCCTAGGC AGATGCTGCG GGGCGTATCG GTGGTAATCT GTGATGAGTG    4080

CCACAGTCAT GACTCTACGG TGTTGCTGGG TATTGGGCGG GTCCGGGAGC TGGCGCGGGG    4140

GTGTGGAGTT CAACTGGTTC TCTACGCCAC CGCCACGCCT CCGGGCTCGC CCATGACCCA    4200

GCACCCCTCA ATTATTGAGA CAAAGCTGGA YGTTGGWGAG ATCCCCTTTT ATGGGCATGG    4260

CATCCCCCTG GAGCGGATGA GGACCGGTAG GCACCTGGTA TTCTGCCACT CAAAGGCGGA    4320

GTGTGAGAGG CTGGCCGGCC AATTCTCCTC ACGGGGGGTT AATGCTGTTG CCTATTATAG    4380

GGGTAAGGAC AGTTCAATCA TCAAGGATGG TGACCTGGTG GTGTGCGCTA CTGACGCGCT    4440

ATCTACCGGK TACACAGGAA ACTTTGACTC CGTGACCGAC TGTGGTTTAG TGGTGGAGGA    4500

GGTCGTTGAG GTGACCCTTG ATCCCACCAT AACCATCTCC CTGCGGACAG TGCCTGCGTC    4560

GGCAGAATTG TCGATGCAAC GGCGAGGACG CACGGGTAGA GGCCGGTCTG GCGTTACTA    4620

CTACGCGGGG GTGGGCAAAG CCCCTGCTGG TGTGGTGAGG TCCGGGCCGG TCTGGTCGGC    4680

GGTGGAGGCC GGAGTGACCT GGTACGGAAT GGAACCTGAC CTGACAGCAA ACCTTCTGAG    4740

ACTGTACGAC GACTGCCCTT ACACCGCAGC CGTCGCGGCG GACATCGGGG AAGCCGCGGT    4800

GTTCTTTGCG GGGCTCGCCC CCCTTAGGAT GCATCCTGAT GTCAGCTGGG CAAAAGTGCG    4860
```

```
CGGCGTCAAC TGGCCCCTCC TGGTGGGCGT TCAGCGGACC ATGTGCCGGG AAACACTGTC    4920

TCCCGGTCCA TCGGATGACC CCCAGTGGGC AGGTCTGAAG GGCCCAAATC CAGTCCCATT    4980

ACTGCTGAGG TGGGGCAATG ATTTACCATC GAAAGTGGCC GGCCATCACA TAGTGGACGA    5040

CTTGGTCCGT CGCCTGGGTG TGGCCGAGGG TTATGTCCGC TGTGACGCGG GCCCCATCTT    5100

GATGGTGGGG CTTGCGATCG CGGGGGGGAT GATCTACGCG TCATACACCG GGTCACTTGT    5160

GGTGGTTACA GACTGGGATG TGAAGGGGGG TGGCAACCCC CTTTATAGGA GTGGAGACCA    5220

AGCCACCCCA CAGCCGGTTG TGCAGGTCCC TCCGGTAGAC CATCGGCCGG GGGGGGAATC    5280

TGCGCCATCG GATGCCAAGA CAGTGACAGA TGCGGTGGCA GCCATCCAAG TGGACTGTGA    5340

TTGGTCAGTC ATGACCCTGT CGATCGGGA AGTGCTTTCC TTGGCTCAGG CTAAGACAGC    5400

CGAGGCCTAC ACAGCAACCG CAAAGTGGCT CGCTGGCTGC TATACGGGGA CGCGGGCCGT    5460

CCCCACAGTA TCAATTGTGG ACAAGCTCTT CGCCGGCGGG TGGGCGGCCG TGGTGGGTCA    5520

CTGCCACAGC GTCATAGCTG CGGCGGTGGC TGCTTACGGG GCTTCTAGGA GTCCCCGTT    5580

GGCTGCCGCG GCTTCCTACC TAATGGGGTT GGGCGTCGGA GGCAATGCGC AGACGCGTCT    5640

GGCTTCCGCC CTTCTTCTGG GGGCTGCTGG GACCGCCCTG GGCACCCCGG TCGTTGGTTT    5700

GACCATGGCC GGGGCGTTCA TGGGGGGGGC CAGCGTCTCC CCGTCCTTGG TCACCATTTT    5760

ACTGGGGGCC GTGGGCGGTT GGGAGGGCGT GGTTAACGCT GCTAGCCTCG TCTTCGACTT    5820

CATGGCAGGG AAATTATCAT CAGAAGACCT GTGGTATGCC ATCCCGGTAC TCACTAGCCC    5880

GGGCGCGGGC CTCGCGGGGA TCGCGCTCGG GTTGGTGTTG TATTCAGCTA ACAACTCTGG    5940

CACTACCACT TGGCTGAATC GTCTGCTAAC CACCCTGCCA CCTTCATCGT GCATCCCTGA    6000

CAGTTACTTC CAGCAAGCCG ATTACTGTAA CAAGGTCTCG GCCGTGCTCC GGCGCCTGAG    6060

CCTCACCCGA ACAGTGGTTG CCCTTGTGAA CAGGGAACCA AAGGTTGACG AGGTTCAGGT    6120

CGGATACGTC TGGGACTTGT GGGAGTGGAT CATGCGTCAA GTGCGCATGG TCATGGCCAG    6180

ACTCCGRGCC CTCTGTCCCG TGGTGTCACT ACCCTTGTGG CACTGCGGTG AGGGATGGTC    6240

CGGGGAGTGG CTGCTGGATG GGCATGTTGA GAGCCGCTGT CTTTGTGGGT GCGTGATAAC    6300

TGGTGACGTA CTGAATGGAC AACTCAAGGA GCCAGTTTAC TCTACAAAGC TGTGCCGGCA    6360

CTACTGGATG GGGACCGTAC CTGTGAACAT GTTGGGCTAC GGTGAAACCT CACCTCTCTT    6420

GGCCTCAGAC ACCCCGAAGG TGGTACCTTT TGGGACGTCG GGCTGGGCTG AGGTGGTGGT    6480

GACGCCGACC CATGTGGTAA TCAGGCGGAC CTCTTCCTAC AAGTTGCTGC GCCAGCAAAT    6540

CCTATCAGCT GCTGTTGCTG AGCCCTACTA TGTCGACGGC ATTCCGGTCT CGTGGGACGC    6600

AGATGCGAGA GCACCTGCCA TGGTCTATGG CCCTGGACAA AGTGTTACCA TTGACGGGGA    6660

GCGCTACACC TTGCCGCACC AACTGCGGCT TAGGAACGTA GCGCCCTCTG AGGTTTCATC    6720

CGAGGTGTCC ATAGACATTG GGACGGAGAC TGAAGACTCA GAACTGACTG AGGCCGACTT    6780

GCCGCCGGCA GCTGCAGCCC TTCAAGCGAT CGAGAATGCT GCGAGAATTC TTGAACCGCA    6840

TATTGATGTC ATCATGGAGG ATTGCAGTAC ACCCTCTCTC TGTGGTAGTA GCCGAGAGAT    6900

GCCTGTGTGG GGAGAAGACA TCCCCSGCAC TCCATCGCCT GCACTTATCT CGGTTACGGA    6960

GAGCAGCTCA GATGAGAAGA CCCCGTCGGT GTCCTCCTCG CAGGAGGATA CCCCGTCCTC    7020

AGACTCATTC GAAGTCATCC AAGAGTCAGA GACAGCTGAG GGGGAGGACA GTGTCTTCAA    7080

CGTGGCTCTT TCTGTACTAA AGCCTTGTT TCCACAGAGC GATGCCACTC GGAAACTGAC    7140

GGTCAAGATG TCATGCTGCG TGGAGAAGAG CGTCACTCGC TTCTTTTCCT TGGGGTTGAC    7200

GGTGGCCGAT GTGGCTAGCC TGTGTGAAAT GGAAATCCAG AACCATACAG CCTATTGTGA    7260
```

```
CAAGGTGCGC ACTCCGCTTG AATTGCAGGT TGGGTGCTTG GTGGGCAATG AACTTACCTT      7320

TGAATGTGAC AAGTGTGAGG CAAGGCAAGA GACCTTGGCC TCCTTCTCCT ACATATGGTC      7380

CGGTGTCCCG CTGACGCGGG CCACTCCGGC CAAACCCCCA GTGGTGAGGC CGGTTGGTTC      7440

GCTGTTGGTG GCCGACACCA CCAAGGTGTA TGTGACCAAC CCGGACAACG TGGGGAGAAG      7500

AGTGGACAAG GTGACCTTCT GGCGTGCCCC TCGAGTCCAT GACAAATTTC TCGTGGACTC      7560

GATCGAGCGC GCTAGAAAGG CAGCTCAAGC ATGCCTAAGC ATGGGTTACA CTTATGAGGA      7620

GGCAATAAGG ACTGTTAGGC CACATGCTGC CATGGGCTGG GGATCTAAGG TGTCGGTTAA      7680

AGACTTGGCC ACCCCTGCGG GGAAGATGGC TGTCCACGAC CGACTTCAGG AGATACTTGA      7740

GGGGACTCCG GTTCCCTTTA CCCTGACTGT GAAAAAGGAG GTGTTCTTCA AGACCGAAA      7800

GGAGGAGAAG GCCCCCCGCC TCATTGTGTT CCCCCCTCTG GACTTCCGGA TAGCTGAAAA      7860

GCTTATTTTG GGAGACCCGG GGCGGGTAGC CAAGGCGGTG TTGGGGGGGG CTTACGCCTT      7920

CCAGTACACC CCAAACCAGC GCGTCAAGGA GATGCTCAAG CTATGGGAGT CAAAGAAAAC      7980

ACCATGTGCC ATCTGTGTGG ACGCCACGTG CTTCGACAGT AGCATTACTG AAGAGGACGT      8040

GGCCTTGGAG ACAGAGCTTT ATGCCCTGGC TTCGGACCAT CCAGAGTGGG TGCGGGCCCT      8100

AGGGAAATAC TATGCCTCAG GCACCATGGT CACTCCGGAA GGGGTGCCCG TCGGTGAGAG      8160

GTATTGTAGA TCCTCTGGGG TCTTGACCAC TAGCGCGACG AATTGCTTGA CCTGCTACAT      8220

TAAGGTGTCA GCTGCCTGTC AGCGGGTGGG GCTGAAAAAT GTCTCGCTAC TGATAGCAGG      8280

TGACGACTGT CTGATCATAT GCGAACGGCC AGTGTGCGAC CCTAGCGAAG CCTTGGGCCG      8340

AGCCCTCGCT AGCTATGGGT ATGCATGCGA GCCTTCGTAT CATGCATCAC TGGACACGGC      8400

CCCCTTCTGC TCCACTTGGC TCGCCGAGTG TAATGCAGAT GGGAAGCGCC ATTTCTTCCT      8460

GACAACGGAC TTTCGGAGGC CGCTCGCTCG CATGTCGAGT GAGTACAGTG ACCCGATGGC      8520

TTCGGCCATC GGTTACATCC TCCTTTACCC CTGGCATCCC ATCACACGGT GGGTCATCAT      8580

TCCACACGTG CTGACTTGCG CGTTTAGGGG TGGTGGTACA CCGTCTGATC CGGTCTGGTG      8640

CCAGGTTCAT GGAAATTACT ACAAGTTTCC CCTGGACAAA CYGCCAAACA TCATCGTGGC      8700

CCTCCATGGA CCAGCAGCAT TGAGGGTTAC CGCAGACACA ACYAAAACAA AGATGGAAGC      8760

CGGCAAGGTG CTGAGCGACC TCAAGCTCCC GGGCTTAGCG GTCCACCGCA AGAAGGCCGG      8820

AGCACTGCGA ACTCGCATGC TTCGGTCGCG CGGTTGGGCT GAGTTGGCTC GGGGCCTGTT      8880

GTGGCATCCA GGCCWACGGC TCCCACCTCC GGAGATTGCT GGTATCCCCG GGGGTTTCCC      8940

CCTGTCCCCC CCCTACATGG GGGTGGTCCA TCAATTGGAT TTCACAAGCC AGAGGAGTCG      9000

CTGGCGGTGG TTGG                                                       9014
```

(2) INFORMATION FOR SEQ ID NO:46:

(i) SEQUENCE CHARACTERISTICS:
        (A) LENGTH: 2841 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

```
Gly Arg Val Ala Phe Phe Phe Ser Ile Pro Ile Met Ala Val Leu Leu
 1               5                  10                  15

Leu Phe Phe Val Val Glu Ala Gly Ala Ile Leu Ala Pro Ala Thr His
                20                  25                  30
```

-continued

```
Ala Cys Arg Ala Asp Gly Gln Tyr Phe Leu Thr Asn Cys Cys Ala Pro
         35                  40                  45

Glu Asp Ile Gly Phe Cys Leu Glu Gly Gly Cys Leu Val Ala Leu Gly
 50                  55                  60

Cys Thr Ile Cys Thr Asp Arg Cys Trp Pro Leu Tyr Gln Ala Gly Leu
 65                  70                  75                  80

Ala Val Arg Pro Gly Lys Ser Ala Ala Gln Leu Val Gly Glu Leu Gly
                 85                  90                  95

Ser Leu Tyr Gly Pro Leu Ser Val Ser Ala Tyr Val Ala Gly Ile Leu
             100                 105                 110

Gly Leu Gly Glu Val Tyr Ser Gly Val Leu Thr Val Gly Val Ala Leu
         115                 120                 125

Thr Arg Arg Val Tyr Pro Ala Pro Asn Leu Thr Cys Thr Val Glu Cys
130                 135                 140

Glu Leu Lys Trp Glu Ser Glu Phe Trp Arg Trp Thr Glu Gln Leu Ala
145                 150                 155                 160

Ser Asn Tyr Trp Ile Leu Glu Tyr Leu Trp Lys Val Pro Phe Asp Phe
                165                 170                 175

Trp Arg Gly Val Met Ser Leu Thr Pro Leu Leu Val Cys Val Ala Ala
             180                 185                 190

Leu Leu Leu Leu Glu Gln Arg Leu Val Met Val Phe Leu Leu Val Thr
         195                 200                 205

Met Ala Gly Met Ser Gln Gly Ala Pro Ala Ser Val Leu Gly Ser Arg
210                 215                 220

Pro Phe Asp Arg Gly Leu Thr Trp Gln Ser Cys Ser Cys Arg Ala Asn
225                 230                 235                 240

Gly Ser Arg Ile Pro Thr Gly Glu Lys Val Trp Asp Arg Gly Asn Val
                245                 250                 255

Thr Leu Leu Cys Asp Cys Pro Asn Gly Pro Trp Val Trp Leu Pro Ala
             260                 265                 270

Val Xaa Gln Ala Ile Gly Trp Gly Asp Pro Ile Thr His Trp Ser His
         275                 280                 285

Gly Gln Asn Gln Trp Pro Leu Ser Cys Pro Gln Tyr Val Tyr Gly Ala
290                 295                 300

Val Ser Val Thr Cys Val Trp Gly Ser Val Ser Trp Phe Ala Thr Thr
305                 310                 315                 320

Gly Gly Arg Asp Ser Lys Leu Asp Val Trp Ser Leu Val Pro Val Gly
                325                 330                 335

Ser Ala Ser Cys Thr Ile Ala Ala Leu Gly Ser Ser Asp Arg Asp Thr
             340                 345                 350

Val Val Glu Leu Ser Glu Trp Gly Ile Pro Cys Ala Thr Cys Ile Leu
         355                 360                 365

Asp Arg Arg Pro Ala Ser Cys Gly Thr Cys Val Arg Asp Cys Trp Pro
370                 375                 380

Glu Thr Gly Ser Val Arg Phe Pro Phe His Arg Cys Gly Ala Gly Pro
385                 390                 395                 400

Arg Leu Thr Lys Asp Leu Glu Ala Val Pro Phe Val Asn Arg Thr Thr
                405                 410                 415

Pro Phe Thr Ile Arg Gly Pro Leu Gly Asn Gln Gly Arg Gly Asn Pro
             420                 425                 430

Val Arg Ser Pro Leu Gly Phe Gly Ser Tyr Thr Met Thr Lys Ile Arg
         435                 440                 445
```

-continued

```
Asp Ser Leu His Leu Val Lys Cys Pro Thr Pro Ala Ile Glu Pro Xaa
    450                 455                 460
Thr Gly Thr Phe Gly Phe Pro Gly Val Pro Pro Leu Asn Asn Cys
465                 470                 475                 480
Met Leu Leu Gly Thr Glu Val Ser Glu Ala Leu Gly Gly Ala Gly Leu
                    485                 490                 495
Thr Gly Gly Phe Tyr Glu Pro Leu Val Arg Arg Cys Ser Glu Leu Met
                500                 505                 510
Gly Arg Arg Asn Pro Val Cys Pro Gly Tyr Ala Trp Leu Ser Ser Gly
            515                 520                 525
Arg Pro Asp Gly Phe Ile His Val Gln Gly His Leu Gln Glu Val Asp
    530                 535                 540
Ala Gly Asn Phe Ile Pro Pro Cys Trp Leu Leu Asp Phe Val
545                 550                 555                 560
Phe Val Leu Leu Tyr Leu Met Lys Leu Ala Glu Ala Arg Leu Val Pro
                565                 570                 575
Leu Ile Leu Leu Leu Leu Trp Trp Val Asn Gln Leu Ala Val Leu
                580                 585                 590
Gly Leu Pro Ala Ala His Ala Ala Val Ala Gly Glu Val Phe Ala Gly
            595                 600                 605
Pro Ala Leu Ser Trp Cys Leu Gly Leu Pro Phe Val Ser Met Ile Leu
    610                 615                 620
Gly Leu Ala Asn Leu Val Leu Tyr Phe Arg Trp Met Gly Pro Gln Arg
625                 630                 635                 640
Leu Met Phe Leu Val Leu Trp Lys Leu Ala Arg Gly Ala Phe Pro Leu
                645                 650                 655
Ala Xaa Leu Met Gly Ile Ser Ala Thr Arg Gly Arg Thr Ser Val Leu
                660                 665                 670
Gly Ala Glu Phe Arg Phe Asp Met Thr Phe Glu Val Asp Thr Ser Val
            675                 680                 685
Leu Gly Trp Val Val Ala Ser Val Val Ala Trp Ala Ile Ala Leu Leu
    690                 695                 700
Ser Ser Met Ser Ala Gly Gly Trp Lys His Lys Ala Val Ile Tyr Arg
705                 710                 715                 720
Thr Trp Cys Lys Gly Tyr Gln Ala Ile Arg Gln Arg Val Val Arg Ser
                725                 730                 735
Pro Leu Gly Glu Gly Arg Xaa Thr Lys Pro Leu Thr Ile Ala Trp Cys
                740                 745                 750
Leu Ala Ser Tyr Ile Trp Pro Asp Ala Val Met Met Val Val Ala
            755                 760                 765
Met Val Leu Leu Phe Gly Leu Phe Asp Ala Leu Asp Trp Ala Leu Glu
    770                 775                 780
Glu Leu Leu Val Ala Arg Pro Ser Leu Arg Arg Leu Xaa Arg Val Val
785                 790                 795                 800
Glu Cys Cys Val Met Ala Gly Glu Arg Ala Thr Thr Ile Arg Leu Val
                805                 810                 815
Ser Lys Met Cys Ala Arg Gly Ala Tyr Leu Phe Asp His Met Gly Ser
            820                 825                 830
Phe Ser Arg Ala Val Lys Glu Arg Leu Leu Glu Trp Asp Ala Ala Leu
    835                 840                 845
Glu Pro Leu Ser Phe Thr Arg Thr Asp Cys Arg Ile Ile Arg Asp Ala
850                 855                 860
Ala Arg Thr Leu Ser Cys Gly Gln Cys Val Met Gly Leu Pro Val Val
```

```
865                 870                 875                 880
Ala Arg Arg Gly Asp Glu Val Leu Ile Gly Val Phe Gln Asp Val Asn
                885                 890                 895
His Leu Pro Pro Gly Phe Val Pro Thr Ala Pro Val Val Ile Arg Arg
            900                 905                 910
Cys Gly Lys Gly Phe Leu Gly Val Thr Lys Ala Ala Leu Thr Gly Arg
            915                 920                 925
Asp Pro Asp Leu His Pro Gly Asn Val Met Val Leu Gly Thr Ala Thr
        930                 935                 940
Ser Arg Ser Met Gly Thr Cys Leu Asn Gly Leu Leu Phe Thr Thr Phe
945                 950                 955                 960
His Gly Ala Ser Ser Arg Thr Ile Ala Thr Pro Val Gly Ala Leu Asn
                965                 970                 975
Pro Arg Trp Trp Ser Ala Ser Asp Asp Val Thr Val Tyr Pro Leu Pro
            980                 985                 990
Asp Gly Ala Thr Ser Leu Thr Pro Cys Thr Cys Gln Ala Glu Ser Cys
            995                 1000                1005
Trp Val Ile Arg Ser Asp Gly Ala Leu Cys His Gly Leu Ser Lys Gly
        1010                1015                1020
Asp Lys Val Glu Leu Asp Val Ala Met Glu Val Ser Asp Phe Arg Gly
1025                1030                1035                1040
Ser Ser Gly Ser Pro Val Leu Cys Asp Glu Gly His Ala Val Gly Met
                1045                1050                1055
Leu Val Ser Val Leu His Ser Gly Gly Arg Val Thr Ala Ala Arg Phe
            1060                1065                1070
Thr Arg Pro Trp Thr Gln Val Pro Thr Asp Ala Lys Thr Thr Thr Glu
        1075                1080                1085
Pro Pro Pro Val Pro Ala Lys Gly Val Phe Lys Glu Ala Pro Leu Phe
        1090                1095                1100
Met Pro Thr Gly Ala Gly Lys Ser Thr Arg Val Pro Leu Glu Tyr Gly
1105                1110                1115                1120
Asn Met Gly His Lys Val Leu Ile Leu Asn Pro Ser Val Ala Thr Val
                1125                1130                1135
Arg Ala Met Gly Pro Tyr Met Glu Arg Leu Ala Gly Lys His Pro Ser
            1140                1145                1150
Ile Tyr Cys Gly His Asp Thr Thr Ala Phe Thr Arg Ile Thr Asp Ser
        1155                1160                1165
Pro Leu Thr Tyr Ser Xaa Tyr Gly Arg Phe Leu Ala Asn Pro Arg Gln
        1170                1175                1180
Met Leu Arg Gly Val Ser Val Val Ile Cys Asp Glu Cys His Ser His
1185                1190                1195                1200
Asp Ser Thr Val Leu Leu Gly Ile Gly Arg Val Arg Glu Leu Ala Arg
            1205                1210                1215
Gly Cys Gly Val Gln Leu Val Leu Tyr Ala Thr Ala Thr Pro Pro Gly
        1220                1225                1230
Ser Pro Met Thr Gln His Pro Ser Ile Ile Glu Thr Lys Leu Asp Val
        1235                1240                1245
Gly Glu Ile Pro Phe Tyr Gly His Gly Ile Pro Leu Glu Arg Met Arg
    1250                1255                1260
Thr Gly Arg His Leu Val Phe Cys His Ser Lys Ala Glu Cys Glu Arg
1265                1270                1275                1280
Leu Ala Gly Gln Phe Ser Ser Arg Gly Val Asn Ala Val Ala Tyr Tyr
            1285                1290                1295
```

```
Arg Gly Lys Asp Ser Ser Ile Ile Lys Asp Gly Asp Leu Val Val Cys
            1300                1305                1310
Ala Thr Asp Ala Leu Ser Thr Gly Tyr Thr Gly Asn Phe Asp Ser Val
        1315                1320                1325
Thr Asp Cys Gly Leu Val Val Glu Glu Val Val Glu Val Thr Leu Asp
    1330                1335                1340
Pro Thr Ile Thr Ile Ser Leu Arg Thr Val Pro Ala Ser Ala Glu Leu
1345                1350                1355                1360
Ser Met Gln Arg Arg Gly Arg Thr Gly Arg Gly Arg Ser Gly Arg Tyr
            1365                1370                1375
Tyr Tyr Ala Gly Val Gly Lys Ala Pro Ala Gly Val Val Arg Ser Gly
        1380                1385                1390
Pro Val Trp Ser Ala Val Glu Ala Gly Val Thr Trp Tyr Gly Met Glu
    1395                1400                1405
Pro Asp Leu Thr Ala Asn Leu Leu Arg Leu Tyr Asp Asp Cys Pro Tyr
        1410                1415                1420
Thr Ala Ala Val Ala Ala Asp Ile Gly Glu Ala Ala Val Phe Phe Ala
1425                1430                1435                1440
Gly Leu Ala Pro Leu Arg Met His Pro Asp Val Ser Trp Ala Lys Val
            1445                1450                1455
Arg Gly Val Asn Trp Pro Leu Leu Val Gly Val Gln Arg Thr Met Cys
        1460                1465                1470
Arg Glu Thr Leu Ser Pro Gly Pro Ser Asp Asp Pro Gln Trp Ala Gly
        1475                1480                1485
Leu Lys Gly Pro Asn Pro Val Pro Leu Leu Arg Trp Gly Asn Asp
        1490                1495                1500
Leu Pro Ser Lys Val Ala Gly His His Ile Val Asp Asp Leu Val Arg
1505                1510                1515                1520
Arg Leu Gly Val Ala Glu Gly Tyr Val Arg Cys Asp Ala Gly Pro Ile
            1525                1530                1535
Leu Met Val Gly Leu Ala Ile Ala Gly Gly Met Ile Tyr Ala Ser Tyr
        1540                1545                1550
Thr Gly Ser Leu Val Val Val Thr Asp Trp Asp Val Lys Gly Gly Gly
        1555                1560                1565
Asn Pro Leu Tyr Arg Ser Gly Asp Gln Ala Thr Pro Gln Pro Val Val
        1570                1575                1580
Gln Val Pro Pro Val Asp His Arg Pro Gly Gly Glu Ser Ala Pro Ser
1585                1590                1595                1600
Asp Ala Lys Thr Val Thr Asp Ala Val Ala Ala Ile Gln Val Asp Cys
            1605                1610                1615
Asp Trp Ser Val Met Thr Leu Ser Ile Gly Glu Val Leu Ser Leu Ala
        1620                1625                1630
Gln Ala Lys Thr Ala Glu Ala Tyr Thr Ala Thr Ala Lys Trp Leu Ala
        1635                1640                1645
Gly Cys Tyr Thr Gly Thr Arg Ala Val Pro Thr Val Ser Ile Val Asp
    1650                1655                1660
Lys Leu Phe Ala Gly Gly Trp Ala Ala Val Gly His Cys His Ser
1665                1670                1675                1680
Val Ile Ala Ala Ala Val Ala Ala Tyr Gly Ala Ser Arg Ser Pro Pro
            1685                1690                1695
Leu Ala Ala Ala Ala Ser Tyr Leu Met Gly Leu Gly Val Gly Gly Asn
        1700                1705                1710
```

-continued

```
Ala Gln Thr Arg Leu Ala Ser Ala Leu Leu Gly Ala Ala Gly Thr
    1715                1720                1725
Ala Leu Gly Thr Pro Val Val Gly Leu Thr Met Ala Gly Ala Phe Met
    1730                1735                1740
Gly Gly Ala Ser Val Ser Pro Ser Leu Val Thr Ile Leu Leu Gly Ala
1745                1750                1755                1760
Val Gly Gly Trp Glu Gly Val Val Asn Ala Ala Ser Leu Val Phe Asp
            1765                1770                1775
Phe Met Ala Gly Lys Leu Ser Ser Glu Asp Leu Trp Tyr Ala Ile Pro
            1780                1785                1790
Val Leu Thr Ser Pro Gly Ala Gly Leu Ala Gly Ile Ala Leu Gly Leu
    1795                1800                1805
Val Leu Tyr Ser Ala Asn Asn Ser Gly Thr Thr Thr Trp Leu Asn Arg
    1810                1815                1820
Leu Leu Thr Thr Leu Pro Pro Ser Ser Cys Ile Pro Asp Ser Tyr Phe
1825                1830                1835                1840
Gln Gln Ala Asp Tyr Cys Asn Lys Val Ser Ala Val Leu Arg Arg Leu
            1845                1850                1855
Ser Leu Thr Arg Thr Val Val Ala Leu Val Asn Arg Glu Pro Lys Val
            1860                1865                1870
Asp Glu Val Gln Val Gly Tyr Val Trp Asp Leu Trp Glu Trp Ile Met
        1875                1880                1885
Arg Gln Val Arg Met Val Met Ala Arg Leu Arg Ala Leu Cys Pro Val
    1890                1895                1900
Val Ser Leu Pro Leu Trp His Cys Gly Glu Gly Trp Ser Gly Glu Trp
1905                1910                1915                1920
Leu Leu Asp Gly His Val Glu Ser Arg Cys Leu Cys Gly Cys Val Ile
            1925                1930                1935
Thr Gly Asp Val Leu Asn Gly Gln Leu Lys Glu Pro Val Tyr Ser Thr
            1940                1945                1950
Lys Leu Cys Arg His Tyr Trp Met Gly Thr Val Pro Val Asn Met Leu
    1955                1960                1965
Gly Tyr Gly Glu Thr Ser Pro Leu Leu Ala Ser Asp Thr Pro Lys Val
    1970                1975                1980
Val Pro Phe Gly Thr Ser Gly Trp Ala Glu Val Val Val Thr Pro Thr
1985                1990                1995                2000
His Val Val Ile Arg Arg Thr Ser Ser Tyr Lys Leu Leu Arg Gln Gln
            2005                2010                2015
Ile Leu Ser Ala Ala Val Ala Glu Pro Tyr Tyr Val Asp Gly Ile Pro
            2020                2025                2030
Val Ser Trp Asp Ala Asp Ala Arg Ala Pro Ala Met Val Tyr Gly Pro
    2035                2040                2045
Gly Gln Ser Val Thr Ile Asp Gly Glu Arg Tyr Thr Leu Pro His Gln
    2050                2055                2060
Leu Arg Leu Arg Asn Val Ala Pro Ser Glu Val Ser Ser Glu Val Ser
2065                2070                2075                2080
Ile Asp Ile Gly Thr Glu Thr Glu Asp Ser Glu Leu Thr Glu Ala Asp
            2085                2090                2095
Leu Pro Pro Ala Ala Ala Ala Leu Gln Ala Ile Glu Asn Ala Ala Arg
            2100                2105                2110
Ile Leu Glu Pro His Ile Asp Val Ile Met Glu Asp Cys Ser Thr Pro
        2115                2120                2125
Ser Leu Cys Gly Ser Ser Arg Glu Met Pro Val Trp Gly Glu Asp Ile
```

-continued

```
            2130                2135                2140
Pro Xaa Thr Pro Ser Pro Ala Leu Ile Ser Val Thr Glu Ser Ser Ser
2145                2150                2155                2160
Asp Glu Lys Thr Pro Ser Val Ser Ser Gln Glu Asp Thr Pro Ser
            2165                2170                2175
Ser Asp Ser Phe Glu Val Ile Gln Ser Glu Thr Ala Glu Gly Glu
        2180                2185                2190
Asp Ser Val Phe Asn Val Ala Leu Ser Val Leu Lys Ala Leu Phe Pro
        2195                2200                2205
Gln Ser Asp Ala Thr Arg Lys Leu Thr Val Lys Met Ser Cys Cys Val
2210                2215                2220
Glu Lys Ser Val Thr Arg Phe Phe Ser Leu Gly Leu Thr Val Ala Asp
2225                2230                2235                2240
Val Ala Ser Leu Cys Glu Met Glu Ile Gln Asn His Thr Ala Tyr Cys
            2245                2250                2255
Asp Lys Val Arg Thr Pro Leu Glu Leu Gln Val Gly Cys Leu Val Gly
            2260                2265                2270
Asn Glu Leu Thr Phe Glu Cys Asp Lys Cys Glu Ala Arg Gln Glu Thr
        2275                2280                2285
Leu Ala Ser Phe Ser Tyr Ile Trp Ser Gly Val Pro Leu Thr Arg Ala
        2290                2295                2300
Thr Pro Ala Lys Pro Pro Val Val Arg Pro Val Gly Ser Leu Leu Val
2305                2310                2315                2320
Ala Asp Thr Thr Lys Val Tyr Val Thr Asn Pro Asp Asn Val Gly Arg
            2325                2330                2335
Arg Val Asp Lys Val Thr Phe Trp Arg Ala Pro Arg Val His Asp Lys
            2340                2345                2350
Phe Leu Val Asp Ser Ile Glu Arg Ala Arg Lys Ala Ala Gln Ala Cys
        2355                2360                2365
Leu Ser Met Gly Tyr Thr Tyr Glu Glu Ala Ile Arg Thr Val Arg Pro
        2370                2375                2380
His Ala Ala Met Gly Trp Gly Ser Lys Val Ser Val Lys Asp Leu Ala
2385                2390                2395                2400
Thr Pro Ala Gly Lys Met Ala Val His Asp Arg Leu Gln Glu Ile Leu
            2405                2410                2415
Glu Gly Thr Pro Val Pro Phe Thr Leu Thr Val Lys Lys Glu Val Phe
            2420                2425                2430
Phe Lys Asp Arg Lys Glu Glu Lys Ala Pro Arg Leu Ile Val Phe Pro
        2435                2440                2445
Pro Leu Asp Phe Arg Ile Ala Glu Lys Leu Ile Leu Gly Asp Pro Gly
        2450                2455                2460
Arg Val Ala Lys Ala Val Leu Gly Gly Ala Tyr Ala Phe Gln Tyr Thr
2465                2470                2475                2480
Pro Asn Gln Arg Val Lys Glu Met Leu Lys Leu Trp Glu Ser Lys Lys
            2485                2490                2495
Thr Pro Cys Ala Ile Cys Val Asp Ala Thr Cys Phe Asp Ser Ser Ile
            2500                2505                2510
Thr Glu Glu Asp Val Ala Leu Glu Thr Glu Leu Tyr Ala Leu Ala Ser
        2515                2520                2525
Asp His Pro Glu Trp Val Arg Ala Leu Gly Lys Tyr Tyr Ala Ser Gly
        2530                2535                2540
Thr Met Val Thr Pro Glu Gly Val Pro Val Gly Glu Arg Tyr Cys Arg
2545                2550                2555                2560
```

Ser Ser Gly Val Leu Thr Thr Ser Ala Thr Asn Cys Leu Thr Cys Tyr
            2565                2570                2575

Ile Lys Val Ser Ala Ala Cys Gln Arg Val Gly Leu Lys Asn Val Ser
        2580                2585                2590

Leu Leu Ile Ala Gly Asp Asp Cys Leu Ile Ile Cys Glu Arg Pro Val
        2595                2600                2605

Cys Asp Pro Ser Glu Ala Leu Gly Arg Ala Leu Ala Ser Tyr Gly Tyr
        2610                2615                2620

Ala Cys Glu Pro Ser Tyr His Ala Ser Leu Asp Thr Ala Pro Phe Cys
2625                2630                2635                2640

Ser Thr Trp Leu Ala Glu Cys Asn Ala Asp Gly Lys Arg His Phe Phe
            2645                2650                2655

Leu Thr Thr Asp Phe Arg Arg Pro Leu Ala Arg Met Ser Ser Glu Tyr
            2660                2665                2670

Ser Asp Pro Met Ala Ser Ala Ile Gly Tyr Ile Leu Leu Tyr Pro Trp
        2675                2680                2685

His Pro Ile Thr Arg Trp Val Ile Ile Pro His Val Leu Thr Cys Ala
        2690                2695                2700

Phe Arg Gly Gly Gly Thr Pro Ser Asp Pro Val Trp Cys Gln Val His
2705                2710                2715                2720

Gly Asn Tyr Tyr Lys Phe Pro Leu Asp Lys Xaa Pro Asn Ile Ile Val
            2725                2730                2735

Ala Leu His Gly Pro Ala Ala Leu Arg Val Thr Ala Asp Thr Thr Lys
            2740                2745                2750

Thr Lys Met Glu Ala Gly Lys Val Leu Ser Asp Leu Lys Leu Pro Gly
        2755                2760                2765

Leu Ala Val His Arg Lys Lys Ala Gly Ala Leu Arg Thr Arg Met Leu
        2770                2775                2780

Arg Ser Arg Gly Trp Ala Glu Leu Ala Arg Gly Leu Leu Trp His Pro
2785                2790                2795                2800

Gly Xaa Arg Leu Pro Pro Pro Glu Ile Ala Gly Ile Pro Gly Gly Phe
            2805                2810                2815

Pro Leu Ser Pro Pro Tyr Met Gly Val Val His Gln Leu Asp Phe Thr
            2820                2825                2830

Ser Gln Arg Ser Arg Trp Arg Trp Leu
        2835                2840

(2) INFORMATION FOR SEQ ID NO:47:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

AAAATTTCTA GAGCCACCAT GAGGCTCGTC ATGGTCTTCC                                    40

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

AAAACCTCTA GAGCCACCAT GGCAGTCCTT CTGCTC                                    36

(2) INFORMATION FOR SEQ ID NO:49:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

AAAATTTCTA GATCACTATC CCCGCCARAA GTCRAAAGG                                 39

(2) INFORMATION FOR SEQ ID NO:50:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

AAAATTTCTA GAGCCACCAT GGCGCCTGTT GTCATCCGTC GG                             42

(2) INFORMATION FOR SEQ ID NO:51:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO::51:

AAAACCTCTA GATCACTATG TWACCACCAC WAGYGACCC                                 39

(2) INFORMATION FOR SEQ ID NO:52:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

AAAATTCCTA GGGCCACCAT GGTSGGRTAC GTCTGGGAYY TGTG                           44

(2) INFORMATION FOR SEQ ID NO:53:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
AAAACCCCTA GGTCACTAGG CMARGGTCTC TTGSCKTGCC                      40
```

(2) INFORMATION FOR SEQ ID NO:54:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
AAAATTGGAT CCAGGCGCGC CCGCCTCAGT GTTG                            34
```

(2) INFORMATION FOR SEQ ID NO:55:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

```
AAAATTGGAT CCTTAGGGCG ACCGCACCGG GTTGCCT                         37
```

(2) INFORMATION FOR SEQ ID NO:56:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

```
AAAACCGGAT CCTTACGGAA TGAAGTTGCC CGCATCC                         37
```

(2) INFORMATION FOR SEQ ID NO:57:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

```
ATATAGATCT GCCACCATGA GGCTCGTCAT GGTCTTCC                        38
```

(2) INFORMATION FOR SEQ ID NO:58:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

```
GATTAGATCT TCACTACGGA ATGAAGTTGC CCGCATCC                        38
```

(2) INFORMATION FOR SEQ ID NO:59:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:59:

ATATAGATCT AACCCATGCT TGTAGCGCGA AAGG                          34

(2) INFORMATION FOR SEQ ID NO:60:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:60:

GATTAGATCT TCACTATCCC CGCCARAAGT CRAAAGG                       37

(2) INFORMATION FOR SEQ ID NO:61:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:61:

ATATAGATCT GCCACCATGG CAGTCCTTCT GCTC                          34

(2) INFORMATION FOR SEQ ID NO:62:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:62:

ATATAGATCT GCCACCATGG CGCCTGTTGT CATCCGTCGG                    40

(2) INFORMATION FOR SEQ ID NO:63:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:63:

GATTAGATCT TCACTATGTW ACCACCACWA GYGACCC                       37

(2) INFORMATION FOR SEQ ID NO:64:

(i) SEQUENCE CHARACTERISTICS:
            (A) LENGTH: 42 base pairs
            (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:64:

ATATAGATCT GCCACCATGG TSGGRTACGT CTGGGAYYTG TG                    42

(2) INFORMATION FOR SEQ ID NO:65:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

GATTAGATCT TCACTAGGCM ARGGTCTCTT GSCKTGCC                         38

(2) INFORMATION FOR SEQ ID NO:66:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

ATATAGATCT GCCACCATGG CAGTCCTTCT GCTCCTAC                         38

(2) INFORMATION FOR SEQ ID NO:67:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

GATTAGATCT TCACTAAGTC TTGGCGTCTG TTGGGACT                         38

(2) INFORMATION FOR SEQ ID NO:68:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

GATCGGGATC CTGGCGCGCC CGCCTCAGTG T                                31

(2) INFORMATION FOR SEQ ID NO:69:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)
```

-continued (xi) SEQUENCE DESCRIPTION: SEQ ID NO:69:

ATATACTGCA GCTATCACTT GTCGTCGTCG TCCTTGTAGT CCGGAATGAA GTTGCCCGCA    60

TCC    63

(2) INFORMATION FOR SEQ ID NO:70:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:70:

Gln Gly Ala Pro Ala Ser Val Leu Gly Ser Arg Pro Phe Gln
               5                   10